US007381810B2

(12) United States Patent
Robinson

(10) Patent No.: US 7,381,810 B2
(45) Date of Patent: Jun. 3, 2008

(54) POLYPHENOL OXIDASE GENES FROM LETTUCE

(75) Inventor: Simon Piers Robinson, Hawthorn (AU)

(73) Assignee: Commonwealth Scientific and Industrial Research Organistion, Campbell (AU)

( * ) Notice: Subject to any disclaimer, the term of this patent is extended or adjusted under 35 U.S.C. 154(b) by 518 days.

(21) Appl. No.: 10/619,646

(22) Filed: Jul. 15, 2003

(65) Prior Publication Data

US 2005/0191739 A1   Sep. 1, 2005

Related U.S. Application Data

(63) Continuation of application No. 09/443,067, filed on Feb. 15, 2000, now Pat. No. 6,627,794, and a continuation-in-part of application No. PCT/AU98/00362, filed on May 19, 1998, now abandoned, which is a continuation-in-part of application No. 08/976,222, filed on Nov. 21, 1997, now abandoned, which is a continuation-in-part of application No. PCT/AU96/00310, filed on May 22, 1996.

(30) Foreign Application Priority Data

| May 23, 1995 | (AU) | ................................. PN3098 |
| Sep. 26, 1995 | (AU) | ................................. PN5600 |
| May 22, 1996 | (WO) | .................... PCT/AU96/00310 |
| May 19, 1997 | (AU) | ................................. PN6849 |
| May 19, 1998 | (WO) | .................... PCT/AU98/00362 |

(51) Int. Cl.
*C07H 21/02* (2006.01)
*C12Q 1/68* (2006.01)
*C07K 1/00* (2006.01)

(52) U.S. Cl. ............................ 536/23.1; 530/350; 435/6
(58) Field of Classification Search ............... 536/23.1; 435/320.1, 6; 530/350
See application file for complete search history.

(56) References Cited

U.S. PATENT DOCUMENTS 4,940,835 A   7/1990 Shah et al.

FOREIGN PATENT DOCUMENTS

| WO | 8911227 | 11/1989 |
| WO | 9215599 | 9/1992 |
| WO | 9302195 | 2/1993 |
| WO | 9315599 | 8/1993 |
| WO | 9403607 | 2/1994 |
| WO | WO 9637617 | 11/1996 |
| WO | WO 9729193 | 8/1997 |
| WO | 8802372 | 4/1998 |

OTHER PUBLICATIONS

Newman SM. Organisation of the tomato polyphenol oxidase gene family. Plant Mol. Biol., vol. 21, p. 1035-1051, 1993.*

Boss PK. An apple polyphenol oxidase cDNA is up-regulated in wounded tissues. Plant Mol. Biol., vol. 27, p. 429-433, 1995.*

Cano et al., "Improvement of frozen banana (Musa cavendishii, cv. Enana) colour by blanching: Relationship between browning, phenols and polyphenol oxidase and peroxidase activities", Zeitschrift Fuer Lebensmittel-Untersuchung Und-Forschung, vol. 204, No. 1, 1997, pp. 60-65 (Exhibit 1).

Database Biosis 'Online! Biosciences Information Service, Philadelphia, PA, US; 1992, Zhou et al., "Mechanism of blackheart development induced by low temperature and gibberellic acid in pineapple fruit", Database accession No. PREV199396056342 (Exhibit 2).

Williams, et al., Derwent BIOT Online Abstract Accession No. 90-12612 (1990).

Steffens, Derwent BIOT Online Abstract Accession No. 95-05853 (1994).

Martinez, et al., Derwent BIOT Online Abstract Accession No. 95-05846 (1994).

Shahar, et al., The Plant Cell (1992) 4, pp. 135-147.

Dry, et al., Plant Molecular Biology (1994) 26, pp. 495-502.

Cary, et al., Plant Physiology (1990) 93, No. S.1, pp. 41, Abstract No. 230.

Steffens, et al., Plant Physiology (1990) 93, No. S.1, pp. 15, Abstract No. 82.

Hunt, et al., Plant Physiology (1992) 99, No. S.1, pp. 88, Abstract No. 526.

Batistuti, et al., Food Chemistry (1985) 18, pp. 251-263.

Van Der Krol, et al., Gene (1988) 72, pp. 45-50.

Finnegan, et al., Bio/Technology (1994) 12, pp. 883-888.

Matsuoka, et al., Proc. Natl. Acad. Sci. USA (1991) 88, pp. 834-838.

Ohara, et al., Proc. Natl. Acad. Sci. USA (1989) 86, pp. 5673-5677.

Twell, et al., Plant Molecular Biology (1987) 9, pp. 345-375.

Rezaian, et al., Journal of Virological Methods (1987) 17, pp. 277-285.

Sanger, et al., Proc. Natl. Acad. Sci. USA (1977) 74, No. 12, pp. 5463-5467.

Frohman, PCR Protocols: A Guide to Methods and Applications (1990), pp. 28-38.

Logemann, et al., Analytical Biochemistry (1987) 163, pp. 16-20.

Thygesen, et al., The Molecular and Cellular Biology of the Potato (1994), pp. 151-159.

(Continued)

*Primary Examiner*—Suryaprabha Chunduru
(74) *Attorney, Agent, or Firm*—John P. White; Cooper & Dunham LLP

(57) ABSTRACT

The present invention provides genetic sequences encoding polyphenol oxidase enzymes of lettuce, banana, tobacco and pineapple plants, and recombinant vectors comprising same, and methods of identifying related sequences using the nucleic acid molecules. The invention further provides methods of modifying PPO expression in plants using the inventive nucleic acid molecules.

9 Claims, 59 Drawing Sheets

OTHER PUBLICATIONS

Thygesen, et al., Plant Physiol. (1995) 109, pp. 525-531.
Joy, et al., Plant Physiol. (1995) 107, pp. 1083-1089.
Hunt, et al., Plant Molecular Biology (1993) 21, pp. 59-68.
Newman, et al., Plant Molecular Biology (1993) 21, pp. 1035-1051.
Cary, et al., Plant Molecular Biology (1992) 20, pp. 245-253.
Flurkey, et al., Plant Physiol. (1986) 81, pp. 614-6181.
Bachem, et al., Bio/Technology (1994) 12, pp. 1101-1105.
May, et al., Bio/Technology (1995) 13, pp. 486-492.
Sági, et al., Bio/Technology (1995) 13, pp. 481-485.
Michelmore, et al., Plant Cell Reports (1987) 6, pp. 439-442.
Curtis, et al., Journal of Experimental Botany (1994) 45, No. 279, pp. 1441-1449.
Robinson, et al., Plant Physiol. (1992) 99, pp. 317-323.
Rathjen, et al., Plant Physiol. (1992) 99, pp. 1619-1625.
Boss, et al., Plant Molecular Biology (1995) 27, pp. 429-433.
Hind, et al., Biochemistry (1995) 34, pp. 8157-8164.
Bucheli, et al., Plant Molecular Biology (1996) 31, pp. 1233-1238.
Goldman, et al., Plant Molecular Biology (1998) 36, pp. 479-485.
Haruta, et al., Biosci. Biotechnol. Biochem. (1998) 62 (2), pp. 358-362.
EMBL accession No. D87669 Published on Aug. 2, 1999.
EMBL accession No. D87670 Published on Aug. 2, 1999.
EMBL accession No. Y12501 Published on Feb. 25, 1998.
U.S. Appl. No. 09/443,067, filed Nov. 18, 1999 (Robinson), including the claim set as allowed (Exhibit B).

* cited by examiner

FIGURE 1A

```
    CACTGTGCGTATTGTGATGGGCCTACGACCAGATCGGCTTCCCCAACCTCGAGCTCCAA
1   ---------+---------+---------+---------+---------+---------+  +60
    GTGACACGCATAACACTACCGGATGCTGGTCTAGCCGAAGGGGTTGGAGCTCGAGGTT
     H  C  A  Y  C  D  G  A  Y  D  Q  I  G  F  P  N  L  E  L  Q

GTCCACAACTCCTGGCTCTTCTTCCCTTGGCACCGCTTCTACTTCCACGAGAGG
61  ---------+---------+---------+---------+---------+---------+  +120
    CAGGTGTTGAGGACCGAGAAGAAGGGAACCGTGGCGAAGATGGAGATGAAGGTGCTCTCC
     V  H  N  S  W  L  F  F  P  W  H  R  F  Y  L  Y  F  H  E  R

ATCCTCGGAAAGCTCATAGGCGACGACACTTTCGCCCTCCCTTTCTGGAACTGGGACGCG
121 ---------+---------+---------+---------+---------+---------+  +180
    TAGGAGCCTTTCGAGTATCCGCTGCTGTGAAAGCGGGAGGGAAAGACCTTGACCCTGCGC
     I  L  G  K  L  I  G  D  D  T  F  A  L  P  F  W  N  W  D  A

CCCGGCGGCATGAAGCTGCCGTCGATCTACGCCCAGTCCTCGTCGAGGAGATACTGTTC
181 ---------+---------+---------+---------+---------+---------+  +240
    GGGCCGCCGTACTTCGACGGCAGCTAGATGCGGGTCAGGAGCAGGAGCGAGATACTGTTC
     P  G  G  M  K  L  P  S  I  Y  A  D  P  S  S  S  L  Y  D  K

TTTCGCGACGCCAAGCACCAGCCGGTCCTGGTCGACCTCGACTACAACGGAACCGAC
241 ---------+---------+---------+---------+---------+---------+  +300
    AAAGCGCTGCGGTTCGTGGTCCGGCAGGACCAGCTGGAGCTGATGTTGCCTTGGCTG
     F  R  D  A  K  H  Q  P  P  V  L  V  D  L  D  Y  N  G  T  D
```

FIGURE 1B

```
     CCTAGTTTCACCGACGCGACAGAGCCAGATCGATCAGAACCTCAAGATCATGTACCGGCAGGTG
301  ----+----|----+----|----+----|----+----|----+----|----+----|  +360
     GGATCAAAGTGGCTGCGCTGTCTCGGTCTAGCTAGTCTTGGAGTTCTAGTACATGGCCGTCCAC
      P  S  F  T  D  A  E  Q  I  D  Q  N  L  K  I  M  Y  R  Q  V

ATCTCCAACGGCAAGACGCCGTTGCTCTTCTTGGGCTTCGGCTTACCGTGCCGGGCGACAAC
361  ----+----|----+----|----+----|----+----|----+----|----+----|  +420
     TAGAGGTTGCCGTTCTGCGGCAACGAGAAGAATCCGAGCCCGAATGGCACGGCCGCTGTTG
      I  S  N  G  K  T  P  L  L  F  L  G  S  A  Y  R  A  G  D  N

CCAAACCCCGGCGCGGGCTCGCTCGAGAACATACCACGGCCCCGTCCACGGGTGGACT
421  ----+----|----+----|----+----|----+----|----+----|----+----|  +480
     GGTTTGGGGCCGCGCCCGAGCGAGCTCTTGTATGGTGTGCCGGGCAGTGCCACCTGA
      P  N  P  G  A  G  S  L  E  N  I  P  H  G  P  V  H  G  W  T

GGCGACAGAAGCCAACTCCAATCTCGAGGACACATGGGCAACTTCTACTCCGCGGGGCGAC
481  ----+----|----+----|----+----|----+----|----+----|----+----|  +540
     CCGCTGTCTTCGGTTGGGTTAGAGCTCCTGTGTACCCGTTGAAGATGAGGCGCCCCGCTG
      G  D  R  S  Q  P  N  L  E  D  M  G  N  F  Y  S  A  G  R  D

CCTATCTTCTTCGCCCACCATTCAAATGTCGATCGCATGTGG
541  ----+----|----+----|----+----|----+----|--   582
     GGATAGAAGAAGCGGGTGGTAAGTTTACAGCTAGCGTACACC
      P  I  F  F  A  H  H  S  N  V  D  R  M  W
```

FIGURE 2A

```
    TTGCCGTTTTGGAATTGGGACGCGCCCGGGCCATGAAGCTGCCGTCGATCTACGCCGAC
1   ---------+---------+---------+---------+---------+---------+   +60
    AACGGCAAAACCTTAACCCTGCGCGGGCCCGGTACTTCGACGGCAGCTAGATGCGGCTG
     L  P  F  W  N  D  A  P  G  G  M  K  L  P  S  I  Y  A  D

CCTTCGTCCTCGCTCTCTATGACAAGTTTCGCGACGCCAAGCACCAGCCGCCGGTCCTCGTC
61  ---------+---------+---------+---------+---------+---------+   +120
    GGAAGCAGGAGCGAGATACTGTTCAAAGCGCTGCGGTTCGTGGTCGGCCAGGAGCAG
     P  S  S  L  Y  D  K  F  R  D  A  K  H  Q  P  P  V  L  V

GACCTCGACTACAACGGAACCGACCCTAGTTTCACCGACGCAGAGCAGATCGATCAGAAC
121 ---------+---------+---------+---------+---------+---------+   +180
    CTGGAGCTGATGTTGCCTTGGCTGGGATCAAAGTGGCTGCGTCTCGTCTAGTCTTG
     D  L  D  Y  N  G  T  D  P  S  F  T  D  A  E  Q  I  D  Q  N

CTCAAGATCATGTACCGGCAGGTGATCTCCAACGGCAAGACGCCGTTGCTCTTCTTAGGC
181 ---------+---------+---------+---------+---------+---------+   +240
    GAGTTCTAGTACATGGCCGTCCACTAGAGGTTGCCGTTCTGCGGCAACGAGAAGAATCCG
     L  K  I  M  Y  R  Q  V  I  S  N  G  K  T  P  L  L  F  L  G

TCGGGCTTACCGTGCCGGCGACAACCCAAACCCCGGTTTGGGTTTGGGCCGAGCCTCGAGAACATACCA
241 ---------+---------+---------+---------+---------+---------+   +300
    AGCCGAATGGCACGGCCGCTGTTGGGTTTGGGGCCGCGCCGAGCGAGCTCTTGTATGGT
     S  A  Y  R  A  G  D  N  P  N  P  G  A  G  S  L  E  N  I  P
```

FIGURE 2B

```
     CACGGCCCCGTCCAGGGTGGACTGGGCGACAGAAGCCAACCCAATCTCGAGGACATGGGC
301  ------+---------+---------+---------+---------+---------+  +360
     GTGCCGGGGCAGGTCCCACCTGACCCGCTGTCTTCGGTTGGGTTAGAGCTCCTGTACCCG
      H  G  P  V  H  G  W  T  G  D  R  S  Q  P  N  L  E  D  M  G

AACTTCTACTCCGCGGGCCGCGACCCCTATCTTCTTCGCCCACCATTCAAATGTCGATAGC
361  ------+---------+---------+---------+---------+---------+  +420
     TTGAAGATGAGGCGCCCCGGCGCTGGGATAGAAGAAGCGGGTGGTAAGTTTACAGCTATCG
      N  F  Y  S  A  G  R  D  P  I  F  F  A  H  H  S  N  V  D  S

ATGTGG
421  ------  426
     TACACC
      M  W
```

FIGURE 3A

```
    GTTGCTCTTCTTAGGCTCGGCTTACCGTGCCGGCGACAACCCAAACCCCGGCGGGGCTC
1   ------------------------------------------------------------+60
    CAACGAGAAGAATCCGAGCCGAATGGCACGGCCGCTGTTGGGTTTGGGCCGCGCCCGAG
     L  F  L  G  S  A  Y  R  A  G  D  N  P  N  P  G  A  G  S

GCTCGAGAACATACCACACGGCCCCGTCCACGGGTGGACTGGCGACAGAAACCAACCCAA
61  ------------------------------------------------------------+120
    CGAGCTCTTGTATGGTGTGCCGGGGCAGGTGCCCACCTGACCGCTGTCTTTGGTTGGGTT
     L  E  N  I  P  H  G  P  V  H  G  W  T  G  D  R  N  Q  P  N

TCTCGAGGACATGGGCAACTTCTACTCCGCGCGACCCTATCTTCTTCGCCACCA
121 ------------------------------------------------------------+180
    AGAGCTCCTGTACCCGTTGAAGATGAGGCGCGCTGGGATAGAAGAAGCGGGTGGT
     L  E  D  M  G  N  F  Y  S  A  G  R  D  P  I  F  F  A  H  H

TTCAAACGTCGACCGCATGTGGTACTTGTGGAAGAAGCTCGGCGGGAAGCATCAGGACTT
181 ------------------------------------------------------------+240
    AAGTTTGCAGCTGGCAGTACACCATGAACACCTTCTTCGAGCCGCCCTTCGTAGTCCTGAA
     S  N  V  D  R  M  W  Y  L  W  K  K  L  G  G  K  H  Q  D  F

TAACGATAAGGACTGGCTCAACACCACCTTCCTCTTCTACGACGAGAATGCTGACTTAGT
241 ------------------------------------------------------------+300
    ATTGCTATTCCTGACCGAGTTGTGGTGGAAGGAGAAGATGCTGCTCTTACGACTGAATCA
     N  D  K  D  W  L  N  T  T  F  L  F  Y  D  E  N  A  D  L  V
```

FIGURE 3B

```
     TCGAGTCACCCTCAAGGACTGCTTGCAGCCGGAGTGGCTTCGTTACGATTACCAAGACGT
301  ---------+---------+---------+---------+---------+---------+ +360
     AGCTCAGTGGGAGTTCCTGACGAACGTCGGCCTCACCGAAGCAATGCTAATGGTTCTGCA
      R  V  T  L  K  D  C  L  Q  P  E  W  L  R  Y  D  Y  Q  D  V

CGAGATCCCGTGGCTGAAGACTCGGCCGACTCCCAAAGCCTTGAAGGCGCAGAAAACCGC
361  ---------+---------+---------+---------+---------+---------+ +420
     GCTCTAGGGCACCGACTTCTGAGCCGGCTGAGGGTTTCGGAACTTCCGCGTCTTTTGGCG
      E  I  P  W  L  K  T  R  P  T  P  K  A  L  K  A  Q  K  T  A

AGCGAAAACACTGAAAGCTACAGCAGAGACGCCGTTCCCGGTGACGCTGCAATCCGCGGT
421  ---------+---------+---------+---------+---------+---------+ +480
     TCGCTTTTGTGACTTTCGATGTCGTCTCTGCGGCAAGGGCCACTGCGACGTTAGGCGCCA
      A  K  T  L  K  A  T  A  E  T  P  F  P  V  T  L  Q  S  A  V

GAGCACGACGGTGAGGAGGCCCAAGGTATCGAGGAGCGGCAAGGAGAAGGAAGAGGAAGA
481  ---------+---------+---------+---------+---------+---------+ +540
     CTCGTGCTGCCACTCCTCCGGGTTCCATAGCTCCTCGCCGTTCCTTCCTCTTCCTTCCTCT
      S  T  T  V  R  R  P  K  V  S  R  S  G  K  E  K  E  E  E  E

GGAGGTCCTCATCGTGGAGGGGATCGAGTTCGACCGCGACTACTTCATAAAGTTCGACGT
541  ---------+---------+---------+---------+---------+---------+ +600
     CCTCCAGGAGTAGCACCTCCCCCTAGCTCAAGCTGGCGCTGATGAAGTATTTCAAGCTGCA
      E  V  L  I  V  E  G  I  E  F  D  R  D  Y  F  I  K  F  D  V
```

FIGURE 3C

```
    CTTCGTGAACGCCACCGAGGGTGAGGGCATCACGCCGGGCGCCAGCGAGTTCGCGGGCAG
601 ------+---------+---------+---------+---------+---------+660
    GAAGCACTTGCGGTGGCTCCCACTCCCGCTAGTGCGGCCCGCGGTCGCTCAAGCGCCCGTC
     F  V  N  A  T  E  G  E  G  I  T  P  G  A  S  E  F  A  G  S

CTTCGTCAACGTCCCGCACAAGCACAAGAGCAAGAAGGAGAAGAAGCTGAAGACGAG
661 ------+---------+---------+---------+---------+---------+720
    GAAGCAGTTGCAGGGCGTGTTCGTGTTCTCGTTCTTCCTCTTCGACTTCTGCTC
     F  V  N  V  P  H  K  H  K  H  S  K  K  E  K  K  L  K  T  R

GCTCTGCCTGGGGATCACTGACCTGCTCGAGGACATCGGGGCGGAGGACGACGACAGCGT
721 ------+---------+---------+---------+---------+---------+780
    CGAGACGGACCCCTAGTGACTGGACGAGCTCCTGTAGCCCCGCCTCCTGCTGCTGTCGCA
     L  C  L  G  I  T  D  L  L  E  D  I  G  A  E  D  D  D  S  V

GCTCGTCACCATCGTCCCGAAAGCCGGAAAGGGCAAGGTGTCGGTCGCCGGCCTCCGCAT
781 ------+---------+---------+---------+---------+---------+840
    CGAGCAGTGGTAGCAGGGCTTTCGGCCTTTCCCGTTCCACAGCCAGCGGCCGGAGGCGTA
     L  V  T  I  V  P  K  A  G  K  G  K  V  S  V  A  G  L  R  I

CGATTCCCAAATTGAAGTAATACTATATATTTCTACTACCTATCAAGGAAAATAAAAGC
841 ------+---------+---------+---------+---------+---------+900
    GCTAAAGGGTTTAACTTCATTATGATATATAAAGATGATGGATAGTTCCTTTTATTTTCG
     D  F  P  N  *  S  N  T  I  Y  F  Y  Y  L  S  R  K  I  K  A

CGCACCATCGTAACAAAAAAAAAAA
901 ------+---------+------- 925
    GCGTGGTAGCATTGTTTTTTTTTTT
     A  P  S  *  Q  K  K  K
```

FIGURE 4A

```
    GTTGCTCTTCTTAGGCTCGGCTTACCGTGCCGGTGACCAGCCTAACCCCGGCGCGGGATC
1   ------+---------+---------+---------+---------+---------+ +60
    CAACGAGAAGAATCCGAGCCGAATGGCACGGCCACTGGTTCGGATTGGGGCCGCGCCCTAG
     L  L  F  L  G  S  A  Y  R  A  G  D  Q  P  N  P  G  A  G  S

CATCGAGAACATGCCGCACAACAACGTGCACTTGTGGACCGGCGACCGCACCCAGCCCAA
61  ------+---------+---------+---------+---------+---------+ +120
    GTAGCTCTTGTACGGCGTGTTGTTGCACGTGAACACCTGGCCGCTGGCCGTGGGTCGGGTT
     I  E  N  M  P  H  N  N  V  H  L  W  T  G  D  R  T  Q  P  N

CTTCGAGAACATGGCACCTTCTACGCGGCCGCGCGACCCCATCTTCTTCGCCACCA
121 ------+---------+---------+---------+---------+---------+ +180
    GAAGCTCTTGTACCCGTGGAAGATGCGCCGGCGCGCTGGGGTAGAAGAAGCGGGTGGT
     F  E  N  M  G  T  F  Y  A  A  A  R  D  P  I  F  F  A  H  H

CGCCAACATCGACCGAATGTGGTACCTGTGGAAGAAGCTCAGCAGGAAGCACCAGGACTT
181 ------+---------+---------+---------+---------+---------+ +240
    GCGGTTGTAGCTGGCTTACACCATGGACACCTTCTTCGAGTCGTCCTTCGTGGTCCTGAA
     A  N  I  D  R  M  W  Y  L  W  K  K  L  S  R  K  H  Q  D  F

CAATGACTCGGACTGGCTCAAAGCTTCCTTCCTCTTCTACGACGAGAACGCCGACTTAGT
241 ------+---------+---------+---------+---------+---------+ +300
    GTTACTGAGCCTGACCGAGTTTCGAAGGAAGGAGAAGATGCTGCTCTTGCGGCTGAATCA
     N  D  S  D  W  L  K  A  S  F  L  F  Y  D  E  N  A  D  L  V
```

FIGURE 4B

```
       TCGGGTCACGGTCAAGGACTGCTTGGAGACCGAGTGGCTGCGCTACACGTACCAAGACGT
301    ------+---------+---------+---------+---------+---------+   +360
       AGCCCAGTGCCAGTTCCTGACGAACCTCTGGCTCACCGACGCGATGTGCATGGTTCTGCA
        R  V  T  V  K  D  C  L  E  T  E  W  L  R  Y  T  Y  Q  D  V

GAAGATCCCATGGGCGAACACCCGACTCCCAAGCTCGCCAAGGCGAGGAAAGCCGG
361    ------+---------+---------+---------+---------+---------+   +420
       CTTCTAGGGTACCCGCTTGTGGGCTGAGGGTTCGAGCGGTTCCGCTCCTTTCGGCC
        K  I  P  W  A  N  T  R  P  T  P  K  L  A  K  A  R  K  A  G

CAGCAGATCGCTGAAAGCCACCGCGGAGGTGCAGTTCCCTGTGACGCTGGAATCCCCGGT
421    ------+---------+---------+---------+---------+---------+   +480
       GTCGTCTAGCGACTTTCGGTGGCGCCTCCACGTCAAGGGACACTGCGACCTTAGGGGCCA
        S  R  S  L  K  A  T  A  E  V  Q  F  P  V  T  L  E  S  P  V

CAAAGTGACGGTGAAGAGGCCCAAGGTGGGGAGGAGCGGAAGGAGAAGGAAGATGAGGA
481    ------+---------+---------+---------+---------+---------+   +540
       GTTTCACTGCCACTTCTCCGGGTTCCACCCCTCGCCGTTCCTCTTCCTTCTACTCCT
        K  V  T  V  K  R  P  K  V  G  R  S  G  K  E  K  E  D  E  E

GGAGATACTCATAGTGGAGGGGATCGAGTTCGACCGCGACTACTTCATCAAGTTCGACGT
541    ------+---------+---------+---------+---------+---------+   +600
       CCTCTATGAGTATCACCTCCCCTAGCTCAAGCTGGCCGCTGATGAAGTAGTTCAAGCTGCA
        E  I  L  I  V  E  G  I  E  F  D  R  D  Y  F  I  K  F  D  V
```

FIGURE 4C

```
     CTTCGTGAACGCGAACGGAGGGCGACGGCATCACGGCCGGGCCAGTGAGTTCGCCGGCAG
601  ------+---------+---------+---------+---------+---------+  660
     GAAGCACTTGCGCTGCCTGCCTCCCGCTGCCTAGTGCCGGCCCCGGTCACTCAAGCGGCCGTC
      F  V  N  A  T  E  G  D  G  I  T  A  G  A  S  E  F  A  G  S

CTTCGTGAACGTCCCGCACAAGCACCGCAAGGATGAGAATAAGCTGAAGACGAG
661  ------+---------+---------+---------+---------+---------+  720
     GAAGCACTTGCAGGGCGTGTTCGTGTTCCTACTCTTATTCGACTTCTGCTC
      F  V  N  V  P  H  K  H  R  K  D  E  N  K  L  K  T  R

GCTGTGTCTGGGAATCACCGACCTGCTCGAGGACATCGGCGCGGAGGACGACGACAGCGT
721  ------+---------+---------+---------+---------+---------+  780
     CGACACAGACCCTTAGTGGCTGGACGAGCTCCTGTAGCGCCGCCTCCTGCTGCTGTCGCA
      L  C  L  G  I  T  D  L  L  E  D  I  G  A  E  D  D  D  S  V

GCTCGTCACCATCGTGCCGAAGGCAGGCAAAGGAAAGGTGTCCGTCGGCGGTCTTCGGAT
781  ------+---------+---------+---------+---------+---------+  840
     CGAGCAGTGGTAGCACGGCTTCCGTCCGTTCCTTTCCTTCCACAGGCAGCCGCCAGAAGCCTA
      L  V  T  I  V  P  K  A  G  K  G  K  V  S  V  G  G  L  R  I

TGACTTTTCCAAGTGAGGAAATAAAAGAATTCACGTGCCGTGCCTGCTTTCAATGTACGA
841  ------+---------+---------+---------+---------+---------+  900
     ACTGAAAAGGTTCACTCCTTTATTTTCTTAAGTGCACGGCACGAAAGTTACATGCT
      D  F  S  K  *  G  N  K  R  I  H  V  P  C  L  L  S  M  Y  E

ATAAAATAAGAGTGCATCATCACCGACCATGGTTCTACTTTAAAAAAAAAAAAAAAA
901  ------+---------+---------+---------+---------+---------+  960
     TATTTTATTCTCACGTAGTAGTGGCTGGTACCAAGATGAAATTTTTTTTTTTTTTTT
      *  N  K  S  A  S  S  P  T  M  V  L  L  *  K  K  K  K  K
```

FIGURE 5A

```
    GATCCGACGTTGCGTTGCCATATTGGAACTGGGATCATCCAAAGGGCATGCGTTTGCCA
1   ------+---------+---------+---------+---------+---------+60
    CTAGGCTGCAAACGCAACGGCAACGGTATAACCTTGACCCTAGTAGGTTTCCCGTACGCAAACGGT
     D  P  T  F  A  L  P  Y  W  N  D  H  P  K  G  M  R  L  P

CACATGTTTGATCAACCAAACGTGTACCCTGATCTTTACGATCCAAGACGTAACCAAGAA
61  ------+---------+---------+---------+---------+---------+120
    GTGTACAAACTAGTTGGTTTGCACATGGGACTAGAAATGCTAGGTTCTGCATTGGTTCTT
     H  M  F  D  Q  P  N  V  Y  P  D  L  Y  D  P  R  R  N  Q  E

CACCGCGGTTCTGTAATCATGGACCTTGGTCATTTTGGTCAAGACGTGAAAGGAACTGAC
121 ------+---------+---------+---------+---------+---------+180
    GTGGCGCCAAGACATTAGTACCTGGAACCAGTAAAACCAGTTCTGCACTTCCTTGACTG
     H  R  G  S  V  I  M  D  L  G  H  F  G  Q  D  V  K  G  T  D

TTGCAAATGATGAGCAATAACCTTACTCTAATGTATCGTCAAATGATTACCAATTCACCA
181 ------+---------+---------+---------+---------+---------+240
    AACGTTTACTACTCGTTATTGGAATGAGATTACATAGCAGTTACTAATGGTTAAGTGGT
     L  Q  M  M  S  N  N  L  T  L  M  Y  R  Q  M  I  T  N  S  P

TGTCCAACTCTTTTTCGGTAAGCCATATTGTACGGAAGTTGGACCCAAACCAGGGCAG
241 ------+---------+---------+---------+---------+---------+300
    ACAGGTGTGAGAAAAAGCCATTCGGTATAACATGCCTTCAACCTGGGTTTGGTCCCGTC
     C  P  Q  L  F  F  G  K  P  Y  C  T  E  V  G  P  K  P  G  Q
```

FIGURE 5B

```
     GGAGCTATTGAAAACATCCCTCATACTCCTGTCCACATTTGGGTTGGTAGTAAGCCTAAT
301  ------+---------+---------+---------+---------+---------+  +360
     CCTCGATAACTTTTGTAGGGAGTATGAGGACAGGTGTAAACCAACCATCATTCGGATTA
      G  A  I  E  N  I  P  H  T  P  V  H  I  W  V  G  S  K  P  N

GAGAATAACTGTAAAAACGGTGAAGATATGGGAAATTTCTATTCAGCTGGTAAGGATCCT
361  ------+---------+---------+---------+---------+---------+  +420
     CTCTTATTGACATTTTGCCACTTCTATACCCTTTAAAGATAAGTCGACCATTCCTAGGA
      E  N  N  C  K  N  G  E  D  M  G  N  F  Y  S  A  G  K  D  P

GCTTTCTATAGTCACCATGCAAATGTAGATCGCAAATATGGAAACATTAGA
421  ------+---------+---------+---------+---------+---------+  +480
     CGAAAGATATCAGTGGTACGTTTACATCTAGCGTTATACCTTTTGTAATCCT
      A  F  Y  S  H  H  A  N  V  D  R  M  W  T  I  W  K  T  L  G

GGAAAACGCAAGGACATCAACAAGCCAGATTATTTGAACACTGAGTTCTTTTTCTACGAC
481  ------+---------+---------+---------+---------+---------+  +540
     CCTTTTGCGTTCCTGTAGTTGTTCGGTCTAATAAACTTGTGACTCAAGAAAAAGATGCTG
      G  K  R  K  D  I  N  K  P  D  Y  L  N  T  E  F  F  Y  D

GAAAA
541  -----  545
     CTTTT
      E
```

FIGURE 6A

```
     TGCACTGTGCGTATTGCAACGGTGCTTACAAAATTGGTGGCAAAGAGTTACAAGTCCATT
1    ------+---------+---------+---------+---------+---------+   +60
     ACGTGACACGCATAACGTTGCCACGAATGTTTTAACCACCGTTTCTCAATGTTCAGGTAA
      H  C  A  Y  C  N  G  A  Y  K  I  G  G  K  E  L  Q  V  H  F

TCTCGTGGCTTTTTTCCCTTTTCATAGATGGTACTTGTACTTCTATGAAAGAATCTTGG
61   ------+---------+---------+---------+---------+---------+   +120
     AGAGCACCGAAAAAAGGGAAAAGTATCTACCATGAACATGAAGATACTTTCTTAGAACC
      S  W  L  F  F  P  F  H  R  W  Y  L  Y  F  Y  E  R  I  L  G

GCTCTTTAATTAATGATCCTACTTTTGGTTTGCCATATATTGGAACTGGGACCATCCAAAGG
121  ------+---------+---------+---------+---------+---------+   +180
     CGAGAAATTAATTACTAGGATGAAAACCAAACGGTATAACCTTGACCCTGGTAGGTTTCC
      S  L  I  N  D  P  T  F  G  L  P  Y  W  N  D  H  P  K  G

GCATGCGTATACCTCCCATGTTCGATCGTGAAGGGTCTTCCCTTTACGACGAAAAACGTA
181  ------+---------+---------+---------+---------+---------+   +240
     CGTACGCATATGGAGGGTACAAGCTAGCACTTCCCAGAAGGAAATGCTGCTTTTGCAT
      M  R  I  P  P  M  F  D  R  E  G  S  S  L  Y  D  E  K  R  N

ACCAAAGTCACCGTAATGGAACCATAATTGATCTTGGTCATTTCGGTCAAGAAGTCCAAA
241  ------+---------+---------+---------+---------+---------+   +300
     TGGTTTCAGTGGCATTACCTTGGTATTAACTAGAACCAGTAAAGCCAGTTCTTCAGGTTT
      Q  S  H  R  N  G  T  I  I  D  L  G  H  F  G  Q  E  V  Q  T
```

FIGURE 6B

```
     CAACTCAACTGCAGCAGAGATGACTAATAACTTAACTATAAATGTATCGTCAAATGATAACTA
301  ----+----+----+----+----+----+----+----+----+----+----+----+  +360
     GTTGAGTTGACGTCGTCTACTGATTATTGAATTGATATTACATAGCAGTTACTATTGAT
       T  Q  L  Q  Q  M  T  N  N  L  T  I  M  Y  R  Q  M  I  T  N

ATGCTCCCTTGCCCTCTGCTCTTCTTTGGTCAGCCCTTACCCTCTAGGAACTGATCCCAGTC
361  ----+----+----+----+----+----+----+----+----+----+----+----+  +420
     TACGAGGGAACGGGAGACGAGAAGAAACCAGTCGGGAATGGGAGATCCTTGACTAGGGTCAG
       A  P  C  P  L  L  F  F  G  Q  P  Y  P  L  G  T  D  P  S  P

CAGGGATGGGCACTATTGAAAACATCCCTCATACTCCCTGTCCACATTTGGGTTGGTAGTA
421  ----+----+----+----+----+----+----+----+----+----+----+----+  +480
     GTCCCTACCCGTGATAACTTTTGTAGGGAGTATGAGGACAGGTGTAAACCCAACCATCAT
       G  M  G  T  I  E  N  I  P  H  T  P  V  H  I  W  V  G  S  R

GGCTTGATGAGAATAATACGAAACACGGTGAGGATATGGGTAATTTTTACTCGGCCGGTT
481  ----+----+----+----+----+----+----+----+----+----+----+----+  +540
     CCGAACTACTCTTATTATGCTTTGTGCCACTCCTATACCCATTAAAAATGAGCCGGCCAA
       L  D  E  N  N  T  K  H  G  E  I  M  G  N  F  Y  S  A  G  L

TAGACCCGCTTTCTATTCCCATCACGCCAATGTGGACCGGATGTGGTCCGAGTGGAAAG
541  ----+----+----+----+----+----+----+----+----+----+----+----+  +600
     ATCTGGGCGAAAGATAAGGGTAGTGCGGTTACACCTGGCCTACACCAGGCTCACCTTTC
       D  P  L  F  Y  S  H  H  A  N  V  D  R  M  W  S  E  W  K  A
```

FIGURE 6C

```
601 CCTTAGGAGGGAAAAGAAGGGATCTCACGCCACAAAGATTGGTTGAACTCCGAGTTCTTTT
    ------+---------+---------+---------+---------+---------+ +660
    GGAATCCTCCCTTTCTTCCCTAGAGTGCGGTGTTTCTAACCAACTTGAGGCTCAAGAAAA
     L  G  G  K  R  R  D  L  T  H  K  D  W  L  N  S  E  F  F

661 TCTACGATGAAAA
    ------+----- 673
    AGATGCTACTTTT
     Y  D  E
```

FIGURE 7A

```
    TGCATTGTGCGTATTGCAACGATGCTTACACAATGGGTGACCAAAAGTTACAAGTTCACC
1   ------+---------+---------+---------+---------+---------+   +60
    ACGTAACACGCATAACGTTGCTACGAATGTGTTACCCACTGGTTTCAATGTTCAAGTGG
     H  C  A  Y  C  N  D  A  Y  T  M  G  D  Q  K  L  Q  V  H  Q

AATCGTGGCTTTTCTTCCCGTTTCATAGATGGTACTTGTACTTCTACGAGAGAATCTTGG
61  ------+---------+---------+---------+---------+---------+   +120
    TTAGCACCGAAAAGAAGGGCAAAGTATCTACCATGAACATGAAGATGCTCTCTTAGAACC
     S  W  L  F  F  P  F  H  R  W  Y  L  Y  E  Y  E  R  I  L  G

GCTCCCTCATCGATGATCCAACTTTTGCTCTGCCATATTGGAACTGGGACCATCCAAGCG
121 ------+---------+---------+---------+---------+---------+   +180
    CGAGGGAGTAGCTACTAGGTTGAAAACGAGACGGTATAACCTTGACCCTGGTAGGTTCGC
     S  L  I  D  D  P  T  F  A  L  P  Y  W  N  D  H  P  S  G

GCATGCGTTTGCCTGCTATGTTCGATGTCGAAGGTTCTTCCCTCTACGATGCAAGACGTA
181 ------+---------+---------+---------+---------+---------+   +240
    CGTACGCAAACGGACGATACAAGCTACAGCTTCCAAGAAGGGAGATGCTACGTTCTGCAT
     M  R  L  P  A  M  F  D  V  E  G  S  S  L  Y  D  A  R  R  N

ATCCACATGTCCGTAATGGAACCATAATCGATCTTGGTTTTTTCGGTGATGAAGTCAAAA
241 ------+---------+---------+---------+---------+---------+   +300
    TAGGTGTACAGGCATTACCTTGGTATTAGCTAGAACCAAAAAAGCCACTACTTCAGTTTT
     P  H  V  R  N  G  T  I  I  D  L  G  F  F  G  D  E  V  K  T
```

FIGURE 7B

```
     CTAATGAAATACAGATGATAACTAACTTAATTCTAATGTATCGTCAAATGATAACTA
301  ------+---------+---------+---------+---------+---------+  360
     GATTACTTTATGTCTACTATTGATTGTTGAATTAAGATTACATAGCAGTTACTATTGAT
      N  E  I  Q  M  I  T  N  N  L  I  L  M  Y  R  Q  M  I  T  N

ATGCTCCATGCCCGCTGTTGTTCTTCGGAGAGCCTTACAGATTCGGATCTAAACCCAATC
361  ------+---------+---------+---------+---------+---------+  420
     TACGAGGTACGGGCGACAACAAGAAGCCTCTCGGAATGTCTAAGCCTAGATTGGGTTAG
      A  P  C  P  L  F  F  G  E  P  Y  R  F  G  S  K  P  N  P

CGGGGCAGGGAACCATTGAAAACATTCCTCATACTCCGGTTCACATTTGGACTGGTACTG
421  ------+---------+---------+---------+---------+---------+  480
     GCCCCGTCCCTTGGTAACTTTTGTAAGGAGTATGAGGCCAAGTGTAAACCTGACCATGAC
      G  Q  G  T  I  E  N  I  P  H  T  P  V  H  I  W  T  G  T  V

TGCGGGTGTACGGATTTGGGTAATTGTGTGCCATCATACGGTGAGGATATGGGTAATTTCT
481  ------+---------+---------+---------+---------+---------+  540
     ACGCCCACATGCCTAAACCCATTAACACACGGTAGTATGCCACTCCTATACCCATTAAAGA
      R  C  T  D  L  G  N  C  V  P  S  Y  G  E  D  M  G  N  F  Y

ACTCAGCTGGTTTAGACCCAGTTTTTTTACAGCCAAATGTCGGTGCGGTTACACCTGGCGTACACCT
541  ------+---------+---------+---------+---------+---------+  600
     TGAGTCGACCAAATCTGGGTCAAAAAATGTCGGTTACAGCCACGATGTGGACCGGCATGTGGA
      S  A  G  L  D  P  V  F  Y  S  H  H  A  N  V  D  R  M  W  N
```

FIGURE 7C

```
    ATGAATGGAAAGCACTAGGAGGAAAAGAAGGGATCTCACAGACAATGATTGGTTAAACT
601 ---------+---------+---------+---------+---------+---------+ +660
    TACTTACCTTTCGTGATCCTCCTTTTCTTCCCTAGAGTGTCTGTTACTAACCAATTTGA
     E  W  K  A  L  G  G  K  R  R  D  L  T  D  N  D  W  L  N  S

CGGAGTTCTTTTTCTACGACGAAAA
661 ---------+---------+----- 685
    GCCTCAAGAAAAGATGCTGCTTTT
     E  F  F  Y  D  E
```

FIGURE 8A

```
    TGCATTGTGCGTACTGCGACGGCGGTATGACCAAATCGGCTTCCCCGATCTCGAGATCC
1   ------+---------+---------+---------+---------+---------+60
    ACGTAACACGCATGACGCTGCCGCGCCATACTGGTTTAGCCGAAGGGGCTAGAGCTCTAGG
     H  C  A  Y  C  D  G  A  Y  D  Q  I  G  F  P  D  L  E  I  Q

AGATCCACAAACTCGTGGCTCTCTTCTTTCCTTGGCACCGGTTCTACCTCTACTTCAACGAGC
61  ------+---------+---------+---------+---------+---------+120
    TCTAGGTGTTGAGCACCGAGAGAAGAAACCGTGGCCAAGATGGAGATGAAGTTGCTCG
     I  H  N  S  W  L  F  F  P  W  H  R  F  Y  L  Y  F  N  E  R

GCATACTCGGGAAACTTATCGGCGACGACACGTTCGCGCTGCCTTTCTGGAACTGGGACG
121 ------+---------+---------+---------+---------+---------+180
    CGTATGAGCCCTTTGAATAGCCGCTGCTGTGCAAGCGCGACGGAAAGACCTTGACCCTGC
     I  L  G  K  L  I  G  D  D  T  F  A  L  P  F  W  N  W  D  A

CGGCCGGGGGCATGCAGTTCCCGTCTATCTACACGGACCCCTTCATCCTCGCTATATGACA
181 ------+---------+---------+---------+---------+---------+240
    GCCGGCCCCCGTACGTCAAGGGCAGATAGATGTGCCTGGAAGTAGGAGCGATATACTGT
     P  G  G  M  Q  F  P  S  I  Y  T  D  P  S  S  L  Y  D  K

AGCTGCGTGATGCGAAGCACCAGCCGCCCGACTTTGATTGACCTCGACTACAATGGCACCG
241 ------+---------+---------+---------+---------+---------+300
    TCGACGCACTACGCTTCGTGGTCGGCGGGCTGAAACTAACTGGAGCTGATGTTACCGTGGC
     L  R  D  A  K  H  Q  P  P  T  L  I  D  L  D  Y  N  G  T  D
```

FIGURE 8B

```
     ATCCTACCTTCTCCCCTGAAGAACAGATTAACCACAACCTGCGCCGTCATGTACCGACAGG
301  ------+---------+---------+---------+---------+---------+  +360
     TAGGATGGAAGAGGGACTTCTTGTCTAATTGGTGTTGGAGCGGCAGTACATGGCTGTCC
      P  T  F  S  P  E  E  Q  I  N  H  N  L  A  V  M  Y  R  Q  V

TGATATCCAGTGGAAAGACACCAGAGCTGTTTATGGGCTCAGCGTACCGCGCCGGTGACC
361  ------+---------+---------+---------+---------+---------+  +420
     ACTATAGGTCACCTTTCTGTGGTCTCGACAAATACCCGAGTCGCATGGCGCGGCCACTGG
      I  S  G  K  T  P  E  L  F  M  G  S  A  Y  R  A  G  D  Q

AGCCTGACCCCGGCGCAGGTTCTGTAGAGCAGAAGCCGCACGGCCCGGTGCATGTGTGA
421  ------+---------+---------+---------+---------+---------+  +480
     TCGGACTGGGGCCGCGTCCAAGACATCTCGTCTTCGGCGTGCCGGGCCACGTACACACCT
      P  D  P  G  A  G  S  V  E  Q  K  P  H  G  P  V  H  V  W  T

CAGGTGATCGCAACCAGCCCAATCGCGAAGACATGGGCACGCTCTACTCGGCGGCGTGGG
481  ------+---------+---------+---------+---------+---------+  +540
     GTCCACTAGCGTTGGTCGGGTTAGCGCTTCTGTACCCGTGCGAGATGAGCGCCGCCACCC
      G  D  R  N  Q  P  N  R  E  D  M  G  T  L  Y  S  A  A  W  D

ACCCCGTTTTTTCGCACACCACCGCAACATCGACCGCATGTGGTACGTGTGGAGGAACC
541  ------+---------+---------+---------+---------+---------+  +600
     TGGGGCAAAAAAGCGTGTGGTGGTGCCGTTGTAGCTGGCGTACACCATGCACACCTCCTTGG
      P  V  F  F  A  H  H  G  N  I  D  R  M  W  Y  V  W  R  N  L
```

FIGURE 8C

```
    TTGGCGGCAAGCACCGCAACTTCACCGACCCCGACTGGCTCAACGCGTCCTTCCTGTTCT
601 ---------+---------+---------+---------+---------+---------+ 660
    AACCGCCGTTCGTGGCGTTGAAGTGGCTGGGGCTGACCGAGTTGCGCAGGAAGGACAAGA
     G  G  K  H  R  N  F  T  D  P  D  W  L  N  A  S  F  L  F  Y

ACGACGAAAA
661 ---------+ 670
    TGCTGCTTTT
     D  E
```

FIGURE 9A

```
     TTGCCGTTTTGGAATTGGGACGCGCCCGGGGGCATGCAGATCCCGGCCATCTACGCCGAC
  1  ------+---------+---------+---------+---------+---------+    +60
     AACGGCAAAACCTTAACCCTGCGCGGGCCCCCGTACGTCTAGGGCCGGTAGATGCGGCTG
      L  P  F  W  N  W  D  A  P  G  G  M  Q  I  P  A  I  Y  A  D

GCTTCGTCCCCGCTCTACGACAAGCTGCGCAATGCGGAAGCACCAGCCGCCGACTTTGGTC
 61  ------+---------+---------+---------+---------+---------+   +120
     CGAAGCAGGGGCGAGATGCTGTTCGACGCGTTACGCCTTCGTGGTCGGCGGCTGAAACCAG
      A  S  S  P  L  Y  D  K  L  R  N  A  K  H  Q  P  P  T  L  V

GACCTCGACTACAACGGCACCGACCCGACCTTCACCCCTGAGCAGCAGATCGCCCACAAC
121  ------+---------+---------+---------+---------+---------+   +180
     CTGGAGCTGATGTTGCCGTGGCTGGGCTGGAAGTGGGGACTCGTCGTCTAGCGGGTGTTG
      D  L  D  Y  N  G  T  D  P  T  F  T  P  E  Q  Q  I  A  H  N

CTCACCATCATGTACCGACAGGTGATATCCGGCGGGAAGACGCCGGAGTTGTTTATGGGC
181  ------+---------+---------+---------+---------+---------+   +240
     GAGTGGTAGTACATGGCTGTCCACTATAGGCCGCCCTTCTGCGGCCTCAACAAATACCCG
      L  T  I  M  Y  R  Q  V  I  S  G  G  K  T  P  E  L  F  M  G

GCGGGCGTACCGCGCGGCGACGCCCCGGACCCCGGAGCAGGCACTCTAGAGCTCGTGCCG
241  ------+---------+---------+---------+---------+---------+   +300
     CGCCGCATGGCGCGCCGCTGCGGGGCCTGGGGCCTCGTCCGTGAGATCTCGAGCACGGC
      A  A  Y  R  A  G  D  A  P  D  P  G  A  G  T  L  E  L  V  P
```

FIGURE 9B

```
    CACAACACGATGCATTTGTGGACCGGCGACCCCAACCAACGACGAAGACATGGGC
301 ---------+---------+---------+---------+---------+---------+ +360
    GTGTTGTGCTACGTAAACACCTGGCCGCTGGGGTTGGTTGCTGCTTCTGTACCCG
     H  N  T  M  H  L  W  T  G  D  P  N  Q  P  N  D  E  D  M  G

ACGTTCTACGCGGCGGCGGCCCGCGACCCCATCTTCTTCGCCCACCGGCAACGTCGACCGC
361 ---------+---------+---------+---------+---------+---------+ +420
    TGCAAGATGCGCCGCCGCCGGGCGCTGGGGTAGAAGAAGCGGGTGGTGCCGTTGCAGCTGGCG
     T  F  Y  A  A  A  R  D  P  I  F  F  A  H  H  G  N  V  D  R

ATGTGGTACGTGTGGCGGGAAACTCGGGCACGCACCGCGATTTCACCGACCCCGACTGG
421 ---------+---------+---------+---------+---------+---------+ +480
    TACACCATGCACACCGCCCTTTGAGCCCCGTGCGTGGCGCTAAAGTGGCTGGGGCTGACC
     M  W  Y  V  W  R  K  L  G  G  T  H  R  D  F  T  D  P  D  W

CTCAACGCGTCCTTCCTCTTCTACGACGAGAACGCGCAGCTCGTCCGCGTCAAAGTAAAG
481 ---------+---------+---------+---------+---------+---------+ +540
    GAGTTGCGCAGGAAGGAGAAGATGCTGCTCTTGCGCGTCGAGCAGGCGCAGTTTCATTTC
     L  N  A  S  F  L  F  Y  D  E  N  A  Q  L  V  R  V  K  V  K

GACTGCTTGAGCGCCGACGCGGCTGCGCGACGTACCAGGACGTCGACATCCCGTGGATC
541 ---------+---------+---------+---------+---------+---------+ +600
    CTGACGAACTCGCGGCTGCGCCGACGCGCTGCATGGTCCTGCAGCTGTAGGCACCTAG
     D  C  L  S  A  D  A  L  R  Y  T  Y  Q  D  V  D  I  P  W  I
```

FIGURE 9C

```
    AGTGCGAAGCCGACGCCGAAGAAAACACCGGGGGCGCTGCGCCTTCCACGACAGAGGCT
601 ------+---------+---------+---------+---------+---------+ +660
    TCACGCTTCGGCTGCGGCTTCTTTTGTGGCCCCCGCGACGCGGAAGGTGCTGTCTCCGA
     S  A  K  P  T  P  K  K  K  T  P  G  G  A  A  P  S  T  T  E  A

ATATTCCGGTGGTGCTGGATAAGCCGGTTGAGCTCTACGGTGGCGAGGCCGAAGACGGGG
661 ------+---------+---------+---------+---------+---------+ +720
    TATAAAGGCCACCACGACCTATTCGGCCAACTCGAGATGCCACCGCTCCGGCTTCTGCCCC
     I  F  P  V  V  L  D  K  P  V  S  S  T  V  A  R  P  K  T  G

AGGAGTACTGGGGAGGAGGAGGTGTTGGTGGTGGAGGGAATCGAGCTGGACAAGGACGTG
721 ------+---------+---------+---------+---------+---------+ +780
    TCCTCATGACCCCTCCTCCTCCACAACCACCACCTCCCTTAGCTCGACCTGTTCCTGCAC
     R  S  T  G  E  E  E  V  L  V  V  E  G  I  E  L  D  K  D  V

GCCGTGAAGTTCGACGTGTATATAAACGCGCCGGACAACGAAGGGGGTGGGCCGGAGGCG
781 ------+---------+---------+---------+---------+---------+ +840
    CGGCACTTCAAGCTGCACATATATTTGCGCGGCCTGTTGCTTCCCCACCCCGGCCTCCGC
     A  V  K  F  D  V  Y  I  N  A  P  D  N  E  G  V  G  P  E  A

AGCGAGTTCGCAGGGAGCTTCGTCCAGGTGCCGCACAAGCACAAGAAGGGGAAGAAGGAG
841 ------+---------+---------+---------+---------+---------+ +900
    TCGCTCAAGCGTCCCTCGAAGCAGGTCCACGGCGTGTTCGTGTTCTTCCCCTTCTTCCTC
     S  E  F  A  G  S  F  V  Q  V  P  H  K  H  K  K  G  K  K  E
```

FIGURE 9D

```
     AAGGCGAGGATTAAAAACGACGCTCAGGCTCGGGATAACGGACCTGCTCGAGGACATCGGC
901  ------+---------+---------+---------+---------+---------+  +960
     TTCCGCTCCTAATTTTGCTGCGAGTCCGAGCCCTATTGCCTGGACGAGCTCCTGTAGCCG
       K  A  R  I  K  T  T  L  R  L  G  I  T  D  L  L  E  D  I  G

GCCGAGGACGACGAGAGCGTGCTCGTCACGCTCGTGCCGAGGATAGGCGAGGGGGTTGGTC
961  ------+---------+---------+---------+---------+---------+  +1020
     CGGCTCCTGCTGCTCTCGCACGAGCAGTGCGAGCACGGCTCCTATCCGCTCCCCAACCAG
       A  E  D  D  E  S  V  L  V  T  L  V  P  R  I  G  E  G  L  V

AAGGTTGGTGGGCTAAGGATCGATTTCTCCAAGTGATCAGCAGCAAATTAACTATACATG
1021 ------+---------+---------+---------+---------+---------+  +1080
     TTCCAACCACCCGATTCCTAGCTAAAGAGGTTCACTAGTCGTCGTTTAATTGATATGTAC
       K  V  G  G  L  R  I  D  F  S  K  *  S  A  A  N  *  L  Y  M

AAAGTAAAAAAAATTGCATTTAACGTAAATGGATGGATATCTTCTCTTATTACGCATAGACG
1081 ------+---------+---------+---------+---------+---------+  +1140
     TTTCATTTTTTTAACGTAAATTGCATTTACCTACCTATAGAAGAGAATAATGCGTATGTAATCTGC
       K  V  K  K  I  A  F  T  Y  L  *  K  R  I  N  A  Y  V  I  C

CCCATTTGTCACTTTTAATTTCTCGAGCGTGTTCTGAATGAGAGTTGCATGCGCGC
1141 ------+---------+---------+---------+---------+---------+  +1200
     GGGTAAACAGTGAAAATTAAAGAGCTCGCACAAGACTTACTCTCAACGTACGTACGCG
       P  I  C  H  F  *  F  L  E  R  V  L  N  E  S  C  M  H  A  R
```

FIGURE 9E

```
     AGCCATAAATGCCTGGTAGTGTAGTAGTTTAGGCGTGGATACGTATAACGTACGTATGC
1201 ----+----+----+----+----+----+----+----+----+----+----+----+1260
     TCGGTATTACGGACCATATCACATCATCAAATCCGCACCTATGCATATTGCATGCATACG
      S  H  N  A  W  Y  S  V  V  V  *  A  W  I  R  I  T  Y  V  C

ATGTATAAGGAATAATGATGAGTTTACTATGCAAAAAAAAAAAAAAAAAAAAAAAAAAAA
1261 ----+----+----+----+----+----+----+----+----+----+----+---- 1319
     TACATATTCCTTATTACTACTCAAATGATACGTTTTTTTTTTTTTTTTTTTTTTTTTTTT
      M  Y  K  E  *  *  *  V  Y  Y  A  K  K  K  K  K  K  K  K  K
```

FIGURE 10A

```
     CGGTATCGATAAGCTTGATCCAGTGCCTGGTTTAGGTGTATTCACTATGGCCACCCTCTC
  1  ------+---------+---------+---------+---------+---------+   +60
     GCCATAGCTATTCGAACTAGGTCACGGACCAAATCCACATAAGTGATACCGGTGGGAGAG
      G  I  D  K  L  D  P  V  P  G  L  G  V  F  T  M  A  T  L  S

TAAACTAGCTTCCCAACCAATAACACCTCCACTCTCCCCGTCTCCCTTCTTTGCATGCTCC
 61  ------+---------+---------+---------+---------+---------+   +120
     ATTTGATCGAAGGGTTGGTTATTGTGGAGGTGAGAGGGGCGAGGGAGGAAACGTACGAGG
      K  L  A  S  Q  P  I  T  P  P  L  S  P  L  P  P  L  H  A  P

TTCTCTCACCAAAAGCTTCACCACCACCTTCCTCTCCCCTGTAGGGTCCCAAACCACCC
121  ------+---------+---------+---------+---------+---------+   +180
     AAGAGAGTGGTTTTCGAAGTGGTGGTGGAAGGAGAGGGGACATCCCCAGGGTTTGGTGGG
      S  L  T  K  S  F  T  T  T  F  L  S  P  V  G  V  P  N  H  P

CGTCATAAGATCTCATGCAAATCTAAGGAGCAACAAGAGAATGCCGACAAGCCTGCGGGC
181  ------+---------+---------+---------+---------+---------+   +240
     GCAGTATTCTAGAGTACGTTTAGATTCCTCGTTGTTCTCTTACGGCTGTTCGGACGCCCG
      V  I  R  S  H  A  N  L  R  S  N  K  R  M  P  T  S  L  R  A

CGCATCGCCCGCCGCGACCTACTCCTCGGGCCCTCGGGCTTTACGGTGCCACCACTGG
241  ------+---------+---------+---------+---------+---------+   +300
     GCGTAGCGGGCGGCGCTGGATGAGGAGCCCGGGAGCCCGGGAGCCCGAAATGCCACGGTGGTGACC
      A  S  P  A  A  T  Y  S  W  A  L  G  G  L  Y  G  A  T  T  G
```

FIGURE 10B

```
     GCTCGGCCTCAACCGTCGAGCGGGCCGCCCCTATCCTGGCTCCCGACCTCTCAACTTG
301  ----+----+----+----+----+----+----+----+----+----+----+----+ +360
     CGAGCCGGAGTTGGCAGCTCGCCCGGCGGGGATAGGACCGAGGGCTGGAGAGTTGAAC
      L  G  L  N  R  R  A  A  A  A  P  I  L  A  P  D  L  S  T  C

TGGGCCGCCTGCCGACCTCCCTGCCTGGAGGACGGAGGACGGAGCTGGTCAAACGACGGGGTATGGT
361  ----+----+----+----+----+----+----+----+----+----+----+----+ +420
     ACCCGGCGGACGGCTGGAGGGACGGAGGACGGAGGACGGAGGACGGAGGACGGGCTAGACCATACCA
      G  P  P  A  D  L  P  A  S  A  R  P  T  V  C  C  P  P  Y  Q

ATCCACCATCATCGACTTCAAGCTCCCCCCGCGATCTGCTCCGCTTCGGCCTGC
421  ----+----+----+----+----+----+----+----+----+----+----+----+ +480
     TAGGTGGTAGTAGCTGAAGTTCGAGGGGGCGCTAGACGAGGCGAAGCCGAAGCCGGACG
      S  T  I  I  D  F  K  L  P  P  R  S  A  P  L  R  V  R  P  A

GGCCCACTTGGTTGACGCCGACTACCTGGCCAAGTATAAGAAGGCGGTCGAGCTCATGAG
481  ----+----+----+----+----+----+----+----+----+----+----+----+ +540
     CCGGGTGAACCAACTGCGGCTGATGGACCGGTTCATATTCTTCCGCCAGCTCGAGTACTC
      A  H  L  V  D  A  D  Y  L  A  K  Y  K  K  A  V  E  L  M  R

GGCCCTGCCGGCCGGCGACGACCCGCGCAACTTCGTACAGCAAGCGAAAGTGCACTGTGCGTA
541  ----+----+----+----+----+----+----+----+----+----+----+----+ +600
     CCGGGACGGCCGGCCGCTGCTGGGCGCGTTGAAGCATGTCGTTCGCTTCACGTGACACGCAT
      A  L  P  A  D  D  P  R  N  F  V  Q  Q  A  K  V  H  C  A  Y
```

FIGURE 10C

```
     TTGCGACGGCGTATGACCAAATCGGCTTCCCCGATCTCGAGATCCAGAACTC
601  ---------+---------+---------+---------+---------+  +660
     AACGCTGCCGCGCATACTGGTTTAGCCGAAGGGGCTAGAGCTCTAGGTGTTGAG
      C  D  G  A  Y  D  Q  I  G  F  P  D  L  E  I  Q  H  N  S

GTGGCTCTTCTTTCCTTGGCACCGGTTCTACCTCTACTCCAACGAGCGCATACTCGGGAA
661  ---------+---------+---------+---------+---------+---------+  +720
     CACCGAGAAGAAAGGAACCGTGGCCAAGATGGAGATGAGGTTGCTCGCGTATGAGCCCTT
      W  L  F  F  P  W  H  R  F  Y  L  Y  S  N  E  R  I  L  G  K

ACTTATCGGCGACGACACGTTCGCGCTGCCTTTCTGGAACTGGGACGCGCCGGGGGGCAT
721  ---------+---------+---------+---------+---------+---------+  +780
     TGAATAGCCGCTGCTGTGCAAGCGCGACGGAAAGACCCTTGACCCTGCGCGGCCCCCGTA
      L  I  G  D  D  T  F  A  L  P  F  W  N  W  D  A  P  G  G  M

GCAGTTCCCGTCTATCTACACAGACCCCTTCATCCTCGCTATATGACAAGCTGCGTGATGC
781  ---------+---------+---------+---------+---------+---------+  +840
     CGTCAAGGGCAGATAGATGTGTCTGGGAAGTAGGAGCGATATACTGTTCGACGCACTACG
      Q  F  P  S  I  Y  T  D  P  S  S  L  Y  D  K  L  R  D  A

GAAGCACCAGCCGCCGACTTTGATTGACCTCGACTACAATGGCACCGATCCTACCTTCTC
841  ---------+---------+---------+---------+---------+---------+  +900
     CTTCGTGGTCGGCGGCTGAAACTAACTGGAGCTGATGTTACCGTGGCTAGGATGGAAGAG
      K  H  Q  P  P  T  L  I  D  L  D  Y  N  G  T  D  P  T  F  S
```

FIGURE 10D

```
     CCCTGAAGAAGATTAACCACAACCTCGCCGTCATGTACCGACAGGTGATATCCAGTGG
901  ------+---------+---------+---------+---------+---------+  +960
     GGGACTTCTTGTCTAATTGGTGTTGGAGCGGCAGTACATGGCTGTCCACTATAGGTCACC
      P  E  E  Q  I  N  H  N  L  A  V  M  Y  R  Q  V  I  S  S  G

AAAGACGCCAGAGCTGTTTATGGGCTCAGCGTACCCGGTGACCAGCCTGACCCCGG
961  ------+---------+---------+---------+---------+---------+  +1020
     TTTCTGCGGTCTCGACAAATACCCGAGTCGCATGGGCCACTGGTCGGACTGGGGCC
      K  T  P  E  L  F  M  G  S  A  Y  R  A  G  D  Q  P  D  P  G

CGCAGGCTCTGTAGAGCAGAAGCCGCACGGCCCGGTGCATGTGTGGACAGGTGATCGCAA
1021 ------+---------+---------+---------+---------+---------+  +1080
     GCGTCCGAGACATCTCGTCTTCGGCGTGCCGGGCCACGTACACACCTGTCCACTAGCGTT
      A  G  S  V  E  Q  K  P  H  G  P  V  H  V  W  T  G  D  R  N

CCAGCCCAATCGGCGAAGACATGGGCACGCTCTACTCGGGCGTGGGACCCCGTCTTCTT
1081 ------+---------+---------+---------+---------+---------+  +1140
     GGTCGGGTTAGCGCTTCTGTACCCGTGCGAGATGAGCCCGCACCCTGGGGCAGAAGAA
      Q  P  N  R  E  D  M  G  T  L  Y  S  A  A  W  D  P  V  F  F

CGCACACCACGGCCAACATCGACCGCATGTGGTACGTGTGGAGGAACCTTGGGCGGCAAGCA
1141 ------+---------+---------+---------+---------+---------+  +1200
     GCGTGGTGGTGCCGTTGTAGCTGGCGTACACCATGCACACCTCCTTGGAACCGCCGTTCGT
      A  H  H  G  N  I  D  R  M  W  Y  V  W  R  N  L  G  G  K  H
```

FIGURE 10E

```
      CCGCAACTTCACCGACCCCGACTGGCTCAACGCGTCCTTCCTGTTCTATGATGAGAATGC
1201  ------------+---------+---------+---------+---------+---------+1260
      GGCGTTGAAGTGGCTGGGGCTGACCGAGTTGCGCAGGAAGGACAAGATACTACTCTTACG
       R  N  F  T  D  P  D  W  L  N  A  S  F  L  F  Y  D  E  N  A

GCAGCTCGTCCGTGTTAAAGTAAAAAGACTGCTTAGAGGCCGACGCAATGCGGTACACATA
1261  ------------+---------+---------+---------+---------+---------+1320
      CGTCGAGCAGGCACAATTTCATTTTCTGACGAATCTCCGGCTGCGTTACGCCATGTGTAT
       Q  L  V  R  V  K  V  K  D  C  L  E  A  D  A  M  R  Y  T  Y

CCAGGATGTAGAGATCCCGTGGCTCAAAGCAAAGCCGACGCCAAAGAGCGCCCTACAGAA
1321  ------------+---------+---------+---------+---------+---------+1380
      GGTCCTACATCTCTAGGGCACCGAGTTTCGTTTCGGCTGCGGTTTCTCCGGGATGTCTT
       Q  D  V  E  I  P  W  L  K  A  K  P  T  P  K  S  A  L  Q  K

GATAAAGAGCAAGGTATCGACGCTGAAGGCAACACCAAGGGGACGACGACTACCACAGC
1381  ------------+---------+---------+---------+---------+---------+1440
      CTATTTCTCGTTCCATAGCTGCGACTTCCGTTGGTTCCCCCTGCTGCTGATGGTGTCG
       I  K  S  K  V  S  T  L  K  A  T  P  R  G  T  T  T  T  T  A

AGAGACTACATTTCCGGTGGTGCTGGATAAGCCGGTTGAGTGCAACAGTGGCTAGACCGAA
1441  ------------+---------+---------+---------+---------+---------+1500
      TCTCTGATGTAAAGGCCACCACGACCTATTCGGCCACTCACGTTGTCACCGATCTGGCTT
       E  T  T  F  P  V  V  L  D  K  P  V  S  A  T  V  A  R  P  K
```

FIGURE 10F

```
      GGCCAGGAGGAGTGGGAAGGAGAAGGAGAAGAGGAGGAGGTGTTGGTGGTGGAGGGAAT
1501  ----+----+----+----+----+----+----+----+----+----+----+----  +1560
      CCGGTCCTCCTCACCCTTCCTCTTCCTTCTTCTCCTCCTCCACAACCACCACCTCCCTTA
       A  R  S  G  K  E  K  E  E  E  E  E  V  L  V  V  E  G  I

CGAGTTGGAGAAGGACGTGTTCGTGAAGTTTGATGTGTATATAAACTCGCCGGAGCACGA
1561  ----+----+----+----+----+----+----+----+----+----+----+----  +1620
      GCTCAACCTCTTCCTGCACAAGCACTTCAAACTACACATATATTTGAGCGGCCTCGTGCT
       E  L  E  K  D  V  F  V  K  F  D  V  Y  I  N  S  P  E  H  E

AGGGGTGGGCCGGAGGCCGAGTGAGTTCGCAGGAGCTTCGTCCACGTGCCACACAAGCA
1621  ----+----+----+----+----+----+----+----+----+----+----+----  +1680
      TCCCCACCCCGGCCTCCGCTCACTCAAGCGTCCCTCGAAGCAGGTGCACGGTGTGTTCGT
       G  V  G  P  E  A  S  E  F  A  G  S  F  V  H  V  P  H  K  H

CAAGAAGGCGAAGAAGGGCGAAGAGATGGCCAGGATGAACACAAGGCTTAAGCTCGGGAT
1681  ----+----+----+----+----+----+----+----+----+----+----+----  +1740
      GTTCTTCCGCTTCTTCCCGCTTCTCTACCGGTCCTACTTGTGTTCCGAATTCGAGCCCTA
       K  K  A  K  K  G  K  E  M  A  R  M  N  T  R  L  K  L  G  I

AACGGACCTGCTCGAGGACATCGGCGCTGAGGACGACGAGAGCGTGCTCATCACGCTCGT
1741  ----+----+----+----+----+----+----+----+----+----+----+----  +1800
      TTGCCTGGACGAGCTCCTGTAGCCGCGACTCCTGCTGCTCTCGCACGAGTAGTGCGAGCA
       T  D  L  L  E  D  I  G  A  E  D  D  E  S  V  L  I  T  L  V
```

FIGURE 10G

```
     GCCCAGGAGGCGGCAAGGGAATGGTGAAGGTTGGAGGGCTAAGGATTGATTTCTCCAAGTG
1801 ------+---------+---------+---------+---------+---------+1860
     CGGGTCCTCGCGCCGTTCCCTTACCACTTCCAACCTCCCGATTCCTAACTAAAGAGGTTCAC
      P  R  S  G  K  G  M  V  K  V  G  G  L  R  I  D  F  S  K  *

ATGAGCATATTGTGAAGAGAAAATTTGCATTTACCGCCCTATAGAATCGAAAAATTGCGT
1861 ------+---------+---------+---------+---------+---------+1920
     TACTCGTATAACACTTCTCTTTTAAACGTAAATGGCGGGATATCTTAGCTTTTTAACGCA
      *  A  Y  C  E  E  K  I  C  I  Y  R  P  I  E  S  K  N  C  V

ATATGTCCCATTATTGTTTTTTATTCTTCAAGCGTATTCAGAATAAGAGTTGCGTGCA
1921 ------+---------+---------+---------+---------+---------+1980
     TATACAGGGTAATAACAAAAAATAAGAAGTTCGCATAAGTCTTATTCTCAACGCACGT
      Y  V  P  L  L  F  F  F  K  R  I  Q  N  K  S  C  V  H

TGCACGGCATGCAGCCATGTTGTGTAGTCGATATGTGGGGTATGTTTGGATCAGGGATAA
1981 ------+---------+---------+---------+---------+---------+2040
     ACGTGCCGTACGTCGGTACAACACATCAGCTATACACCCCATACAAACCTAGTCCCTATT
      A  R  M  Q  P  C  C  C  S  R  Y  V  G  Y  V  W  I  R  D  N

TGATGTGAACTTTGAATTAATTATTACACTCTGAGAATAAATTAGAGAGTTTATTATGCA
2041 ------+---------+---------+---------+---------+---------+2100
     ACTACACTTGAAACTTAATTAATAATGTGAGACTCTTATTTAATCTCTCAAATAATACGT
      D  V  N  F  E  L  I  I  T  L  *  E  *  I  R  E  F  I  M  Q
```

FIGURE 10H

```
      AGTTGCTTGGTGTAATAGATATTCAACATTGTTCCTATACATCTTTTTGGAAGAAAA
2101 ----+---------+---------+---------+---------+---------+ 2160
      TCAACGAACCACATTATCTATAAGTTGTAACAAGGATATGTAGAAAAACCTTCTTTT
       V  A  W  C  N  R  Y  S  T  L  F  P  I  H  L  F  E  E  K

AAAAAAAAAAAAAAAATCGAT
2161 ----+---------+----- 2181
      TTTTTTTTTTTTTTTTAGCTA
       K  K  K  K  S
```

FIGURE 11A

```
     CACGCCACCCTCTCTCTCTCTCTGGTCTACTGAACAGTAATAGACATGTCCCT
                                                              +60
     GTGCGGTGGGAAGAGAGAGAGAGAGACCAGATGACTTGTCATTATCTGTACAGGGA
1
      T  P  P  F  S  L  S  L  V  Y  *  T  V  I  D  M  S  L

GCTGTTGAACTCTAGCTTCACCGGTGCTTCCTCTGCATGCCTCCTCCAACGGGAAAGGTC
                                                              +120
     CGACAACTTGAGATCGAAGTGGCCACGAAGGAGACGTACGGAGGAGGTTGCCCTTTCCAG
61
      L  L  N  S  F  T  G  A  S  S  A  C  L  L  Q  R  E  R  S

CCGCCGCCGCCGCCTCCACGTCCCTGGCGTGACATGCCGCCAGGCAGTAATGGTGACCG
                                                              +180
     GGCGGCGGCGGCGGAGGTGCAGGACCGCACTGTACGGCGGTCCCGTCATTACCACTGGC
121
      R  R  R  R  L  H  V  P  G  V  T  C  R  Q  G  S  N  G  D  R

CAGAGATGCCGCCCCCCAGCAGTCGCGCCGCTGCTGGATCGGCGGACATGCTGTT
                                                              +240
     GTCTCTACGGCGGGGGGTCGTCAGCGCGGCGACGACCTAGCCGCCGTGTACGACAA
181
      R  D  A  A  P  Q  Q  Q  S  P  P  L  L  D  R  R  D  M  L  L

GGGTTTAGGAGGGCTTTACGGCGTGACCGCAGGACCCAAGGTTCTGGCGGCCGATAAT
                                                              +300
     CCCAAATCCTCCCGAAATGCCGCACTGGCGTCCTGGGTTCCAAGACCGCCGGCTATTA
241
      G  L  G  G  L  Y  G  V  T  A  G  P  K  V  L  A  A  P  I  M
```

FIGURE 11B

```
    GCCGCGGATCTGTCCAAGTGTCTACCCTGCCACCGCCCCTGCCCCTCGACAACAAATGCTG
301 ------+---------+---------+---------+---------+---------+  +360
    CGGCGCCTAGACAGGTTCACGATGGGACGGTGGCCGTGGACGGGAGCTGTTGTTTACGAC
     P  P  D  L  S  K  C  Y  P  A  T  A  P  A  L  D  N  K  C  C

CCCGCCCTTACGACCCCGGAGACGATCTCGGAGTACAGCTTCCCTGCTACGCCCCTCCG
361 ------+---------+---------+---------+---------+---------+  +420
    GGGCGGGAATGCTGGGGCCTCTGCTAGAGCCTCATGTCGAAGGGACGATGCGGGGAGGC
     P  P  Y  D  P  G  E  T  I  S  E  Y  S  F  P  A  T  P  L  R

GGTGCGGCGGGGCCGGGCCCCATATCGTGAAGGACGATCAGGAGTATATGGACAAGTACAAGGA
421 ------+---------+---------+---------+---------+---------+  +480
    CCACGCCGCCCGGCCCGGGGTATAGCACTTCCTGCTAGTCCTCATATACCTGTTCATGTTCCT
     V  R  P  A  H  I  V  K  D  D  Q  E  Y  M  D  K  Y  K  E

GGCAGTGAGGAGGATGAAGAATCTGCCGGCAGACCCCCTTGGAACTACTACCAGCAGGC
481 ------+---------+---------+---------+---------+---------+  +540
    CCGTCACTCCTCCTACTTCTTAGACGGCCGTCTGGGGAACCTTGATGATGGTCGTCCG
     A  V  R  R  M  K  N  L  P  A  D  H  P  W  N  Y  Y  Q  Q  A

GAACATCCACTGCCAGTATTGCAACTACGCCTACCACCAGCAAAATACCGACGACGTGCC
541 ------+---------+---------+---------+---------+---------+  +600
    CTTGTAGGTGACGGTCATAACGTTGATGCGGATGGTGGTCGTTTTATGGCTGCTGCACGG
     N  I  H  C  Q  Y  C  N  Y  A  Y  H  Q  Q  N  T  D  D  V  P
```

FIGURE 11C

```
     CATCCAGTCCACTTCAGCTGGATCTTCCTCCCATGGCACCGCTACTACCTTCCACTTCTA
601  ------+---------+---------+---------+---------+---------+660
     GTAGGTCCAGGTGAAGTCGACCTAGAAGGAGGGTACCGTGGCGATGATGGAGGTGAAGAT
      I  Q  V  H  F  S  W  I  F  L  P  W  H  R  Y  Y  L  H  F  Y

CGAAAGGATCCTCGGCAAGCTCATCGACGACGACACCTTCACCATTCCCATTCTGGAACTG
661  ------+---------+---------+---------+---------+---------+720
     GCTTTCCTAGGAGCCGTTCGAGTAGCTGCTGCTGTGGAAGTGGTAAGGGTAAGACCTTGAC
      E  R  I  L  G  K  L  I  D  D  D  T  F  T  I  P  F  W  N  W

GGACACCAAGGACGGGATGACGTTCCCCGCCATCTTCCAGGATGCGGCATCCCCGCTGTA
721  ------+---------+---------+---------+---------+---------+780
     CCTGTGGTTCCTGCCCTACTGCAAGGGGCGGTAGAAGGTCCTACGCCGTAGGGGCGACAT
      D  T  K  D  G  M  T  F  P  A  I  F  Q  D  A  A  S  P  L  Y

CGACCCGAGACGCGACCAACGCCAGTGCTGGTTGCGCAGTTCCTGCCGTTCTAGGAGCTGGAGTTCATGCG
781  ------+---------+---------+---------+---------+---------+840
     GCTGGGCTCTGCGCTGGTTGCGGTCACGACCAACGCGTCAAGGACGGCAAGATCCTGACCTCAAGTACGC
      D  P  R  R  D  Q  R  H  V  K  D  G  K  I  L  D  L  K  Y  A

CTACACCGAAAACACTGCATCCGACAGCGAGATCATACGGGAGAACCTCTGCTTCATACA
841  ------+---------+---------+---------+---------+---------+900
     GATGTGGCTTTTGTGACGTAGGCTGTCGCTCTAGTATGCCCTCTTGGAGACGAAGTATGT
      Y  T  E  N  T  A  S  D  S  E  I  I  R  E  N  L  C  F  I  Q
```

FIGURE 11D

```
     GAAGACGTTCAAGCACAGCCTGTCGCTGGCGGAACTGTTCATGGGGGATCCCGTGCGCGC
901  ------+---------+---------+---------+---------+---------+  +960
     CTTCTGCAAGTTCGTGTCGGACAGCGACCGCCTTGACAAGTACCCCCTAGGGCACGCGCG
      K  T  F  K  H  S  L  S  L  A  E  L  F  M  G  D  P  V  R  A

GGGGGAGAAGGAGATCCAGGAGGCTAATGGGCAGATGGAAGTCATCCACAATGCGGCGCA
961  ------+---------+---------+---------+---------+---------+  +1020
     CCCCCTCTTCCTCTAGGTCCTCCGATTACCCGTCTACCTTCAGTAGGTGTTACGCCGCGT
      G  E  K  E  I  Q  E  A  N  G  Q  M  E  V  I  H  N  A  A  H

CATGTGGGTCGGAGAGCCGGACGGATACAAGGAAAACATGGGGGACTTCTCCACCGCCGC
1021 ------+---------+---------+---------+---------+---------+  +1080
     GTACACCCAGCCTCTCGGCCTGCCTATGTTCCTTTTGTACCCCCTGAAGAGGTGGCGGCG
      M  W  V  G  E  P  D  G  Y  K  E  N  M  G  D  F  S  T  A  A

CCGCGATTCTGTTTTCTTCTGCCACCATTCCAATGTCGACCGGCATGTGGGACATCTACCG
1081 ------+---------+---------+---------+---------+---------+  +1140
     GGCGCTAAGACAAAAGAAGACGGTGGTAAGGTTACAGCTGGCCGTACACCCTGTAGATGGC
      R  D  S  V  F  F  C  H  H  S  N  V  D  R  M  W  D  I  Y  R

CAACCTCCGGCAACCGGTTGGCGCAGCTCAAGCTTCTGTTGCTGACAACGACTGGTTGGACAGCACCTTCCT
1141 ------+---------+---------+---------+---------+---------+  +1200
     GTTGGAGGCCGTTGGCCAACCGCGTCGAGTTCGAAGACAACGACTGTTGCTGACCAACCTGTCGTGGAAGGA
      N  L  R  G  N  R  V  E  F  F  E  D  N  D  W  L  D  S  T  F  L
```

FIGURE 11E

```
      CTTCCACGAGAACGAACAGCTCGTCAAAGTCAAGATGAGCGACTGCCTCAACCCGAC
1201  ----+----+----+----+----+----+----+----+----+----+----+----+ +1260
      GAAGGTGCTGCTCTTGCTTGTCGAGCAGTTTCAGTTCTACTCGCTGACGGAGTTGGGCTG
       F  H  D  E  N  E  Q  L  V  K  V  K  M  S  D  C  L  N  P  T

CAAGCTTCGGTACACGTTCGAGCAAGTTCCCCTGGCTGGGCAAAATCAATTGCCA
1261  ----+----+----+----+----+----+----+----+----+----+----+----+ +1320
      GTTCGAAGCCATGTGCAAGCTCGTTCAAGGGGAGGTACCGACCCGTTTAGTTAACGGT
       K  L  R  Y  T  F  E  Q  V  P  L  P  W  L  G  K  I  N  C  Q

GAAGACGGCAGAGACGAAGTCCAAGGCCAAGTCCAAGGCCACTGAGCTGTCGCTGACGCGTGAACGA
1321  ----+----+----+----+----+----+----+----+----+----+----+----+ +1380
      CTTCTGCCGTCTCTGCTTCAGGTTCCGGTTCAGGTTCCGGTGACTCGACAGGCGACTGCGCACTTGCT
       K  T  A  E  T  K  S  K  A  T  T  E  L  S  L  T  R  V  N  E

ATTCGGGACGACGCCCAGGCACTCGACGCGAGCAACCCGCTGCGGGTGATCGTGGCAAG
1381  ----+----+----+----+----+----+----+----+----+----+----+----+ +1440
      TAAGCCCTGCTGCGGGTCCGTGAGCTGCGCTCGTTGGGCGACGCCCACTAGCACCGTTC
       F  G  T  T  A  Q  A  L  D  A  S  N  P  L  R  V  I  V  A  R

GCCGAAGAAGAACCGCAAGAAGAAGAAGAAGCAAGAGAAGGTGGGGGTGATTCAGATCAA
1441  ----+----+----+----+----+----+----+----+----+----+----+----+ +1500
      CGGCTTCTTCTTGGCGTTCTTCTTCTTCGTTCTCTTCCACCCCACTAAGTCTAGTT
       P  K  K  N  R  K  K  K  E  K  Q  E  K  V  G  V  I  Q  I  K
```

FIGURE 11F

```
     GGATATTAAGGTGACCACCAACGAGACAGCTCGCTTCGACGTCTATGTGCGGTTCCTTA
1501 ------+---------+---------+---------+---------+---------+ +1560
     CCTATAATTCCACTGGTGGTTGCTCTGTCGAGCGAAGCTGCAGATACACGCCAAGGAAT
      D  I  K  V  T  T  N  E  T  A  R  F  D  V  Y  V  A  V  P  Y

CGGTGACCTCGCGGACCCGACTACGGCGAGTTCGCGGGCAGCTACGTGAGGCTGGCGCA
1561 ------+---------+---------+---------+---------+---------+ +1620
     GCCACTGGAGCGCCTGGGCTGATGCCGCTCAAGCGCCCGTCGATGCACTCCGACCGCGT
      G  D  L  A  G  P  D  Y  G  E  F  A  G  S  Y  V  R  L  A  H

TAGGATGAAGGGAAGCGACGGGACCGAAAAGCAGGCCCCAAGAAGAAGGGAAAAACTCAA
1621 ------+---------+---------+---------+---------+---------+ +1680
     ATCCTACTTCCCTTCGCTGCCGCTGGCTTTTCGTCCCGGGTTCTTCTTCCCTTTTGAGTT
      R  M  K  G  S  D  G  T  E  K  Q  G  P  K  K  K  G  K  L  K

GCTGGGTATTACGCCGCTGGAGGACATCGATGCTGAGGACGCCGACAAGTTGGTGGT
1681 ------+---------+---------+---------+---------+---------+ +1740
     CGACCCATAATGCGGCGACCTCCTGTAGCTACGACTCCTGCGGCTGTTCAACCACCA
      L  G  I  T  P  L  E  D  I  D  A  E  D  A  D  K  L  V  V

CACCCTGGTTCTCCGCACTGGGAGCGTCACCGTGGGGGAGTTTCCATCAATCTCCTGCA
1741 ------+---------+---------+---------+---------+---------+ +1800
     GTGGGACCAAGAGGCGTGACCCTCGCAGTGGCACCCCCTCAAAGGTAGTTAGAGGACGT
      T  L  V  R  T  G  S  V  T  V  G  G  V  S  I  N  L  L  Q
```

FIGURE 11G

```
1801 GACAGATTCTACCGCCGCCATCTAAATGATGGCCCTCGGATCACAGCTTCTCCCGCTTAA +1860
     CTGTCTAAGATGGCGGCGGTAGATTTACTACCGGAGCCTAGTGTCGAAGAGGGCGAATT
      T  D  S  T  A  A  I  *

1861 GTTGGAGTGATCGATTACTGGTGCTGCTTTTCTTCCCTCCCGTCGTTCTTGCTATCTTCTT +1920
     CAACCTCACTAGCTAATGACCACGACGAAAGAAGGAGGACAGCAAGAACGATAGAAGAA

1921 GATCTGGAACGATCCTTCAATAATTAGGGCATGACAGTAGTCGTCGCCCGATCCCATATG +1980
     CTAGACCTTGCTAGGAAGTTATTAATCCCGTACTGTCATCAGCAGCGGGCTAGGGTATAC

1981 TACGTGTGTTGGTCTCAACAGCTGTGTCGACGTTATGGTGTGACTATATATTTTATTGC +2040
     ATGCACAACCAGAGTTGTCGACACAGCTGCAATACCACACTGATATATAAAATAACG

2041 GGTCATCCCTTGTTTCTTTCTTAAAAAAAAAAAAAAAAA 2078
     CCAGTAGGAACAAAGAAAGAATTTTTTTTTTTTTTT
```

FIGURE 12A

```
1   AATGTGGATCGGATGTGGACGGTGTGGAAGAAGCTGCACGGCGACAAGCCGGAGTTCGTC
    ----+----+----+----+----+----+----+----+----+----+----+----+   +60
    TTACACCTAGCCTACACCTGCCACACCTTCTTCGACGTGCCGCTGTTCGGCCTCAAGCAG
     N  V  D  R  M  W  T  V  W  K  K  L  H  G  D  K  P  E  F  V

61  GACCAGGAGTGGCTCGAGTCTGAATTCACCTTCTACGACGAGAATGTGCGCCTGCGCAGG
    ----+----+----+----+----+----+----+----+----+----+----+----+   +120
    CTGGTCCTCACCGAGCTCAGACTTAAGTGGAAGATGCTGCTCTTACACGCGGACGCGTCC
     D  Q  E  W  L  E  S  E  F  T  F  Y  D  E  N  V  R  L  R  R

121 ATCAAGGTGCGCGACGTGTTGAACATAGACAAACTCAGGTACCGGTACGAAGACATCGAC
    ----+----+----+----+----+----+----+----+----+----+----+----+   +180
    TAGTTCCACGCGCTGCACAACTTGTATCTGTTTGAGTCCATGGCCATGCTTCTGTAGCTG
     I  K  V  R  D  V  L  N  I  D  K  L  R  Y  R  Y  E  D  I  D

181 ATGCCATGGCTCGCTGCGAGCGACGTGCAGGTTCGGAAGGCAAGTGGGATTCTAGCGCCGGCGCTGTAT
    ----+----+----+----+----+----+----+----+----+----+----+----+   +240
    TACGGTACCGAGCGACGCTCGCTGCACGTCCAAGCCTTCCGTTCACCCTAAGATCGCGGCCGCGACATA
     M  P  W  L  A  A  R  P  K  P  S  V  H  P  K  I  A  R  D  I

241 TTGAAGAAGCGTAATGGCGAAGGCGTACTGAGAATGCCCGGCGAAACGGATCGTTCACAA
    ----+----+----+----+----+----+----+----+----+----+----+----+   +300
    AACTTCTTCGCATTACCGCTTCCGCATGACTCTTACGGGCCGCTTTGCCTAGCAAGTGTT
     L  K  K  R  N  G  E  G  V  L  R  M  P  G  E  T  D  R  S  Q
```

FIGURE 12B

```
     CTCTCCGAAGATGGTAGCTGGACACTGGACAAGAGCATCACCGTGAGGGTTGACAGGCCA
301  ------+---------+---------+---------+---------+---------+   +360
     GAGAGGCTTCTACCATCGACCTGTGACCTGTTCTCGTAGTGGCACTCCCAACTGTCCGGT
      L  S  E  D  G  S  W  T  L  D  K  S  I  T  V  R  V  D  R  P

AGGATCAACAGGACAGGGCAAGAAAAAGAGGAAGAGAGAGATCTTATTGGTCTACGGA
361  ------+---------+---------+---------+---------+---------+   +420
     TCCTAGTTGTCCTGTCCCGTTCTTTTTCTCCTTCTCCTCTAGAATAACCAGATGCCT
      R  I  N  R  T  G  Q  E  K  E  E  E  E  I  L  L  V  Y  G

ATCGATACTAAGAGAAGCAGATTCGTCAAATTCGATGTGTTCATCAACGTCGTCGACGAA
421  ------+---------+---------+---------+---------+---------+   +480
     TAGCTATGATTCTCTTCGTCTAAGCAGTTTAAGCTACACAAGTAGTTGCAGCAGCTGCTT
      I  D  T  K  R  S  R  F  V  K  F  D  V  F  I  N  V  V  D  E

ACCGTGCTGAACCCCAAAGTCGAGGGAGTTCGCAGGGACCCTTCGTCAATCTCCACCACGTC
481  ------+---------+---------+---------+---------+---------+   +540
     TGGCACGACTTGGGTTTCAGCTCCCTCAAGCGTCCCTGGAAGCAGTTAGAGGTGGTGCAG
      T  V  L  N  P  K  S  R  E  F  A  G  T  F  V  N  L  H  H  V

TCGAGGACGAAAAGCCATGAGGATGGGCGTGGGGTTCGAAGATGAAAAGCCACCTTAAG
541  ------+---------+---------+---------+---------+---------+   +600
     AGCTCCTGCTTTTCGGTACTCCTACCGCCGCACCCAAGCTTCTACTTTTCGGTGGAATTC
      S  R  T  K  S  H  E  D  G  G  V  G  S  K  M  K  S  H  L  K
```

FIGURE 12C

```
     CTCGGTATATCGGAGCCTTTTGGAAGACCTCGAGGCAGACGAAGATGATTGCATCTGGGTG
601  ------------+---------+---------+---------+---------+---------+  +660
     GAGCCATATAGCCTCGGAAAACCTTCTGGAGCTCCGTCTGCTTCTACTAACGTAGACCCAC
      L  G  I  S  E  L  L  E  D  L  E  A  D  E  D  D  C  I  W  V

ACACTGGTGCCAAGAGGCGGCACGGGGTCAACACCACCGTAGACGGGGTCCGGATCGAC
661  ------------+---------+---------+---------+---------+---------+  +720
     TGTGACCACGGTTCTCCGCCGTGCCCCAGTTGTGGTGGCATCTGCCGCAGGCCTAGCTG
      T  L  V  P  R  G  G  T  G  V  N  T  T  V  D  G  V  R  I  D

TACATGAAGTAGTGAACCGGACGCCGCTCCTCCCCATCAGAAGTGGTATAATAT
721  ------------+---------+---------+---------+---------+---------+  +780
     ATGTACTTCATCACTTGGCCTGCGGAGGGGGTAGTCTTCACCATATTATA
      Y  M  K  *

TTATATTGGATCGAGGCTCGTGGTATCTTTTGATAAGAGTAAGTTCCATAAATTTAGAAG
781  ------------+---------+---------+---------+---------+---------+  +840
     AATATAACCTAGCTCCGAGCACCATAGAAAACTATTCTCATTCAAGGTATTTAAATCTTC

AAGAATCATGTTCTTTATTTATATTAAATCAATGTGATTTGTCCAAAAAAAAAAAAAA
841  ------------+---------+---------+---------+---------+---------+  +900
     TTCTTAGTACAAGAAATAAATATAATTTAGTTACACTAAACAGGTTTTTTTTTTTTTT
```

FIGURE 13A

```
    TGCACTGTGCGTATTGCCGACGGCGCGTATGACCAAATCGGCTTCCCCGATCTCGAGATCC
1   ------+---------+---------+---------+---------+---------+  60
    ACGTGACACGCATAACGGCTGCCGCGCATACTGGTTTAGCCGAAGGGGCTAGAGCTCTAGG
     H  C  A  Y  C  D  G  A  Y  D  Q  I  G  F  P  D  L  E  I  Q

AGATCCACAACTCGTGGCTCTTCTTTCCTTGGCACCGGTTCTACCTCTACTCCAACGAGC
61  ------+---------+---------+---------+---------+---------+ 120
    TCTAGGTGTTGAGCACCGAGAGAAGAAAGGAACCGTGGCCAAGATGGAGATGAGGTTGCTCG
     I  H  N  S  W  L  F  F  P  W  H  R  F  Y  L  Y  S  N  E  R

GCATACTCGGGAAACTTATCGGCGACCCTGCCCTTTCTGGAACTGGGACG
121 ------+---------+---------+---------+---------+---------+ 180
    CGTATGAGCCCTTTGAATAGCCGCTGTGCAAGCGCGACGGAAAGACCTTGACCCTGC
     I  L  G  K  L  I  G  D  D  T  F  A  L  P  F  W  N  D  A

CGCCGGGGGCATGCAGTTCCCGTCAAGGGCAGACCCAGCCCGACTTTGATTGACCTCGCTATATGACA
181 ------+---------+---------+---------+---------+---------+ 240
    GCGGCCCCCGTACGTCAAGGGCAGTTCCCGTCTGGGAAGTAGGAGCGATATACTGT
     P  G  G  M  Q  F  P  S  I  Y  T  D  P  S  S  S  L  Y  D  K

AGCTGCCTGATGCCGAAGCACCAGCCCGCCGACTTTGATTGACCTACAATGGCACCG
241 ------+---------+---------+---------+---------+---------+ 300
    TCGACGGACTACGCTTCGTGGTCGGGCTGAAACTAACTGGAGCTGATGTTACCGTGGC
     L  R  D  A  K  H  Q  P  P  T  L  I  D  L  D  Y  N  G  T  D
```

FIGURE 13B

```
     ATCCTACCTTCTCCCCTGAAGAACAGATTAACCACAACCTCGCCGTCATGTACCGACAGG
301  ------+---------+---------+---------+---------+---------+  +360
     TAGGATGGAAGAGGGACTTCTTGTCTAATTGGTGTTGGAGGCGCAGTACATGGCTGTCC
        P  T  F  S  P  E  E  Q  I  N  H  N  L  A  V  M  Y  R  Q  V

TGATATCCAGTGGAAAGACACCAGAGCTGTTTATGGGCTCAGCGTACCGCGCGGTGACC
361  ------+---------+---------+---------+---------+---------+  +420
     ACTATAGGTCACCTTTCTGTGGTCTCGACAAATACCCGAGTCGCATGGCGGCCACTGG
        I  S  G  K  T  P  E  L  F  M  G  S  A  Y  R  A  G  D  Q

AGCCTGACCCCGGCGCAGGCTCTGTAGAGCAGAAGCCGGTGCATGTGTGGA
421  ------+---------+---------+---------+---------+---------+  +480
     TCGGACTGGGGCCGCGTCCGAGACATCTCGTCTTCGGCCACGTACACACCT
        P  D  P  G  A  G  S  V  E  Q  K  P  H  G  P  V  H  V  W  T

CAGGTGATCGCAACCAGCCCCAATCGCGAAGACATGGGCACGCTCTACTCGGCGGTGGG
481  ------+---------+---------+---------+---------+---------+  +540
     GTCCACTAGCGTTGGTCGGGTTAGCGCTTCGTGCCGAGATGAGCCGCCACCC
        G  D  R  N  Q  P  N  R  E  D  M  G  T  L  Y  S  A  A  W  D

ACCCCGTCTTCTTCGCACACCACGGCAACATCGACCGCATGTGGTACGTGTGGAGGAACC
541  ------+---------+---------+---------+---------+---------+  +600
     TGGGGCAGAAGAAGCGTGTGGTGCCGTTGTAGCTGGCGTACACCATGCACACCTCCTTGG
        P  V  F  F  A  H  H  G  N  I  D  R  M  W  Y  V  W  R  N  L
```

FIGURE 13C

```
     TTGGCGGCAAGCACCGCAACTTCACCGACCCCGACTGGCTCAACGCGTCCTTCCTGTTCT
601  ------+---------+---------+---------+---------+---------+  +660
     AACCGCCGTTCGTGGCGTTGAAGTGGCTGGGGCTGACCGAGTTGCGCAGGAAGGACAAGA
      G  G  K  H  R  N  F  T  D  P  D  W  L  N  A  S  F  L  F  Y

ATGATGAGAATGCGCAGTCGTCGTCCGTGTTAAAGTAAAAGACTGCTTAGAGGCCGACGCAA
661  ------+---------+---------+---------+---------+---------+  +720
     TACTACTCTTACGCGTCGAGCAGGCACAATTTCATTTTCTGACGAATCTCCGGCTGCGTT
      D  E  N  A  Q  L  V  R  V  K  V  K  D  C  L  E  A  D  A  M

TGCGGGTACACATACCAGGATGTAGAGATCCCGTGGCTCAAAGCAAAGCCGACGCCAAAGA
721  ------+---------+---------+---------+---------+---------+  +780
     ACGGCCATGTGTATGGTCCTACATCTCTAGGGCACCGAGTTTCGTTTCGGCTGCGGTTTCT
      R  Y  T  Y  Q  D  V  E  I  P  W  L  K  A  K  P  T  P  K  S

GCGCCCTACAGAAGATAAAGAGCAAGGTATCGACGCTGAAGGCAACACCAAGGGGACGA
781  ------+---------+---------+---------+---------+---------+  +840
     CGCGGGATGTCTTCTATTTCTCGTTCCATAGCTGCGACTTCCGTTGTTCCCCCTGCT
      A  L  Q  K  I  K  S  K  V  S  T  L  K  A  T  P  R  G  T  T

CGACTACCACAGCAGAGACTACATTTCCGGTGGTCTGGATAAGCCGGTGAGTGCAACAG
841  ------+---------+---------+---------+---------+---------+  +900
     GCTGATGGTGTCGTCTCTGATGTAAAGGCCACCAGACCTATTCGGCCACTCACGTTGTC
      T  T  A  E  T  T  F  P  V  V  L  D  K  P  V  S  A  T  V
```

FIGURE 13D

```
     TGGCTAGACCGAAGGCCAGGAGGAGTGGGAGGAAGAAGAGAGGAGGAGGTGTTGG
901  ------+---------+---------+---------+---------+---------+  +960
     ACCGATCTGGCTTCCGGTCCTCCTCACCCTTCCTTCTTCTCCTCCTCCACAACC
      A  R  P  K  A  R  R  S  G  K  E  K  E  E  E  E  V  L  V

TGGTGGAGGGAATCGAGTTGGAGAAGGACGTGTTCGTGAAGTTTGATGTGTATATAAACT
961  ------+---------+---------+---------+---------+---------+  +1020
     ACCACCTCCCTTAGCTCAACCTCTTCCTGCACAAGCACTTCAAACTACACATATATTTGA
      V  E  G  I  E  L  E  K  D  V  F  V  K  F  D  V  Y  I  N  S

CGCCGGAGCACGAAGGGGTGGGCCGGAGGCGAGTGAGTTCGCAGGGAGCTTCGTCCACG
1021 ------+---------+---------+---------+---------+---------+  +1080
     GCGGCCTCGTGCTTCCCCACCCGGCCTCCGCTCACTCAAGCGTCCCTCGAAGCAGGTGC
      P  E  H  E  G  V  G  P  E  A  S  E  F  A  G  S  F  V  H  V

TGCCACACAAGCACAAGAAGAAGGGGAAGAAGGGGAAGAGATGGCCAGGATGAACACAAGGC
1081 ------+---------+---------+---------+---------+---------+  +1140
     ACGGTGTGTTCGTGTTCTTCTTCCCCTTCTTCCCCTTCTCTACCGGTCCTACTTGTGTTCCG
      P  H  K  H  K  K  A  K  K  G  K  E  M  A  R  M  N  T  R  L

TTAAGCTCGGGATAACGGACCTGCTCGAGGACATCGGCGCTGAGGACGACGAGAGCGTGC
1141 ------+---------+---------+---------+---------+---------+  +1200
     AATTCGAGCCCTATTGCCTGGACGAGCTCCTGTAGCCGCGACTCCTGCTGCTCTCGCACG
      K  L  G  I  T  D  L  L  E  D  I  G  A  E  D  D  E  S  V  L
```

FIGURE 13E

```
      TCATCACGCTCGTGCCCAGGAGCGGCAAGGGAATGGTGAAGGTTGGAGGGCTAAGGATTG
1201  ------+---------+---------+---------+---------+---------+  +1260
      AGTAGTGCGAGCACGGGTCCTCGCCGTTCCCTTACCACTTCCAACCTCCCGATTCCTAAC
       I  T  L  V  P  R  S  G  K  G  M  V  K  V  G  G  L  R  I  D

ATTTCTCCAAGTGATGAGCATATTGTGAAGAGAAATTTGCATTTACCGCCCTATAGAAT
1261  ------+---------+---------+---------+---------+---------+  +1320
      TAAAGAGGTTCACTACTCGTATAACACTTCTCTTTAAACGTAAATGGCGGGATATCTTA
       F  S  K  *  A  Y  C  E  E  K  I  C  I  Y  R  P  I  E  S

CGAAAAAATTGCGTATATGTCCCATTATTGTTTTTTTTATTCTTCAAGCGTATTCAGAATA
1321  ------+---------+---------+---------+---------+---------+  +1380
      GCTTTTTTAACGCATATACAGGGTAATAACAAAAAAAATAAGAAGTTCGCATAAGTCTTAT
       K  N  C  V  Y  V  P  L  L  F  F  F  L  F  F  K  R  I  Q  N  K

AGAGTTGCGTGCATGCACGCAGCCATGTGTTGTAGTCGATATGTGGGGTATGTTT
1381  ------+---------+---------+---------+---------+---------+  +1440
      TCTCAACGCACGTACGTGCGTACGTCGGTACAACACATCAGCTATACACCCATACAAA
       S  C  V  H  A  R  M  Q  P  C  C  C  S  R  Y  V  G  Y  V  W

GGATCAGGGATAATGATGTGAACTTTGAATTAATTATTACACTCTGAGAATAAATTAGAG
1441  ------+---------+---------+---------+---------+---------+  +1500
      CCTAGTCCCTATTACTACTACACTTGAAACTTAATTAATAATGTGAGACTCTTATTAATCTC
       I  R  D  N  D  V  N  F  E  L  I  T  I  *  E  *  I  R  E

AGTTTATTATGCAAAAAAAAAA
1501  ------+---------+---  1522
      TCAAATAATACGTTTTTTTTTT
       F  I  M  Q  K  K
```

FIGURE 14A

```
    ACAACAAACCAGTGCCTGGTTTAGGTGTATTCACTATGGCCACCCTCTCTAAACTAGCTT
1   ------+---------+---------+---------+---------+---------+   60
    TGTTGTTTGGTCACGGACCAAATCCACATAAGTGATACCGGTGGGAGAGATTTGATCGAA
     N  K  P  V  P  G  L  G  V  F  T  M  A  T  L  S  K  L  A  S

CCCCAACCAATAACACCTCCACTCTCCCCGCTCCTCCTTTGCATGCTCCTTCTCTCACC
61  ------+---------+---------+---------+---------+---------+  120
    GGGGTTGGTTATTGTGGAGGTGAGAGGGCGAGGAGGAAACGTACGAGGAAGAGAGTGG
     P  T  N  N  T  S  T  L  P  A  P  S  F  A  C  S  F  S  H  Q

AAAAGCTTCACCACCTTCCCTCCCCTGTAGGGTCCCAAACCACCCGTCATAAGA
121 ------+---------+---------+---------+---------+---------+  180
    TTTTCGAAGTGGTGGAAGGGAGGGGACATCCCAGGTTTGTGGGGCAGTATTCT
     K  L  H  H  H  L  P  L  P  C  R  G  P  K  P  P  R  H  K  I

TCTCATGCAAATCTAAGGAGCAACAAGAGAATGCCGACAAGCCTGCGGGGCCGCATCGACC
181 ------+---------+---------+---------+---------+---------+  240
    AGAGTACGTTTAGATTCCTCGTTGTTCTCTTACGGCTGTTCGGACGCCCGGTAGCTGG
     S  C  K  S  K  E  Q  Q  E  N  A  D  K  P  A  G  R  I  D  R

GCCGCGACCTACTCCTGGGCCTTTACGGTGCCACCACTGGGCTCGGCCTCA
241 ------+---------+---------+---------+---------+---------+  300
    CGGCGCTGGATGAGGACCCGCGAGCCCGGCGAAATGCCACGGTGGTGACCCGAGCCGGAGT
     R  D  L  L  L  G  G  L  G  G  L  Y  G  A  T  T  G  L  G  L  N
```

FIGURE 14B

```
301 ACCGTGGAGCGGCCGCCGCCCCTATCCTGGCTCCCGACCTCTCAACTTGTGGGCCCTG      +360
    ----+----+----+----+----+----+----+----+----+----+----+----+
    TGGCAGCTCGCCGGCGGCGGGGATAGGACCGAGGGCTGGAGAGTTGAACACCCGGCGAC
     R  R  A  A  A  A  P  I  L  A  P  D  L  S  T  C  G  P  P  A

361 CCGACCTCCCTGCCTCCCGACCCGACCGACAGTTGCTGCCCGCCATACCACCATCA        +420
    ----+----+----+----+----+----+----+----+----+----+----+----+
    GGCTGGAGGGACGGAGGGCTGGGCTGGCTGTCAACGACGGGCGGTATGGTTGGTAGT
     D  L  P  A  S  A  R  P  T  V  C  C  P  P  Y  Q  S  T  I  I

421 TCGTCTTTCAAGCTCCCCGCGATCTGCTCCGCTTCCGCCTCGCCCCACTTGG             +480
    ----+----+----+----+----+----+----+----+----+----+----+----+
    AGCAGAAAGTTCGAGGGGCGCTAGACGAGGCGAAGGCGGAGCGGGGTGAACC
     V  F  K  L  P  P  R  S  A  P  L  R  V  R  P  A  A  H  L  V

481 TTGACGCCGACTACCTGGCCAAGTATAAGAAGGCGGTTCATATTCTTCCGCCAGTACTCCCGGACGGCC  +540
    ----+----+----+----+----+----+----+----+----+----+----+----+
    AACTGCGGCTGATGGACCGGTTCATATTCTTCCGCCAAGTATAAGAAGGCGGTCATGAGGGCCCTGCCGG
     D  A  D  Y  L  A  K  Y  K  K  A  V  E  L  M  R  A  L  P  A

541 CCGACGACCCGCGCAACTTCGTACAGCAAGCGAAAGTGCACTGTGCGTACTGCGACGGCG      +600
    ----+----+----+----+----+----+----+----+----+----+----+----+
    GGCTGCTGGGCGCGTTGAAGCATGTCGTTCGCTTTCACGTGACACGCATGACGCTGCCGC
     D  D  P  R  N  F  V  Q  Q  A  K  V  H  C  A  Y  C  D  G  A
```

FIGURE 14C

```
     CGTACGACCAAATCGGCTTCCCCGATCTCGAGATCCAGATCCACAACTCGTGGCTCTTCT
601  ------+---------+---------+---------+---------+---------+  +660
     GCATGCTGGTTTAGCCGAAGGGGCTAGAGCTCTAGGTCTAGGTGTTGAGCACCGAGAAGA
      Y  D  Q  I  G  F  P  D  L  E  I  Q  I  H  N  S  W  L  F  F

TTCCTTGGCACCGGTTCTACCTCTACTTCAACGAGCGCATACTCGGGAAACTTATCGGTG
661  ------+---------+---------+---------+---------+---------+  +720
     AAGGAACCGTGGCCAAGATGGAGATGAAGTTGCTCGCGTATGAGCCCTTTGAATAGCCAC
      P  W  H  R  F  Y  L  Y  F  N  E  R  I  L  G  K  L  I  G  D

ACGACACGTTCGCGCTGCCTTTCTGGAACTGGGACGCGCCGGGGCATGCAGTTCCCGT
721  ------+---------+---------+---------+---------+---------+  +780
     TGCTGTGCAAGCGCGACGGAAAGACCCTTGACCCTGCGCGGCCCCCGTACGTCAAGGGCA
      D  T  F  A  L  P  F  W  N  W  D  A  P  G  G  M  Q  F  P  S

CTATCTACACAGACCCCTTCATCCTCGCTATATGACAAGCTGCGTGATGCGAAGCACCAGC
781  ------+---------+---------+---------+---------+---------+  +840
     GATAGATGTGTCTGGGAAGTAGGAGCGATATACTGTTCGACGCACTACGCTTCGTGGTCG
      I  Y  T  D  P  S  S  L  Y  D  K  L  R  D  A  K  H  Q  P

CGCCGACTTTGATTGACCTCGACTACAATGGCACA
841  ------+---------+---------+-----  875
     GCGGCTGAAACTAACTGGAGCTGATGTTACCGTGT
      P  T  L  I  D  L  D  Y  N  G  T
```

FIGURE 15A

```
    GACCACCCATAGATGATGGCTTCTCTCGCCTTGTCTAGTCTTCCCACCTCCACCACAACC
1   ------+---------+---------+---------+---------+---------+   60
    CTGGTGGGTATCTACTACCGAAGAGAGAGCGGAACAGATCAGAAGGGTGGAGGTGGTGTGG
                     M  A  S  L  A  L  S  S  L  P  T  S  T  T  T

AAAAAACCCTTATTTCCAAAACATCCTCGCATGTTAAGCCATTCCATCGCTTCAAAGTT
61  ------+---------+---------+---------+---------+---------+  120
    TTTTTTGGGAATAAAAGGTTTTGTAGGAGCGTACAATTCGGTAAGGTAGCGAAGTTTCAA
    K  K  P  L  F  S  K  T  S  S  H  V  K  P  F  H  R  F  K  V

TCATGCAATGCACCCGCTGATAACAATGAGACAAAACCGTCAATAATTCTGATACCCCAAAG
121 ------+---------+---------+---------+---------+---------+  180
    AGTACGTTACGTGGGCGACTATTGTTACTCTGTTTTGGCAGTTATTAAGACTATGGGGTTTC
    S  C  N  A  P  A  D  N  N  D  K  T  V  N  N  S  D  T  P  K

CTCATACTACCCAAAACACCACTTGAAACGCAGAACGTAGACAGGAGAAACTTGCTTCTG
181 ------+---------+---------+---------+---------+---------+  240
    GAGTATGATGGGTTTTGTGGTGAACTTTGCGTCTTGCATCTGTCCTCTTTGAACGAAGAC
    L  I  L  P  K  T  P  L  E  T  Q  N  V  D  R  R  N  L  L  L

GGACTCGGAGTCTCTACGGCGCTGCCAACTTGACGACCATTCCGTCAGCCTTTGGCATT
241 ------+---------+---------+---------+---------+---------+  300
    CCTGAGCCTCAGAGATGCCGCGACGGTTGAACTGCTGGTAAGGCAGTCGGAAACCGTAA
    G  L  G  G  L  Y  G  A  A  N  L  T  T  I  P  S  A  F  G  I
```

FIGURE 15B

```
     CCCATCGCTGCTCCAGACAATATTTCAGACTGTGTTGCTGCTGACTTCAAACCTAAGGAAC
301  ------------+---------+---------+---------+---------+---------+  +360
     GGGTAGCGACGAGGTCTGTTATAAAGTCTGACACAACGACGCTGAAGTTTGGATTCCTTG
      P   I   A   A   P   D   N   I   S   D   C   V   A   A   T   S   N   L   R   N

AGCAAAGACGCTATAAGGGACTAGCGTTGTCCTCCGGTGCTTTCAACAAACAAACCA
361  ------------+---------+---------+---------+---------+---------+  +420
     TCGTTTCTGCGATATTCCCTGATCGCCACAACAGGAGGCCACGAAAGTTGTTGTTTGGT
      S   K   D   A   I   R   G   L   A   C   C   P   P   V   L   S   T   N   K   P

ATGGATTACGTCCTTCCTTCCTTCAAACCCTGTGATTCGTGTTCGACCAGCTGCACAGAAAGCC
421  ------------+---------+---------+---------+---------+---------+  +480
     TACCTAATGCAGGAAGGAAGTTTGGGACACTAAGCACACTAAGCAACAAGCTGGTCGACGTGTCTTTCGG
      M   D   Y   V   L   P   S   N   P   V   I   R   V   R   P   A   A   Q   K   A

ACTGCCGATTACACTGCTAAGTATCAACAAGCAATTCAAGCCATGAAGGATCTCCCCGAG
481  ------------+---------+---------+---------+---------+---------+  +540
     TGACGGCTAATGTGACGATTCATAGTTGTTCGTTAAGTTCGGTACTTCCTAGAGGGCTC
      T   A   D   Y   T   A   K   Y   Q   Q   A   I   Q   A   M   K   D   L   P   E

GACCACCCCACATAGCTGGAAGCAACAAGGCAAGATTCACTGTGCTTATTGCAACGGTGGT
541  ------------+---------+---------+---------+---------+---------+  +600
     CTGGTGGGTGTATCGACCTTCGTTGTTCCGTTCTAAGTGACACGAATAACGTTGCCACCA
      D   H   P   H   S   W   K   Q   Q   G   K   I   H   C   A   Y   C   N   G   G
```

FIGURE 15C

```
601  TACAATCAAGAACAAAGTGGTTACCCGAATTTACAACTTCAGATTCACAACTCATGGCTC  +660
     ATGTTAGTTCTTGTTTCACCAATGGGCTTAAATGTTGAAGTCTAAGTGTTGAGTACCGAG
      Y  N  Q  E  Q  S  G  Y  P  N  L  Q  L  Q  I  H  N  S  W  L

661  TTCTTTCCTTTCCACCGGTGGTACCCTCTATTTCTACGAGAAGATATTGGGAAGTTGATT  +720
     AAGAAAGGAAAGGTGGCCACCATGGGAGATAAAGATGCTCTTCTATAACCCTTCAACTAA
      F  F  F  H  R  W  Y  L  Y  F  Y  E  K  I  L  G  K  L  I

721  AATGATCCAACTTTCGCTCTACCTTACTGAACTGGGATAACCCTACTGGAATGGTTATT   +780
     TTACTAGGTTGAAAGCGAGATGGAATGACTTGACCCTATTGGGATGACCTTACCAATAA
      N  D  P  T  F  A  L  P  Y  W  N  D  N  P  T  G  M  V  I

781  CCTGCCATGTTCGAACAGAACAGCAAAACTAACTCTCTGTTTGACCCTTTAAGGGATGCG  +840
     GGACGGTACAAGCTTGTCTTGTCGTTTTGATTGAGAGACAAACTGGGAAATTCCCTACGC
      P  A  M  F  E  Q  N  S  K  T  N  S  L  F  D  P  L  R  D  A

841  AAACACCTCCCCACCTTCTATCTTTGATGTTGAATATGCTGGTGCAGACACTGGTGCCACT  +900
     TTTGTGGAGGGTGGAAGATAGAAACTACAACTTATACGACCACGTCTGTGACCACGGTGA
      K  H  L  P  P  S  I  F  D  V  E  Y  A  G  A  D  T  G  A  T
```

FIGURE 15D

```
      TGTATAGACCAGATAGCCATTAATCTGTCTTCAATGTACAGACAGATGGTCACCAACTCC
901   ------+---------+---------+---------+---------+---------+   +960
      ACATATCTGGTCTATCGGTAATTAGACAGAAGTTACATGTCTGTCTACCAGTGGTTGAGG
       C  I  D  Q  I  A  I  N  L  S  S  M  Y  R  Q  M  V  T  N  S

ACTGATACAAAACGATTCTTCGGTGGCGAATTTGTAGCTGGAAATGACCCTCTTGCGAGC
961   ------+---------+---------+---------+---------+---------+   +1020
      TGACTATGTTTTGCTAAGAAGCCACCGCTTAAACATCGACCTTTACTGGGAGAACGCTCG
       T  D  T  K  R  F  F  G  G  E  F  V  A  G  N  D  P  L  A  S

GAGTTCAACGTAGCTGGGACCGTAGAAGCTGGGGTTCACACTGCGGCTCACCGCTGGGTG
1021  ------+---------+---------+---------+---------+---------+   +1080
      CTCAAGTTGCATCGACCCTGGCATCTTCGACCCCAAGTGTGACGCCGAGTGGCGACCCAC
       E  F  N  V  A  G  T  V  E  A  G  V  H  T  A  A  H  R  W  V

GGTAATTCTAGGATGGCCAACAGCGAAGACATGGGGAACTTCTACTCCGCAGGATATGAT
1081  ------+---------+---------+---------+---------+---------+   +1140
      CCATTAAGATCCTACCGGTTGTCGCTTCTGTACCCCTTGAAGATGAGGCGTCCTATACTA
       G  N  S  R  M  A  N  S  E  D  M  G  N  F  Y  S  A  G  Y  D

CCTCTCTTTTACGTCCACCATGCGAATGTCGACAGGATGTGGCAAATCTGGAAAGATATT
1141  ------+---------+---------+---------+---------+---------+   +1200
      GGAGAGAAAATGCAGGTGGTACGCTTACAGCTGTCCTACACCGTTTAGACCTTTCTATAA
       P  L  F  Y  V  H  H  A  N  V  D  R  M  W  Q  I  W  K  D  I
```

FIGURE 15E

```
     GACAAGAAGACACACAAGGATCCGACCTCTGGCGACTGGCTAAATGCATCATACGTGTTT
1201 ------+---------+---------+---------+---------+---------+1260
     CTGTTCTTCTGTGTGTTCCTAGGCTGGAGACCGCTGACCGATTACGTAGTATGCACAAA
      D   K   K   T   H   K   D   P   T   S   G   D   W   L   N   A   S   Y   V   F

TACGATGAGAATGAAAATCTTGTACGTGTCTACAACCGAGACTGTGTAGACATTAATCGG
1261 ------+---------+---------+---------+---------+---------+1320
     ATGCTACTCTTACTTTTAGAACATGCACAGATGTTGGCTCTGACACATCTGTAATTAGCC
      Y   D   E   N   E   N   L   V   R   V   Y   N   R   D   C   V   D   I   N   R

ATGGGATATGACTACGAAAGGTCAGCAATCCCATGGATCCGTAGTCGGCCGACTGCACAT
1321 ------+---------+---------+---------+---------+---------+1380
     TACCCTATACTGATGCTTTCCAGTCGTTAGGGTACCTAGGCATCAGCCGGCTGACGTGTA
      M   G   Y   D   Y   E   R   S   A   I   P   W   I   R   S   R   P   T   A   H

GCGAAGGGGGCGAACGTTGCTGCTAAGTCTGCTGGAATCGTGCAGAAGGTGGAGGATATC
1381 ------+---------+---------+---------+---------+---------+1440
     CGCTTCCCCCGCTTGCAACGACGATTCAGACGACCTTAGCACGTCTTCCACCTCCTATAG
      A   K   G   A   N   V   A   A   K   S   A   G   I   V   Q   K   V   E   D   I

GTATTCCCGCTGAAGTTAAACAAGATAGTGAAGGTTCTAGTGAAGAGGCCAGCTACAAAC
1441 ------+---------+---------+---------+---------+---------+1500
     CATAAGGGCGACTTCAATTTGTTCTATCACTTCCAAGATCACTTCTCCGGTCGATGTTTG
      V   F   P   L   K   L   N   K   I   V   K   V   L   V   K   R   P   A   T   N
```

FIGURE 15F

```
     AGGACCAAGGAGGAGAAAGGAGAAATGAGCTGTTGTTCGTGAATGGAATCACGTTT
1501 ------+---------+---------+---------+---------+---------+ +1560
     TCCTGGTTCCTCCTCCCTTTCCTCTTTCGTTACTCGACAACAAGCACTTACCTTAGTGCAAA
      R  T  K  E  G  K  E  K  A  N  E  L  L  F  V  N  G  I  T  F

GATGCTGAGCGGTTTCTAAAGATTGACGTGTTTGTCAACGACGTCGACGATGGAATTCAG
1561 ------+---------+---------+---------+---------+---------+ +1620
     CTACGACTCGCCAAAGATTTCTAACTGCACAAACAGTTGCTGCAGCTGCTACCTTAAGTC
      D  A  E  R  F  L  K  I  D  V  F  V  N  D  V  D  D  G  I  Q

ACCACCGCTGCTGATAGTGAGTTTGCTGGTAGTTTCGCACAGTTGCCACATAACCATGGC
1621 ------+---------+---------+---------+---------+---------+ +1680
     TGGTGGCGACGACTATCACTCACTCAAACGACCATCAAAGCGTGTCAACGGTGTATTGGTACCG
      T  T  A  A  D  S  E  F  A  G  S  F  A  Q  L  P  H  N  H  G

GACAAGATGTTTATGAGGAGTGGGGCAGCGTTCGGGGATCACGGAGCTCTTGGAAGACATT
1681 ------+---------+---------+---------+---------+---------+ +1740
     CTGTTCTACAAATACTCCTCACCCCGTCGCAAGCCCTAGTGCCTCGAGAACCTTCTGTAA
      D  K  M  F  M  R  S  G  A  A  F  G  I  T  E  L  L  E  D  I

GAAGCTGAAGGTGATGACTCTGTGTTGTGTGACATTGGTGCCGAGAACAGGGTGTGATGAA
1741 ------+---------+---------+---------+---------+---------+ +1800
     CTTCGACTTCCACTACTGAGACAACAACACTGTAACCACGGCTCTTGTCCCACACTACTT
      E  A  E  G  D  D  S  V  V  V  T  L  V  P  R  T  G  C  D  E
```

FIGURE 15G

```
     GTAACTATTGGCGAGAGATCAAGATTCAGCTGGTTCCCATTGTTTAAAGTCTATTGAAGTAA
1801 ------+---------+---------+---------+---------+---------+1860
     CATTGATAACCGCTCTAGTTCTAAGTCGACCAAGGGTAACAAATTTCAGATAACTTCATT
      V  T  I  G  E  I  K  I  Q  L  V  P  I  V  *

TGCATTTCAATTGTCATTAGTATGCATGGGTACGTAAATCTGTTCGCTGTCTGTGGTTATC
1861 ------+---------+---------+---------+---------+---------+1920
     ACGTAAAGTTAACAGTAATCATACGTACCCATGCATTTAGACAAGCGACAGACCAATAG

GAGGATTTTGATGTTCTCGTAACCAAATAATAAGGATTGTCATTCCATGTTTGGAATCG
1921 ------+---------+---------+---------+---------+---------+1980
     CTCCTAAAACTACAAGAGCATTGGTTTATTATTCCTAACAGTAAGGTACAAACCTTAGC

TGTAACCGCAGGCATGCATATGTTTGATTGTTATTTTTACTTGAAGCACTTCTGTTTAG
1981 ------+---------+---------+---------+---------+---------+2040
     ACATTGGCGTCCGTACGTATACAAACTAACAAATAAAAATGAACTTCGTGAAGACAAAATC

TAAAAAAAAAAAAAA
2041 ------+--- 2057
     ATTTTTTTTTTTTT
```

POLYPHENOL OXIDASE GENES FROM LETTUCE

CROSS REFERENCE TO RELATED APPLICATIONS

This application is a continuation of U.S. Ser. No. 09/443,067, filed Feb. 15, 2000, now U.S. Pat. No. 6,627,794, issued Sep. 30, 2003, which is a continuation-in-part of U.S. Ser. No. 08/976,222, filed Nov. 21, 1997 now abandoned and PCT International Application No. PCT/AU98/00362 filed May 19, 1998. U.S. Ser. No. 08/976,222 claims Paris Convention priority from Australian Patent Application No. PO 6849 filed on May 19, 1997, and is a United States continuation-in-part application of PCT International Application No. PCT/AU96/00310 filed on May 22, 1996, which claims Paris Convention priority from Australian Patent Application Nos. PN 3098, filed May 23, 1995 and PN 5600, filed Sep. 26, 1995. PCT International Application No. PCT/AU98/00362 claims Paris Convention priority from Australian Patent Application No. PO 6849 filed on May 19, 1997. The contents of all of the referenced applications are hereby incorporated by reference into the present application.

STATEMENT REGARDING FEDERALLY SPONSORED RESEARCH OR DEVELOPMENT

Not Applicable

FIELD OF THE INVENTION

The present invention relates generally to genetic sequence of plants that encode polyphenol oxidase (PPO) enzymes and functional fragments and parts thereof. More particularly, the present invention provides nucleic acid molecules encoding polyphenol oxidase enzymes of lettuce, banana, tobacco and pineapple plants. The invention further provides methods of isolating said nucleic acid molecules.

BACKGROUND OF THE INVENTION

Browning of plant tissues often occurs following injury or damage and this generally results in spoilage of fruit and vegetables. Undesirable browning also occurs during processing of plant materials to produce food or other products. Steps are taken during transport, storage, and processing to prevent these browning reactions. Often this involves the use of chemicals such as sulphur dioxide but the use of these substances is likely to be restricted in the future due to concerns about their safety and consumer acceptance. For example, the US Food and Drug Administration banned the use of sulphite for most fresh fruit and vegetables in 1986. The production of fruit and vegetable varieties with an inherently low susceptibility to brown would remove the need for these chemical treatments.

It will be understood that browning in plants is predominantly catalysed by the enzyme PPO. PPO is localised in the plastids of plant cells whereas the phenolic substrates of the enzyme are stored in the plant cell vacuole. This compartmentation prevents the browning reaction from occurring unless the plant cells are damaged and the enzyme and its substrates are mixed.

2. Description of Related Art

The prior art includes International Application PCT/AU92/00356 to the present applicant which describes the cloning of PPO genes from grapevine, broad bean leaf, apple fruit and potato tuber. This application recognises that PPO levels in plants may be manipulated by increasing or decreasing expression of PPO gene. The application also identifies two conserved copper binding sites in PPO genes, designated CuA and CuB. However, the method described in PCT/AU92/00356 which was used to clone the PPO genes from apple and potato involved the use of an oligo dT reverse primer for polymerase chain reaction (PCR). Whilst the method is acceptable, in some tissues, it does not give rise to a strong band of the predicted size or else it gives rise to many additional products making it difficult to resolve the PPO fragment.

Accordingly, it is an object of the present invention to overcome or at least alleviate one or more of the difficulties related to the prior art.

SUMMARY OF THE INVENTION

This application is a continuation-in-part application of continuation-in-part application of U.S. Ser. No. 08/976,222, filed Nov. 21, 1997, and International Application No. PCT/AU98/00362 filed May 19, 1998, the entire contents of which are incorporated herein by way of reference.

Bibliographic details of the publications referred to in this specification by author are collected at the end of the description.

Sequence Identity Numbers (SEQ ID NOs.) for the nucleotide and amino acid sequences referred to in the specification appear after the claims.

Throughout this specification and the claims that follow, unless the context requires otherwise, the word "comprise", or variations such as "comprises" or "comprising" will be understood to imply the inclusion of a stated element or integer or group of elements or integers, but not the exclusion of any other element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In work leading up to the present invention, the inventors sought to produce improved methods for isolating PPO-encoding nucleic acid molecules which are susceptible for use in modifying the expression of endogenous PPO genes in plants, to reduce browning and modify ripening and storage characteristics of plant tissues and organs.

Accordingly, the inventors have cloned several PPO-encoding genes from lettuce, tobacco, banana and pineapple and produced recombinant gene constructs comprising same for the expression of recombinant PPO polypeptides and nucleic acids capable of modifying the PPO content of plant tissues and cells when expressed therein.

One aspect of the present invention provides an isolated nucleic acid molecule that comprises a nucleotide sequence which encodes or is complementary to a nucleotide sequence which encodes a PPO polypeptide of lettuce, banana, tobacco or pineapple having an amino acid sequence set forth in any one of SEQ ID NOS: 2, 4, 6, 8, 10, 12, 14, 16, 18, 20, 22, 24, 26, 28 or 30, or comprising the copper-binding site of any one of said amino acid sequences.

In an alternative embodiment, the present invention provides an isolated nucleic acid molecule that encodes a PPO polypeptide of lettuce, banana, tobacco or pineapple wherein said nucleic acid molecule comprises a nucleotide sequence selected from the group consisting of:

(i) a nucleotide sequence set forth in any one of SEQ ID NOS: 1, 3, 5, 7, 9, 11, 13, 15, 17, 19, 21, 23, 25, 27, or 29;

(ii) a fragment of (i) comprising a nucleotide sequence that encodes the copper-binding site of a PPO polypeptide;

(iii) a degenerate nucleotide sequence of (i) or (ii); and (iv) a nucleotide sequence that is complementary to (i) or (ii) or (iii).

A second aspect of the invention provides gene constructs comprising the isolated nucleic acid molecules of the invention, preferably in a format suitable for expression in plants, particularly in banana, lettuce, tobacco or pineapples.

A third aspect of the invention provides a method of modifying the endogenous PPO activity of plant cells, tissue, or organs, particularly those cells, tissues, and organs of lettuce, banana, tobacco and pineapples, by expressing the isolated PPO-encoding nucleic acid molecules, or a fragment or analogue or homologue thereof, in the sense or antisense orientation therein for a time and under conditions sufficient to modify transcription or translation of the endogenous mRNA encoding PPO and/or to produce a functional PPO enzyme. As used herein, the word "modify" clearly encompasses any alteration to a stated integer, including both a reduction and an increase thereof.

Accordingly, in one embodiment, this aspect of the invention provides a method of increasing the level of lettuce, banana, pineapple or tobacco PPO activity in a plant or a cell, tissue or organ thereof, said method comprising:

(i) introducing a nucleotide sequence to said plant or a cell, tissue or organ thereof which sequence encodes a PPO polypeptide of lettuce, banana, tobacco or pineapple having an amino acid sequence set forth in any one of SEQ ID NOS: 2, 4, 6, 8, 10, 12, 14, 16, 18, 20, 22, 24, 26, 28, or 30, or an enzymatically-active PPO polypeptide comprising the copper-binding site of any one of said amino acid sequences; and (ii) expressing said nucleotide sequence to produce an enzymatically-active PPO polypeptide.

In an alternative embodiment, this aspect of the invention provides a method of increasing the level of lettuce, banana, pineapple or tobacco PPO activity in a plant or a cell, tissue or organ thereof, said method comprising:

(i) introducing a nucleic acid molecule to said plant or a cell, tissue or organ thereof which nucleic acid molecule comprises the nucleotide sequence set forth in any one of SEQ ID NOS: 1, 3, 5, 7, 9, 11, 13, 15, 17, 19, 21, 23, 25, 27, or 29, or a degenerate sequence thereof; and (ii) expressing said nucleic acid molecule to produce an enzymatically-active PPO polypeptide.

In an alternative embodiment, this aspect of the invention provides a method of decreasing the level of PPO activity in a plant or a cell, tissue or organ thereof, said method comprising introducing a nucleic acid molecule to said plant or a cell, tissue or organ thereof which comprises a nucleotide sequence selected from the group consisting of:

(i) a nucleotide sequence which encodes a PPO polypeptide of lettuce, banana, tobacco or pineapple having an amino acid sequence set forth in anyone of SEQ ID NOS: 2, 4, 6, 8, 10, 12, 14, 16, 18, 20, 22, 24, 26, 28, or 30, or the copper-binding site of any one of said amino acid sequences;

(ii) a nucleotide sequence set forth in any one of SEQ ID NOS: 1, 3, 5, 7, 9, 11, 13, 15, 17, 19, 21, 23, 25, 27, or 29;

(iii) a fragment of (ii) comprising a nucleotide sequence that encodes the copper-binding site of a PPO polypeptide; and (iv) a nucleotide sequence that is complementary to (i) or (ii) or (iii).

A fourth aspect of the present invention clearly extends to transfected and transformed cells, tissues, organs and whole organisms that have the subject nucleic acid molecules of the invention introduced thereto. The introduced nucleic acid molecules may exist as extra chromosomal genetic material, or alternatively or in addition, in a form that has been integrated into the cellular genome. This aspect of the invention clearly encompasses transformed plants and plant parts and propagules comprising the subject nucleic acid molecules as an addition to their normal genome composition.

A further aspect of the invention relates to methods of isolating homologues of the nucleic acid molecules exemplified herein, in particular methods relying upon nucleic acid hybridization between highly-conserved regions of the exemplified sequences and nucleotide sequences of homologous PPO-encoding sequences. Such methods include standard nucleic acid hybridizations (i.e. RNA:DNA and RNA:RNA and DNA:DNA) and polymerase chain reaction (PCR)-based and isothermal amplification methods.

According to this aspect of the invention, there is provided a method for preparing nucleic acid encoding an internal fragment of a PPO polypeptide of banana, lettuce, tobacco or pineapple comprising at least a portion of a copper-binding site of said polypeptide or a hybridizable fragment of said nucleic acid, said method including:

(i) providing:
(a) banana, lettuce, tobacco or pineapple PPO cells, tissue or organs having PPO activity;
(b) a first primer having a nucleotide sequence capable of hybridizing to a copper (Cu) binding site-encoding region of a PPO gene or upstream thereof;
(c) a second primer having a nucleotide sequence capable of hybridizing to the complement of a copper (Cu) binding site-encoding region of a PPO gene or downstream thereof; and
(d) an adaptor primer;

(ii) isolating RNA from said cells, tissues or organs;

(iii) treating the RNA to construct copy DNA (cDNA) therefrom; and (iv) amplifying the cDNA so formed using the first and second primers.

Preferably, the first primer comprises a nucleotide sequence selected from the group consisting of:

(i)
(SEQ ID NO: 31)
5'-GCGAATTCTT[TC][TC]TICCITT[TC][CA][TC][AC]G-3';

(ii)
(SEQ ID NO: 32)
5'-GCGAATTCGATCCIACITT[TC]GC[GT]TTICC-3';

(iii)
(SEQ ID NO: 33)
5'-GCGAATTCAA[TC]GTIGA[TC][AC]GIATGTGG-3';

(iv)
(SEQ ID NO: 34)
5'-GCGAATTCTICA[TC]TG[TC]GCITA[TC]TG-3';

-continued (v)
(SEQ ID NO: 35)
5'-GCGAATTCTTICCIT[TA][TC]TGGAA[TC]TGGG-3';
and (vi)
a hybridizable fragment of any one of (i) to (v).

Preferably, the second primer comprises a nucleotide sequence selected from the group consisting of:

(i)
(SEQ ID NO: 36)
5'-GCCTGCAGCCACATIC[TG][AG]TCIAC[AG]TT-3';

(ii)
(SEQ ID NO: 37)
5'-GCCTGCAGTT[TC]TC[AG]TC[AG]TAGAA-3';
and (iii)
a hybridizable fragment of (i) or (ii).

Preferably, the treatment of RNA to construct cDNA is performed by treating the RNA with reverse transcriptase and an adaptor primer that comprises the nucleotide sequence:

(SEQ ID NO: 38)
5'-GACTCGAGTCGACATCGATTTTTTTTTTTTTTTT-3' or a hybridizable fragment thereof to form cDNA.

Nucleic acid encoding the N-terminal fragment of the PPO polypeptide of banana, lettuce, tobacco or pineapple can be obtained by attaching an anchor to the 5'-end of the cDNA formed and amplifying said cDNA using a first primer that binds to said anchor and a second primer in the antisense orientation, wherein the nucleotide sequence of said second primer is derived from the sequence of the internal PPO fragment. In this embodiment, the primer in the sense orientation may comprise a nucleotide sequence selected from the group consisting of:

(i)
(SEQ ID NO: 39)
5'-ATATCACCTGTCGGTACATGACGGC-3';

(ii)
(SEQ ID NO: 40)
5'-GTGCCATTGTAGTCGAGGTCAATCA-3';

(iii)
(SEQ ID NO: 41)
5'-CCAGTGCCTGGTTTAGGTGTATTCAC-3';
and (iii)
a hybridizable fragment of (i) or (ii) or (iii).

Additionally, in a preferred embodiment, the primer in the antisense orientation may comprise a nucleotide sequence selected from the group consisting of:

(i)
(SEQ ID NO: 42)
5' TGCTGTTCTGTTCGAACATGGCAG-3';

(ii)
(SEQ ID NO; 43)
5'-TATACAAGTGGCACCAGTGTCTGC-3';

(iii)
(SEQ ID NO: 44)
5'-CCGCATTGTGGATGACTTCCATCTG-3';

(iv)
(SEQ ID NO; 45)
5'-CCAGAATGGGATGGTGAAGGTGTCG-3';
and (v)
a hybridizable fragment of any one of (i) to (iv).

Nucleic acid encoding the C-terminal fragment of the PPO polypeptide of banana, lettuce, tobacco or pineapple can also be obtained by amplifying said cDNA using an adaptor primer and a primer in the sense orientation, wherein the nucleotide sequence of said second primer is derived from the sequence of the internal PPO fragment. In this embodiment, the primer in the sense orientation may comprise a nucleotide sequence selected from the group consisting of:

(i)
5' CGCTGGGTGGGTAATTCTAGGATG-3';    (SEQ ID NO: 46)

(ii)
5'-AGTCATCCACAATGCGGCGCACATG-3';    (SEQ ID NO: 47)
and (iii)
5'-GTTGCTCTTCTTAGGCTCGGCTTAC-3'    (SEQ ID NO: 48)

(iv)
a hybridizable fragment thereof.

The adaptor primer may include the following sequence or a hybridizable fragment thereof:

5'-GACTCGAGTCGACATCG-3'.    (SEQ ID NO: 49)

BRIEF DESCRIPTION OF THE DRAWINGS

FIG. 1 is a representation showing the BPPO2 cDNA nucleotide sequence (SEQ ID NO: 1) encoding part of a banana PPO protein, and derived protein sequence therefor (SEQ ID NO: 2).

FIG. 2 is a representation showing the BPPO8 cDNA nucleotide sequence (SEQ ID NO:3) encoding part of a banana PPO protein, and derived protein sequence therefor (SEQ ID NO: 4).

FIG. 3 is a representation showing the BANPPO34 cDNA nucleotide sequence (SEQ ID NO:5) encoding part of a banana PPO protein, and derived protein sequence therefor (SEQ ID NO: 6).

FIG. 4 is a representation showing the BANPPO35 cDNA nucleotide sequence (SEQ ID NO:7) encoding part of a banana PPO protein, and derived protein sequence therefor (SEQ ID NO:8).

FIG. 5 is a representation showing the TOBPPO6 cDNA nucleotide sequence (SEQ ID NO: 9) encoding part of a tobacco PPO protein, and derived protein sequence therefor (SEQ ID NO:10).

FIG. 6 is a representation showing the TOBPPO25 cDNA nucleotide sequence (SEQ ID NO:11) encoding part of a tobacco PPO protein, and derived protein sequence therefor (SEQ ID NO:12).

FIG. 7 is a representation showing the TOBPPO26 cDNA nucleotide sequence (SEQ ID NO:13) encoding part of a tobacco PPO protein, and derived protein sequence therefor (SEQ ID NO:14).

FIG. 8 is a representation showing the PINPPO20 cDNA nucleotide sequence (SEQ ID NO:15) encoding part of a pineapple PPO protein, and derived protein sequence therefor (SEQ ID NO:16).

FIG. 9 is a representation showing the PINPPO2 cDNA nucleotide sequence (SEQ ID NO:17) encoding part of a pineapple PPO protein, and derived protein sequence therefor (SEQ ID NO:18).

FIG. 10 is a representation showing the PINPPOFL cDNA nucleotide sequence (SEQ ID NO:19) encoding a pineapple PPO protein, and derived protein sequence therefor (SEQ ID NO:20).

FIG. 11 is a representation showing the BANPPO1 cDNA nucleotide sequence (SEQ ID NO: 21), and derived protein sequence therefor (SEQ ID NO: 22), including both the putative chloroplast transit sequence and the mature banana PPO protein.

FIG. 12 is a representation showing the BANPPO11 cDNA nucleotide sequence (SEQ ID NO: 23) encoding part of a banana PPO protein, and derived protein sequence therefor (SEQ ID NO: 24).

FIG. 13 is a representation showing the PINPPO1 cDNA nucleotide sequence (SEQ ID NO: 25) encoding part of a pineapple PPO protein, and derived protein sequence therefor (SEQ ID NO: 26).

FIG. 14 is a representation showing the 5PINA cDNA nucleotide sequence (SEQ ID NO: 27) encoding part of a pineapple PPO protein, and derived protein sequence therefor (SEQ ID NO: 28).

FIG. 15 is a representation showing the composite LOP1 cDNA nucleotide sequence (SEQ ID NO: 29) encoding a lettuce PPO protein, and derived protein sequence therefor (SEQ ID NO: 30), including both the putative chloroplast transit sequence and the mature banana PPO protein.

DETAILED DESCRIPTION OF THE INVENTION

In a first aspect of the present invention there is provided a method for preparing nucleic acid encoding PPO, fragments and derivatives thereof, which method includes
  providing
  a source of a polypeptide having PPO activity,
  a first primer having a sequence corresponding to a first conserved region of PPO in sense orientation, and
  a second primer having a sequence corresponding to a second conserved region of PPO in antisense orientation;
  isolating RNA from the source of polypeptide having PPO activity;
  treating the RNA to construct copy DNA (cDNA) therefrom; and
  amplifying the cDNA so formed using the first and second primers.

Applicant has found that the method of the present invention, which involves the use of a second primer based on PPO, means that there is less likelihood that other (non-PPO) genes are amplified. Furthermore, the method of the present invention dramatically increases the amount of genuine product formed in most cases. Moreover, the added specificity provided by the second PPO-based primer makes it possible to clone PPO more readily from certain plants in which it was difficult to obtain a clone using one primer and oligo-dT. For example, with lettuce cDNA the applicant saw only a faint smear of a range of products with GEN3/GEN8 and oligo-dT but strong bands of the predicted size with GEN3/GEN8 and REV1.

In a preferred aspect of the present invention there is provided a method for preparing nucleic acid encoding banana, lettuce, tobacco or pineapple PPO, fragments and derivatives thereof, which method includes
  providing
  a source of a polypeptide having banana, lettuce, tobacco or pineapple PPO activity,
  a first primer having a sequence corresponding to a first conserved region of banana, lettuce, tobacco or pineapple PPO in sense orientation, and
  a second primer having a sequence corresponding to a second conserved region of banana, lettuce, tobacco or pineapple PPO in antisense orientation;
  isolating RNA from the source of polypeptide having banana, lettuce, tobacco or pineapple PPO activity;
  treating the RNA to construct copy DNA (cDNA) therefrom; and
  amplifying the cDNA so formed using the first and second primers.

The terms "nucleic acid encoding banana/lettuce/tobacco/pineapple PPO" and "banana/lettuce/tobacco/pineapple PPO gene" as used herein should be understood to refer to a banana/lettuce/tobacco/pineapple PPO gene or a sequence substantially homologous therewith. For example, these terms include sequences which differ from the specific sequences given in the Examples hereto but which, because of the degeneracy of the genetic code, encode the same protein. Applicants have found that there are families of PPO genes in most plants. Thus, there are likely to be other PPO genes in lettuce, banana, tobacco and pineapple in addition to those which have been isolated. These could be cloned using the methods of the present invention. Thus, the terms "nucleic acid encoding banana/lettuce/tobacco/pineapple PPO" and "banana/lettuce/tobacco/pineapple PPO gene" should be understood to include banana/lettuce/tobacco/pineapple PPO genes other than those specific genes that have been isolated. The terms may also include presequences such as chloroplast transit sequence as well as sequences encoding mature PPO protein.

The term "derivative" as used herein includes nucleic acids that have been chemically or otherwise modified, for example mutated, or labelled, or nucleic acids incorporating a catalytic cleavage site.

The term "fragment" includes functionally active fragments of a PPO gene which encode a polypeptide or peptide having PPO activity or are capable of altering expression of the PPO genes. Examples of alteration of the gene may include up-regulation or down-regulation of the gene, coding of the gene, transcription of the gene, binding of the gene or stability of the gene sequence.

The source of polypeptide having PPO activity is preferably a source of polypeptide having banana, lettuce, tobacco or pineapple PPO activity. The source of polypeptide having banana PPO activity may be banana fruit, preferably young banana fruit, more preferably the flesh of young banana fruit. The source of polypeptide having banana PPO activity may be banana peel, preferably young banana peel, more preferably the peel of young banana fruit. The source of polypeptide having lettuce PPO activity may be lettuce leaves, preferably young lettuce leaves. The source of polypeptide having tobacco PPO activity may be tobacco leaves, preferably young tobacco leaves. The source of polypeptide having pineapple PPO activity may be pineapple fruit, preferably the flesh of the pineapple fruit, more preferably the flesh of pineapple fruit exhibiting blackheart disorder.

The RNA may be isolated by any suitable method including extraction for example with a detergent such as CTAB, use of an oligo-dT spun column as described in PCT/AU92/00356 the entire disclosure of which is incorporated herein by reference, or use of a commercially available kit such as the PolyATtract 1000 system from Promega Corporation.

The step of treating the RNA to construct cDNA according to this aspect of the present invention may include
treating the RNA with reverse transcriptase and an adapter primer to form cDNA.

The adapter primer may be an oligonucleotide adapter primer including the following sequence or part thereof:

```
                                        (SEQ ID NO: 38)
5'-GACTCGAGTCGACATCGATTTTTTTTTTTTTTTT-3'
```

The step of treating the RNA to construct cDNA according to this aspect of the present invention may include
treating the RNA with reverse transcriptase and reverse primer to form cDNA.

The adapter primer may be replaced with a reverse primer having a sequence corresponding to a conserved region of PPO genes including the following sequence of part thereof:

```
                                        (SEQ ID NO: 37)
5'-GCCTGCAGTT[TC]TC[AG]TC[AG]TAGAA-3'
```

The first primer has a sequence corresponding to a first conserved region of PPO. Preferably the first primer has a sequence corresponding to at least a portion of or in close proximity to a first copper binding site of PPO. The second primer has a sequence corresponding to a second conserved region of PPO. Preferably the second primer has a sequence corresponding to at least a portion of or in close proximity to a second copper binding site of PPO. More preferably the first primer has a sequence corresponding to at least a portion of or in close proximity to one of the CuA or CuB binding sites of PPO, and the second primer has a sequence corresponding to at least a portion of or in close proximity to the other of the CuA or CuB binding sites of PPO.

The first and second primers may be degenerate. The first primer may include one of the following sequences or part thereof:

```
(i)
                                        (SEQ ID NO: 31)
5'-GCGAATTCTT[TC][TC]TICCITT[TC][CA][TC][AC]G-3';

(ii)
                                        (SEQ ID NO: 32)
5'-GCGAATTCGATCCIACITT[TC]GC[GT]TTICC-3';

(iii)
                                        (SEQ ID NO: 33)
5'-GCGAATTCAA[TC]GTIGA[TC][AC]GIATGTGG-3';

(iv)
                                        (SEQ ID NO: 34)
5'-GCGAATTCTICA[TC]TG[TC]GCITA[TC]TG-3';

(v)
                                        (SEQ ID NO: 35)
5'-CGCAATTCTTICCIT[TA][TC]TGGAA[TC]TGGG-3';
and
```

```
-continued
(vi)
a hybridizable fragment of any one of (i) to (v).
```

Preferably, the second primer comprises a nucleotide sequence selected from the group consisting of:

```
(i)                                     (SEQ ID NO: 36)
5'-GCCTGCAGCCACATIC[TG][AG]TCIAC[AG]TT-3';

(ii)                                    (SEQ ID NO: 37)
5'-GCCTGCAGTT[TC]TC[AG]TC[AG]TAGAA-3'
```

The cDNA may be amplified using the polymerase chain reaction (PCR).

Those skilled in the art will appreciate that if the Cu binding sites ar internal, the nucleic acid isolated will be a fragment of the PPO gene lacking 3' and 5' termini. However, it is possible to determine the complete nucleic acid sequence of the PPO gene and to prepare or isolate nucleic acid encoding such PPO or antisense to such PPO.

Accordingly, in a further aspect of the present invention, there is provided a method for preparing nucleic acid encoding the C-terminus of PPO (i.e. comprising the 3'-end of the PPO gene), which method includes:
providing
a source of polypeptide having PPO activity
a primer in sense orientation; and
an adapter primer;
isolating RNA from the source of polypeptide having PPO activity;
treating the RNA to construct cDNA therefrom; and
amplifying the cDNA so formed using the primers.

There is also provided a method for preparing nucleic acid encoding the N-terminus of PPO (i.e. comprising the 5'-end of the PPO gene), including:
providing
a source of polypeptide having PPO activity,
an anchor,
primers in antisense orientation; and
an anchor primer;
isolating RNA from the source of polypeptide having PPO activity;
treating the RNA to construct cDNA therefrom;
attaching the anchor to the 5' end of the cDNA so formed; and
amplifying the cDNA using the primers.

The source of polypeptide having PPO activity is preferably a source of polypeptide having banana, lettuce, tobacco or pineapple PPO activity. The source of polypeptide having banana PPO activity may be banana fruit, preferably young banana fruit, more preferably the flesh of young banana fruit. The source of polypeptide having banana PPO activity may be banana peel, preferably young banana peel, more preferably the peel of young banana fruit. The source of polypeptide having lettuce PPO activity may be lettuce leaves, preferably young lettuce leaves. The source of polypeptide having tobacco PPO activity may be tobacco leaves, preferably young tobacco leaves. The source of polypeptide having pineapple PPO activity may be pineapple fruit, preferably the flesh of the pineapple fruit, more preferably the flesh of pineapple fruit exhibiting blackheart disorder.

The RNA may be isolated by any suitable method including extraction for example with a detergent such as CTAB, use of an oligo-dT spun column as described in PCT/AU92/00356 the entire disclosure of which is incorporated herein by reference, or use of a commercially available kit such as the PolyATtract 1000 system from Promega Corporation.

The step of treating the RNA to construct cDNA according to this aspect of the present invention may include treating the RNA with reverse transcriptase and an adapter primer to form cDNA.

The adapter primer may be an oligonucleotide adapter primer including the following sequence or part thereof:

```
                                        (SEQ ID NO: 38)
5'-GACTCGAGTCGACATCGATTTTTTTTTTTTTTTT-3'
```

The adapter primer may be replaced with a reverse primer having a sequence corresponding to a conserved region of PPO genes including the following sequence of part thereof:

```
                                        (SEQ ID NO: 37)
5'-GCCTGCAGTT[TC]TC[AG]TC[AG]TAGAA-3'
```

The primer in sense orientation may be a lettuce PPO specific primer. The primer in sense orientation may include the following sequence or part thereof:

```
5'CGCTGGGTGGGTAATTCTAGGATG-3'    (SEQ ID NO: 46)
```

The primer in sense orientation may be a banana PPO specific prim r. The primer in sense orientation may include the following sequence or part thereof:

```
5'-AGTCATCCACAATGCGGCGCACATG-3'   (SEQ ID NO: 47)
```

The primer in sense orientation may be a tobacco or pineapple PPO specific primer.

The adapter primer may include the following sequence or part thereof:

```
5'-GACTCGAGTCGACATCG-3'.          (SEQ ID NO: 49)
```

The primers in antisense orientation may be lettuce PPO specific primers. The primers in antisense orientation may include the following sequences or part thereof:

```
(i)
5'-TGCTGTTCTGTTCGAACATGGCAG-3';   (SEQ ID NO: 42)
(ii)
5'-TATACAAGTGGCACCAGTGTCTGC-3'    (SEQ ID NO; 43)
```

The primers in antisense orientation may be banana PPO specific primers. The primers in antisense orientation may include the following sequences or part thereof:

```
(i)
5'-CCGCATTGTGGATGACTTCCATCTG-3';  (SEQ ID NO: 44)
(ii)
5'-CCAGAATGGGATGGTGAAGGTGTCG-3'   (SEQ ID NO; 45)
```

The primers in antisense orientation may be tobacco PPO specific primers.

The primers in antisense orientation may be pineapple PPO specific primers. The primers in antisense orientation may include the following sequences or part thereof:

```
(i)
5'-ATATCACCTGTCGGTACATGACGGC-3';  (SEQ ID NO: 39)
(ii)
5'-GTGCCATTGTAGTCGAGGTCAATCA-3'   (SEQ ID NO: 40)
```

The anchor may be of any suitable type. The anchor may be attached by ligation for example using T4 RNA ligase. The anchor primer should be capable of hybridizing with the anchor.

The cDNA may be amplified using PCR.

Those skilled in the art will appreciate that using the methods of the present invention it is possible to determine the complete nucleic acid sequence of the PPO gene of interest and to prepare or isolate nucleic acid encoding such PPO or antisense to such PPO.

In a further aspect of the present invention, there is provided a nucleic acid encoding banana PPO or antisense to banana PPO, fragments and derivatives thereof. Preferably the nucleic acid has the sequence shown in FIG. 1-4, 11 or 12 fragments and derivatives thereof, and substantially homologous sequences.

In a further aspect of the present invention, there is provided a nucleic acid encoding lettuce PPO or antisense to lettuce PPO, fragments and derivatives thereof. Preferably the nucleic acid has the sequence shown in FIG. 15 fragments and derivatives thereof, and substantially homologous sequences.

In a further aspect of the present invention, there is provided a nucleic acid encoding tobacco PPO or antisense to tobacco PPO, fragments and derivatives thereof. Preferably the nucleic acid has the sequence shown in FIG. 5, 6, or 7, fragments and derivatives thereof, and substantially homologous sequences.

In a further aspect of the present invention, there is provided a nucleic acid encoding pineapple PPO or antisense to pineapple PPO, fragments and derivatives thereof. Preferably the nucleic acid has the sequence shown in FIG. 8-10, 13 or 14 and derivatives thereof, and substantially homologous sequences.

The nucleic acid may be prepared by a method as hereinbefore described.

The nucleic acid may be modified, for example by inclusion of a catalytic cleavage site.

In a further aspect of the present invention there is provided a method for preparing a recombinant vector including a nucleic acid encoding banana PPO or antisense to banana PPO, fragments and derivatives thereof, which method includes
    providing
    nucleic acid encoding banana PPO or antisense to banana PPO, fragments and derivatives thereof; and
    a vector; and
    reacting the nucleic acid and the vector to deploy the nucleic acid within the vector.

In a further aspect of the present invention there is provided a method for preparing a recombinant vector including a nucleic acid encoding lettuce PPO or antisense to lettuce PPO, fragments and derivatives thereof, which method includes
    providing
    nucleic acid encoding lettuce PPO or antisense to lettuce PPO, fragments and derivatives thereof; and
    a vector; and
    reacting the nucleic acid and the vector to deploy the nucleic acid within the vector.

In a further aspect of the present invention there is provided method for preparing a recombinant vector including a nucleic acid encoding tobacco PPO or antisense to tobacco PPO, fragments and derivatives thereof, which method includes providing
nucleic acid encoding tobacco PPO or antisense to tobacco PPO, fragments and derivatives thereof; and
a vector; and
reacting the nucleic acid and the vector to deploy the nucleic acid within the vector.

In a further aspect of the present invention there is provided a method for preparing a recombinant vector including a nucleic acid encoding pineapple PPO or antisense to pineapple PPO, fragments and derivatives thereof, which method includes providing
nucleic acid encoding pineapple PPO or antisense to pineapple PPO, fragments and derivatives thereof; and
a vector; and
reacting the nucleic acid and the vector to deploy the nucleic acid within the vector.

The nucleic acid may be prepared by a method as hereinbefore described.

The nucleic acid may be modified, for example by inclusion of a catalytic cleavage site.

The vector may be a plasmid expression vector. For example Bluescript SK+ has been found to be suitable. Alternatively, the vector may be a binary vector. The recombinant vector may contain a promoter, preferably a constitutive promoter upstream of the nucleic acid.

The cloning step may take any suitable form. A preferred form may include fractionating the cDNA, for example on a column or a gel;
isolating a fragment of the expected size, for example from the column or gel; and
ligating said fragment into a suitable restriction enzyme site of the vector, for example the EcoRV site of a Bluescript SK+ vector.

In order to test the clones so formed, a suitable microorganism may be transformed with the vector, the microorganism cultured and the polypeptide encoded therein expressed. The microorganism may be a strain of *Escherichia coli*, for example *E. coli* DH5 has been found to be suitable. Alternatively, appropriate vectors may be used to transform plants.

In a further aspect of the present invention there is provided a recombinant vector including a nucleic acid encoding banana PPO or antisense to banana PPO, fragments and derivatives thereof, which vector is capable of being replicated, transcribed and translated in a unicellular organism or alternatively in a plant.

In a further aspect of the present invention there is provided a recombinant vector including a nucleic acid encoding lettuce PPO or antisense to lettuce PPO, fragments and derivatives thereof, which vector is capable of being replicated, transcribed and translated in a unicellular organism or alternatively in a plant.

In a further aspect of the present invention there is provided a recombinant vector including a nucleic acid encoding tobacco PPO or antisense to tobacco PPO, fragments and derivatives thereof, which vector is capable of being replicated, transcribed and translated in a unicellular organism or alternatively in a plant.

In a further aspect of the present invention there is provided a recombinant vector including a nucleic acid encoding pineapple PPO or antisense to pineapple PPO, fragments and derivatives thereof, which vector is capable of being replicated, transcribed and translated in a unicellular organism or alternatively in a plant.

The nucleic acid may be prepared by a method as hereinbefore described.

The nucleic acid may be modified, for example by inclusion of a catalytic cleavage site.

The vector may be a plasmid expression vector. For example Bluescript SK+ has been found to be suitable. Alternatively, the vector may be a binary vector. The recombinant vector may contain a promoter, preferably a constitutive promoter upstream of the nucleic acid encoding banana, lettuce, tobacco or pineapple PPO or antisense to banana, lettuce, tobacco or pineapple PPO, fragments and derivatives thereof.

The microorganism may be a strain of *Escherichia coli*, for example *E. coli* DH5 has been found to be suitable.

In a further aspect of the present invention there is provided a method of decreasing the level of PPO activity in a plant tissue, which method includes providing
a nucleic acid encoding banana PPO, a modified nucleic acid encoding banana PPO, or a nucleic acid antisense to banana PPO, fragments and derivatives thereof; and
a plant sample; and
introducing said nucleic acid into said plant sample to produce a transgenic plant.

In a further aspect of the present invention there is provided a method of decreasing the level of PPO activity in a plant tissue, which method includes providing
a nucleic acid encoding lettuce PPO, a modified nucleic acid encoding lettuce PPO, or a nucleic acid antisense to lettuce PPO, fragments and derivatives thereof; and
a plant sample; and
introducing said nucleic acid into said plant sample to produce a transgenic plant.

In a further aspect of the present invention there is provided a method of decreasing the level of PPO activity in a plant tissue, which method includes providing
a nucleic acid encoding tobacco PPO, a modified nucleic acid encoding tobacco PPO, or a nucleic acid antisense to tobacco PPO, fragments and derivatives thereof; and
a plant sample; and
introducing said nucleic acid into said plant sample to produce a transgenic plant.

In a further aspect of the present invention there is provided a method of decreasing the level of PPO activity in a plant tissue, which method includes providing
a nucleic acid encoding pineapple PPO, a modified nucleic acid encoding pineapple PPO, or a nucleic acid antisense to pineapple PPO, fragments and derivatives thereof; and
a plant sample; and
introducing said nucleic acid into said plant sample to produce a transgenic plant.

PPO activity may be decreased by the use of sense constructs (cosuppression). Alternatively the nucleic acid may include a sequence encoding antisense mRNA to banana, lettuce, tobacco or pineapple PPO or a functionally active fragment thereof. Alternatively the nucleic acid may encode banana, lettuce, tobacco or pineapple PPO or a functionally active fragment thereof and incorporate a catalytic cleavage site (ribozyme). The nucleic acid may be included in a recombinant vector as hereinbefore described.

In a preferred aspect, the nucleic acid may be included in a binary vector. In a further preferred aspect, the introduction of a binary vector into the plant may be by infection of the plant with an *Agrobacterium* containing the binary vector or by bombardment with nucleic acid coated microprojectiles. Methods for transforming banana, lettuce, tobacco or pineapple with *Agrobacterium* are known to those skilled in the art and are described in, for example, May et al., Bio/technology (1995) 13:486-492, Michelmore et al., Plant Cell Reports (1987) 6:439-442, and Curtis et al., Journal of Experimental Botany (1994) 45:1141-1149, the entire disclosures of which are incorporated herein by reference.

In a further aspect of the present invention there is provided a method of increasing the level of PPO activity in a plant tissue, which method includes
  providing
    a nucleic acid encoding banana PPO or a fragment thereof; and
    a plant sample; and
    introducing said nucleic acid into said plant sample to produce a transgenic plant.

In a further aspect of the present invention there is provided a method of increasing the level of PPO activity in a plant tissue, which method includes
  providing
    a nucleic acid encoding lettuce PPO or a fragment thereof; and
    a plant sample; and
    introducing said nucleic acid into said plant sample to produce a transgenic plant.

In a further aspect of the present invention there is provided a method of increasing the level of PPO activity in a plant tissue, which method includes
  providing
    a nucleic acid encoding tobacco PPO or a fragment thereof; and
    a plant sample; and
    introducing said nucleic acid into said plant sample to produce a transgenic plant.

In a further aspect of the present invention there is provided a method of increasing the level of PPO activity in a plant tissue, which method includes
  providing
    a nucleic acid encoding pineapple PPO or a fragment thereof; and
    a plant sample; and
    introducing said nucleic acid into said plant sample to produce a transgenic plant.

The nucleic acid may be included in a recombinant vector as hereinbefore described. In a preferred aspect, the nucleic acid may be included in a binary vector. In a further preferred aspect, the introduction of the binary vector into the plant may be by infection of the plant with an *Agrobacterium* containing the binary vector or by bombardment with nucleic acid coated microprojectiles.

The plant may be of any suitable type. However the method is particularly applicable to banana, lettuce, tobacco or pineapple.

In a further aspect of the present invention there is provided a transgenic plant, which plant contains nucleic acid capable of modifying expression of the normal banana PPO gene.

In a further aspect of the present invention there is provided a transgenic plant, which plant contains nucleic acid capable of modifying expression of the normal lettuce PPO gene.

The plant may be of any suitable type. Preferably, the plant is banana.

In a further aspect of the present invention there is provided a transgenic plant, which plant contains nucleic acid capable of modifying expression of the normal tobacco PPO gene.

The plant may be of any suitable type. Preferably, the plant is tobacco.

In a further aspect of the present invention there is provided a transgenic plant, which plant contains nucleic acid capable of modifying expression of the normal pineapple PPO gene.

The plant may be of any suitable type. Preferably, the plant is pineapple. The nucleic acid may be as hereinbefore described.

EXAMPLE 1

Cloning Lettuce PPO Genes

Messenger RNA (mRNA) was isolated directly from young leaves of lettuce using the PolyATtract 1000 system from Promega Corporation. First strand cDNA was synthesised with reverse transcriptase using a Timesaver cDNA Synthesis Kit (Pharmacia Biotech) utilising an oligo-dT primer adapter as described in Frohman, M A (1990) in "PCR Protocols: A Guide to Methods and Applications" (M A Innis, D H Gelfrand, J J Sninsky and T J White, eds) Academic Press, New York pp 28-38, the entire disclosure of which is incorporated herein by reference:

```
B26:                              (SEQ ID NO: 38)
5'-GACTCGAGTCGACATCGATTTTTTTTTTTTTTTT-3'
```

Oligonucleotide primers were designed based on known plant PPO DNA sequences in the conserved regions of the gene which encode the copper binding sites, CuA and CuB as described in Dry, IB and Robinson, SP (1994) "Molecular cloning and characterisation of grape berry polyphenol oxidase", Plant Molecular Biology 26: 495-502, the entire disclosure of which is incorporated her in by reference. Two forward primers designed around the CuA sit (GEN3 and GEN8) and one reverse primer designed around the CuB site (REV1) were synthesised:

```
GEN3:                             (SEQ ID NO: 31)
5'-GCGAATTCTT[TC][TC]TICCITT[TC][CA][TC][AC]G-3';

GEN8:                             (SEQ ID NO: 32)
5'-GCGAATTCGATCCIACITT[TC]GC[GT]TTICC-3';

REV1:                             (SEQ ID NO: 36)
5'-GCCTGCAGCCACATIC[TG][AG]TCIAC[AG]TT-3'
```

Although the primers are in the region of the Cu binding sites, one of them (GEN8) is just outside of what is traditionally accepted to be a Cu binding site of the enzyme.

The first strand cDNA was amplified by the polymerase chain reaction (PCR) essentially according to the method of Frohman using GEN3 and REV1 or GEN8 and REV1 primers, each at a final concentration of 1 µM (Dry et al.). Amplification involved an initial program of 2 cycles of denaturation at 94° C. for 1 min, annealing at 37° C. for 2 min, a slow ramp to 72° C. over 2 min and elongation at 72° C. for 3 min, followed by 25 cycles of denaturation at 94° C. for 1 min, annealing at 55° C. for 1 min, and elongation at 72° C. for 3 min. A sample of the amplified DNA was run on an agarose gel and stained with ethidium bromide to determine the size of the PCR products and the remainder was purified and concentrated using PCR Wizard Prep columns (Promega Corporation).

The purified DNA was cloned into Eco RV-cut Bluescript SK+ vector (Stratagene) which had been T-tailed with Taq Polymerase and the ligated DNA was introduced into *E. coli* DH5α by electroporation. Recombinant clones which had an insert of the predicted size were selected and their DNA sequence was determined by automated sequencing. Three putative lettuce PPO clones (LPO316, LPO812 and LPO813) were identified based on their homology to known plant PPO genes.

Using this sequence information a specific forward primer (LET3P) and two reverse primers (LET5P1 and LET5P2) were synthesised:

```
LET3P:
5'CGCTGGGTGGGTAATTCTAGGATG-3';      (SEQ ID NO: 46)

LET5P1:
5'TGCTGTTCTGTTCGAACATGGCAG-3';      (SEQ ID NO: 42)

LET5P2:
5'-TATACAAGTGGCACCAGTGTCTGC-3'      (SEQ ID NO; 43)
```

To obtain the 3'-end of the lettuce PPO gene, the first strand cDNA described above was amplified by the same PCR procedure using 1 µM LET3P primer and 100 nM adapter primer:

```
B25:
(5'-GACTCGAGTCGACATCG-3').          (SEQ ID NO: 49)
```

The amplified cDNA was purified as described above and run on a 2% Nusieve GTG (FMC Bioproducts) agarose gel. A 1000 bp fragment was excised from the gel and the DNA was cloned into T-tailed, Eco RV-cut Bluescript SK+ to yield the 3'-end clones LPO9 and LPO10, which were sequenced.

The 5'-end of the lettuce PPO gene was cloned by a modification of the 5'-RACE procedure originally described by Frohman using a 5'-AmpliFINDER RACE kit (Clontech Laboratories). First strand cDNA was synthesised from mRNA with reverse transcriptase using the LET5P2 primer and an AmpliFINDER anchor was ligated onto the 5'-end of the cDNA. The cDNA was amplified by PCR with LET5P1 primer and the AmpliFINDER anchor primer. The amplified cDNA was purified as described above and run on a 2% Nusieve GTG (FMC Bioproducts) agarose gel. An 850 bp fragment was excised from the gel and the DNA was cloned into T-tailed Eco RV-cut Bluescript SK+ to give the 5'-end clones LPO4, LPO5, LPO6, and LPO7, which were sequenced.

The 5'- and 3'-clones were found to have the predicted overlapping sequences with the original clone and the complete sequence of lettuce PPO (LPO1) was derived by combining the sequences from the various clones (FIG. 15).

EXAMPLE 2

Cloning Banana PPO Genes

Total RNA was isolated from young banana fruit. Fruit tissue (3 g) was frozen and ground to a fine powder in liquid nitrogen with a coffee grinder then added to 20 ml of extraction buffer (2% hexadecyltrimethylammonium bromide (CTAB), 2% polyvinyl pyrolidone, 100 mM Tris-HCl, pH 8.0, 25 mM EDTA, 2 M NaCl, 0.05% spermidine, 2% β-mercaptoethanol) at 65° C. The extract was mixed with 20 ml of chloroform/IAA then centrifuged for 20 minutes at 5,000 RPM and the aqueous phase was re-extracted with chloroform/IAA. The aqueous phase was filtered through Miracloth and 0.25 volumes of 10 M LiCl were added then the sample was incubated overnight at 4° C. before centrifuging for 20 minutes at 8,000 RPM. The supernatant was removed and the pellet was resuspended in 0.5 ml of 1 M NaCl, 0.5% SDS, 10 mM Tris, pH 8.0, 1 mM EDTA. The RNA was extracted once with an equal volume of chloroform/IAA and 2 volumes of ethanol was added. After incubation for 40 mins at −70° C. the solution was centrifuged for 15 minutes at 10,000 RPM. The supernatant was removed and the pellet was rinsed with 80% ethanol, drained, and dried. The pellet was resuspended in 50 µl of sterile water.

First strand cDNA was synthesised from 10 µg total RNA with reverse transcriptase as described in Dry, I. B. and Robinson, S. P. (1994) "Molecular cloning and characterisation of grape berry polyphenol oxidase", Plant Molecular Biology 26: 495-502, the entire disclosure of which is incorporated herein by reference, utilising an oligo-dT primer adapter (Frohman, M. A. (1990) in "PCR Protocols: A Guide to Methods and Applications" (M. A. Innis, D. H. Gelfrand, J. J. Sninsky and T. J. White, eds.) Academic Press, New York pp 28-38, the entire disclosure of which is incorporated herein by reference):

```
B26:                                (SEQ ID NO: 38)
5'-GACTCGAGTCGACATCGATTTTTTTTTTTTTTTT-3'
```

Oligonucleotide primers were designed based on known plant PPO DNA sequences in the conserved regions of the gene which encode the copper binding sites, CuA and CuB (Dry et al.). A forward primer designed around the CuA sit (GEN3) and a reverse primer designed around the CuB site (REV1) were synthesised:

```
GEN 3:                              (SEQ ID NO: 31)
5'-GCGAATTCTT[TC][TC]TICCITT[TC][CA][TC][AC]G-3'

REV1:                               (SEQ ID NO: 36)
5'-GCCTGCAGCCACATIC[TG][AG]TCIAC[AG]TT-3.
```

The first strand reaction was amplified by the polymerase chain reaction (PCR) essentially according to the method of Frohman using GEN3 and REV1 primers, each at a final concentration of 1 µM (Dry et al.). Amplification involved an initial program of 2 cycles of denaturation at 94° C. for 1 min, annealing at 37° C. for 2 min, a slow ramp to 72° C. over 2 min and elongation at 72° C. for 3 min, followed by 25 cycles of denaturation at 94° C. for 1 min, annealing at 55° C. for 1 min, and elongation at 72° C. for 3 min. A sample of the amplified DNA was run on an agarose gel and stained with ethidium bromide to determine the size of the PCR products and the remainder was purified and concentrated using PCR Wizard Prep columns (Promega Corporation).

The purified DNA was cloned into Eco RV-cut Bluescript SK+ vector (Stratagene) which had been T-tailed with Taq Polymerase and the ligated DNA was introduced into *E. coli* DH5α by electroporation. Recombinant clones which had an insert of the predicted size were selected and their DNA sequence was determined by automated sequencing. A putative banana PPO clone (BPO3) was identified based on its homology to known plant PPO genes.

Using this sequence information a specific forward primer (BAN1) and two specific reverse primers (BAN2R and BAN3R) were synthesised:

```
BAN 1:
5'-AGTCATCCACAATGCGGCGCACATG-3';      (SEQ ID NO: 47)

BAN 2R:
5'-CCGCATTGTGGATGACTTCCATCTG-3';      (SEQ ID NO: 44)
and

BAN 3R:
5'-CCAGAATGGGATGGTGAAGGTGTCG-3'.      (SEQ ID NO: 45)
```

To obtain the 3'-end of this banana PPO gene, the first strand cDNA described above was amplified by the same PCR procedure using 1 µM BAN1 primer and 100 nM adapter primer:

```
B25:
5'-GACTCGAGTCGACATCG-3'.              (SEQ ID NO: 49)
```

The DNA was amplified using 25 cycles of denaturation at 94° C. for 1 min, annealing at 55° C. for 1 min, and elongation at 72° C. for 3 min. The amplified DNA was purified using a QIAquick Spin PCR Purification Kit (QIAGEN) and run on a 2% Nusieve GTG (FMC Bioproducts) agarose gel. A 1000 bp fragment was excised from the gel and the DNA was cloned into T-tailed Eco RVcut Bluescript SK+ to yield the 3'-end clone BPO17, which was sequenced and shown to encode the 3'-end of BPO3.

The 5'-end of BPO3 was cloned by a modification of the 5'-RACE procedure originally described by Frohmann. First strand cDNA was synthesised from banana fruit RNA as described above but utilising the banana PPO specific primer BAN2R. The DNA was tailed with Terminal transferase as described in Frohmann and amplified by PCR with BAN3R and B26 primers, each at a final concentration of 1 µM. The DNA was amplified using 30 cycles of denaturation at 94° C. for 1 min, annealing at 55° C. for 1 min, and elongation at 72° C. for 3 min. The amplified DNA was run on a 1.8% Nusieve GTG (FMC Bioproducts) agarose gel and a 700 bp fragment was excised from the gel. The DNA was extracted with a QIAquick Gel Extraction Kit and cloned into T-tailed Eco RV-cut Bluescript SK+ to yield the 5'-end clone BPO26 which was sequenced and shown to encode the 5'-end of BPO3.

The overlapping clones BPO3, BPO17 and BPO26 were fully sequenced in both directions and the sequence of this banana PPO gene (BANPPO1) was derived by combining the sequences (FIG. 11).

In the course of these experiments a number of clones were obtained from the banana fruit cDNA by PCR amplification using the B25 primer with one of the degenerate primers based on conserved sequences in other plant PPO genes: GEN7:5'-GCGAATTCAA[TC]GTIGA[TC][AC]GI-ATGTGG-3' (SEQ ID NO: 33). using the methods described above. Most of these clones were identical to BANPPO1 but one clone, designated BANPPO11, was found to be distinctly different and its sequence is shown in FIG. 12.

EXAMPLE 3

Cloning Banana Peel PPO genes

Total RNA was isolated from the peel of young banana fruit. Fruit tissue (3 g) was frozen and ground to a fine powder in liquid nitrogen with a coffee grinder then added to 20 ml of extraction buffer. (2% hexadecyltrimethylammonium bromide (CTAB), 2% polyvinyl pyrrolidone, 100 mM Tris-CHI, pH 8.0, 25 mM EDTA, 2 M NaCl, 0.05% spermidine, 2% β-mercaptoethanol) at 65° C. The extract was mixed with 20 ml of chloroform/IAA then centrifuged for 20 minutes at 5,000 RPM and the aqueous phase was re-extracted with chloroform/IAA. The aqueous phase was filtered through Miracloth and 0.25 volumes of 10 M LiCl were added then the sample was incubated overnight at 4° C. before centrifuging for 20 minutes at 8,000 RPM. The supernatant was removed and the pellet was resuspended in 0.5 ml of 1 M NaCl, 0.5% SDS, 10 mM Tris, pH 8.0, 1 mM EDTA. The RNA was extracted once with an equal volume of chloroform/IAA and 2 volumes of ethanol was added. After incubation for 40 mins at −70° C. the solution was centrifuged for 15 minutes at 10,000 RPM. The supernatant was removed and the pellet was rinsed with 80% ethanol, drained and dried. The pellet was resuspended in 50 µL of sterile water.

First strand cDNA was synthesised from 10 µg total RNA with reverse transcriptase as described in Ref 2, utilising an oligosaccharide-dT primer adapter (Ref 1):

```
B26:                                  (SEQ ID NO:38)
(5'GACTCGAGTCGACATCGATTTTTTTTTTTTTTTT-3').
```

Oligonucleotide primers were designed based on known plant PPO DNA sequences. Comparison of a number of PPO sequences from a range of different plants allowed identification of the conserved regions of the gene, which are mostly in or near the regions which encode the two copper binding sites, CuA and CuB (2). Forward primers designed around the CuA site (GEN8, GEN9 and GEN 10) and reverse primers designed around the CuB site (REV1 and REV2) were synthesised:

```
GEN8:                                 (SEQ ID NO: 32)
(5'-GCGAATTCGATCCIACITT[TC]GC[GT]TTICC-3')

GEN9:                                 (SEQ ID NO: 34)
(5'-GCGAATTCTICA[TC]TG[TC]GCITA[TC]TG-3')

GEN10:                                (SEQ ID NO: 35)
(5'-GCGAATTCTTICCIT[TA][TC]TGGAA[TC]TGGG-3')

REV1:                                 (SEQ ID NO: 36)
(5'-GCCTGCAGCCACATIC[TG][AG]TCIAC[AG]TT-3')

REV2:                                 (SEQ ID NO: 37)
(5'-GCCTGCAGTT[TC]TC[AG]TC[AG]TAGAA-3')
```

The first strand reaction was amplified by the polymerase chain reaction (PCR) essentially according to the method of Frohman (1) using GEN and REV primers, each at a final concentration of 1 µM (2). Amplification involved an initial program of 2 cycles of denaturation at 94° C. for 1 min, annealing at 37° C. for 2 min, a slow ramp to 72° C. for 3 min, followed by 33 cycles of denaturation at 94° C. for 1 min, annealing at 55° C. for 1 min, and elongation at 72° C. for 3 min. A sample of the amplified DNA was run on an agarose gel and stained with ethidium bromide to determine the size of the PCR products. The remainder was run on a low melting point agarose gel and the bands of interest were excised. DNA was purified from the agarose with a QIAquick PCR Purification kit (Qiagen).

The purified DNA was cloned into Eco-RV-cut Bluescript SK+ vector (Stratagene) which had been T-tailed with Taq Polymerase and the ligated DNA was introduced into *E. coli* DH5α by electroporation. Recombinant clones which had an insert of the predicted size were selected and their DNA sequence was determined by automated sequencing. Two putative banana PPO clones (BPPO2, FIG. 1; and BPPO8, FIG. 2) were identified by their homology to other plant PPO genes.

The 3'-end of BPPO2 was cloned using a primer designed to the sequence of BPPO2:

```
BAN8F (SEQ ID NO: 48):
(5'-GTTGCTCTTCTTAGGCTCGGCTTAC-3')
``` at a final concentration of 1 µM and a B25 adaptor primer:

```
B25:
(5'GACTCGAGTCGACATCGA-3'):   (SEQ ID NO: 49)
``` at a final concentration of 1 µM (ref 1). Amplification involved 35 cycles of denaturation at 94° C. for 1 min, annealing at 55° C. for 1 min, and elongation at 72° C. for 3 min. A sample of the amplified DNA was run on an agarose gel and stained with ethidium bromide to determine the size of the PCR products. The remainder was run on a low melting point agarose gel and the bands of interest were excised. DNA was purified from the agarose with a QIAquick PCR Purification kit (Qiagen).

The purified DNA was cloned into Eco RV-cut Bluescript SK+ vector (Stratagene) which has been T-tailed with Taq Polymerase and the ligated DNA was introduced into E. coli DH5α by electroporation. Recombinant clones which had an insert of the predicted size (1150 bp) were selected and their DNA sequence was determined by automated sequencing. Two putative banana PPO clones (BANPPO34, FIG. 3; and BANPPO35, FIG. 4) were identified based on their homology to known plant PPO genes. The sequences of BANPPO34 and BPPO2 were identical.

EXAMPLE 4

Cloning Tobacco Leaf PPO genes

Total RNA was isolated from young leaves (1-3 cm long) of glasshouse grown plants. Approximately 2 g of frozen leaf material was ground to a fine powder in liquid nitrogen then extracted in 15 ml of extraction buffer (50 mM Tris-HCl, pH 9.0, 150 mM LiCl, 5 mM EDTA, 5% SDS and 0.6% β-mercaptoethanol) by shaking vigorously in a 50 ml screw cap tube for 1-2 minutes. Approximately 15 ml of phenol/chloroform/IAA (25:24:1) was added and the homogenate mixed then centrifuged for 15 minutes at 5,000 RPM, 4° C. The upper aqueous phase was removed and re-extracted twice with phenol/chloroform/IAA and then once with chloroform/IAA and then centrifuged for 10 minutes at 5,000 RPM, 4° C. The supernatant was removed, LiCl was added to a final concentration of 2 M and the mixture was incubated overnight at 4° C. After centrifuging for 10 minutes at 8,000 RPM, 4° C. the supernatant was removed and the pellet was resuspended in 6 ml of 0.4 M LiCl then 2 ml of 8M LiCl was added and the mixture was incubated overnight at 4° C. The mixture was centrifuged for 10 minutes at 8,000 RPM, 4° C., the supernatant was removed and the pellet was resuspended in 0.5 ml of sterile water and centrifuged briefly to remove any insoluble material.

mRNA was isolated from the total RNA using a PolyATtract kit (Promega). First strand cDNA was synthesised from 10 µg total RNA or 2 µg mRNA with reverse transcriptase as described in Ref 2, utilising an oligo-dT primer adapter (Ref 1):

```
                                            (SEQ ID NO:38)
B26: 5'-GACTCGAGTCGACATCGATTTTTTTTTTTTTTTT-3'.
```

The first strand reaction was amplified by the polymerase chain reaction (PCR) essentially according to the method of Frohman (1) using GEN and REV primers described in Example 1, each at a final concentration of 1 µM (2). Amplification involved an initial program of 2 cycles of denaturation at 94° C. for 1 min, annealing at 37° C. for 2 min, a slow ramp to 72° C. over 2 min and elongation at 72° C. for 3 min, followed by 28 cycles of denaturation at 94° C. for 1 min, annealing at 55° C. for 1 min, and elongation at 72° C. for 3 min. A sample of the amplified DNA was run on an agarose gel and stained with ethidium bromide to determine the size of the PCR products. The remainder was run on a low melting point agarose gel and the bands of interest were excised. DNA was purified from the agarose with a QIAquick PCR Purification kit (Qiagen).

The purified DNA was cloned into Eco RV-cut Bluescript SK+ vector (Stratagene) which had been T-tailed with Taq Polymeras and the ligated DNA was introduced into E. coli DH5α by electroporation. Recombinant clones which had an insert of the predicted size were selected and their DNA sequence was determined by automated sequencing. Three putative tobacco PPO clones (TOBPPO6, FIG. 5; TOBPPO25, FIG. 6; and TOBPPO26, FIG. 7) were identified based on their homologies to known PPO genes.

EXAMPLE 5

Cloning Pineapple PPO Genes

Mature pineapple fruit were treated to induce blackheart disorder by holding the fruit for 17 days at 12° C. then for 4 days at 25° C. Flesh showing blackheart symptoms was dissected from the fruit, frozen in liquid nitrogen and ground to a fine powder in a pre-cooled coffee grinder. To isolate total RNA 10 g of the powder was ground in a mortar and pestle then extracted with 30 ml of homogenisation buffer (100 mM Tris-HCl, pH9.0, 200 mM NaCl, 15 mM EDTA, 0.5% sarkosyl and 1% β-mercaptoethanol), 30 ml of phenol and 6 ml of chloroform/IAA. The mixture was stirred in a beaker, 2.1 ml of 3M NaAc (pH 5.2) was added and the mixture was kept on ice for 15 minutes then centrifuged for 15 minutes at 8,000 RPM, 4° C. The upper aqueous phase was removed and an equal volume of isopropanol was added. The mixture was incubated for 30 minutes at −70° C. then centrifuged for 20 minutes at 8,000 RPM, 4° C. in Corex tubes. The supernatant was removed and the pellet was rinsed with 70% ethanol and centrifuged for 5 minutes at 8,000 RPM, 4° C. The ethanol was removed and the pellet was air dried then resuspended in 0.75 ml sterile water and centrifuged to remove any insoluble material. LiCl was added to a final concentration of 3 M and the mixture was incubated overnight at −20° C. then centrifuged for 30 minutes at 15,000 RPM, 4° C. The pellet was rinsed with 70% ethanol, centrifuged briefly, drained and air dried. The pellet was resuspended in 75 µl sterile water and centrifuged to remove any insoluble material.

Oligonucleotide primers were designed based on known plant PPO DNA sequences. Comparison of a number of PPO sequences from a range of different plants allowed identification of the conserved regions of the gene, which are mostly in or near the regions which encode the two copper binding sites, CuA and CuB. Forward primers designed around the CuA site (GEN8, GEN9 and GEN 10) and reverse primers designed around the CuB site (REV1 and REV2) were synthesised:

```
GEN8:                                    (SEQ ID NO: 32)
(5'-GCGAATTCGATCCIACITT[TC]GC[GT]TTICC-3')

GEN9:                                    (SEQ ID NO: 34)
(5'-GCGAATTCTICA[TC]TG[TC]GCITA[TC]TG-3')

GEN10:                                   (SEQ ID NO: 35)
(5'-GCGAATTCTTICCIT[TA][TC]TGGAA[TC]TGGG-3')

REV1:                                    (SEQ ID NO: 36)
(5'-GCCTGCAGCCACATIC[TG][AG]TCIAC[AG]TT-3')

REV2:                                    (SEQ ID NO: 37)
(5'-GCCTGCAGTT[TC]TC[AG]TC[AG]TAGAA-3')
```

First strand cDNA was synthesised from 10 μg total RNA with reverse transcriptase as described in Ref 2, utilising the REV2 primer:

```
REV2:                                    (SEQ ID NO: 37)
(5'-GCCTGCAGTT[TC]TC[AG]TC[AG]TAGAA-3')
```

The first strand reaction was amplified by the polymerase chain reaction (PCR) essentially according to the method of Frohman (1) using the GEN and REV primers described in Example 1, each at a final concentration of 1 μM (2). Amplification involved an initial program of 2 cycles of denaturation at 94° C. for 1 min, annealing at 37° C. for 2 min, a slow ramp to 72° C. over 2 min and elongation at 72° C. for 3 min, followed by 33 cycles of denaturation at 94° C. for 1 min, annealing at 55° C. for 1 min, and elongation at 72° C. for 3 min.

A sample of the amplified DNA was run on an agarose gel and stained with ethidium bromide to determine the size of the PCR products. The remainder was run on a low melting point agarose gel and the bands of interest were excised. DNA was purified from the agarose with a QIAquick PCR Purification kit (Qiagen). The purified DNA was cloned into Eco RV-cut Bluescript SK+ vector (Stratagene) which had been T-tailed with Taq Polymerase and the ligated DNA was introduced into E. coli DH5α by electroporation. Recombinant clones which had an insert of the predicted size were selected and their DNA sequence was determined by automated sequencing. A putative pineapple PPO clone (PINPPO20; FIG. 8) was identified based on its homology to known PPO genes.

First strand cDNA was also synthesised from 10 μg total RNA with reverse transcriptase as described in Dry, I. B. and Robinson, S. P (1994), utilising an oligo-dT primer adapter (Ref 1):

```
B26:                                     (SEQ ID NO: 38)
5'-GACTCGAGTCGACATCGATTTTTTTTTTTTTTTT-3'.
```

This first strand reaction was amplified by the polymerase chain reaction (PCR) essentially according to the method of Frohman, M. A. (1990) using GEN9 and GEN10 primers:

```
GEN9:                                    (SEQ ID NO: 34)
(5'-GCGAATTCTICA[TC]TG[TC]GCITA[TC]TG-3')
```

```
-continued
GEN10:                                   (SEQ ID NO: 35)
(5'-GCGAATTCTTICCIT[TA][TC]TGGAA[TC]TGGG-3')
``` at a final concentration of 1 μM and a B25 adaptor primer:

```
B25:
(5'-GACTCGAGTCGACATCGA-3').    (SEQ ID NO: 49)
``` at a final concentration of 0.1 μM (Frohman, M. A. (1990); Dry, I. B. and Robinson, S. P. (1994)) Amplification involved a program of 33 cycles of denaturation at 94° C. for 1 min, annealing at 55° C. for 1 min, and elongation at 72° C. for 3 min.

A sample of the amplified DNA was run on an agarose gel and stained with ethidium bromide to determine the size of the PCR products. The remainder was run on a low melting point agarose gel and the bands of interest were excised. DNA was purified from the agarose with a QIAquick PCR Purification kit (Qiagen).

The purified DNA was cloned into Eco RV-cut Bluescript SK+ vector (Stratagene) which had been T-tailed with Taq Polymerase and the ligated DNA was introduced into E. coli DH5α by electroporation. Recombinant clones which had an insert of the predicted size were selected and their DNA sequence was determined by automated sequencing. Two putative pineapple PPO clones (PINPPO1, FIG. 13; and PINPPO2, FIG. 9 were identified based on their homologies to known PPO genes. The sequence of PINPPO1 was nearly identical to that of PINPPO20.

The 5'-end of PINPPO1 was obtained using a 5'-RACE system for rapid amplification of cDNA ends, Version 2.0, from GIBCO-BRL, according to the manufacturer's instructions. Specific oligonucleotide primers based on the sequences of PINPPO1 and PINPPO2 were used:

```
PINE 1:
5'-ATATCACCTGTCGGTACATGACGGC-3':    (SEQ ID NO: 39)

PINE 2:
5'-GTGCCATTGTAGTCGAGGTCAATCA-3':    (SEQ ID NO: 40)
```

A number of clones were sequenced and one, 5PINA (FIG. 14), was found to be nearly identical to PINPPO1 (FIG. 13) in the overlapping regions.

A full-length pineapple cDNA clone was isolated using a primer designed to the 5'-end sequence of 5PINA:

```
5PIN1:                                   (SEQ ID NO: 41)
(5'-CCAGTGCCTGGTTTAGGTGTATTCAC-3'):
```

Primers designed to the 5'-end of the pineapple PPO gene was used with the B25 adaptor primer as described above to amplify cDNA prepared from blackheart-induced pineapple fruit RNA. Amplification involved a program of 33 cycles of denaturation at 94° C. for 1 min, annealing at 55° C. for 1 min, and elongation at 72° C. for 3 min.

A sample of the amplified DNA was run on an agarose gel and stained with ethidium bromide to determine the size of the PCR products. The remainder was run on a low melting point agarose gen and the bands of interest were excised. DNA was purified from the agarose with a QIAquick PCR Purification kit (Qiagen).

The purified DNA was cloned into Eco RV-cut Bluescript SK+ vector (Stratagene) which had been T-tailed with Taq Polymerase and the ligated DNA was introduced into *E. coli* DH5α by electroporation. Recombinant clones which had an insert of the predicted size (2.2 kbp) were selected and their DNA sequence was determined by automated sequencing. A pineapple PPO clone (PINPPOFL; FIG. 10) was identified based on its homology to the PINPPO20 (FIG. 8), PINPPO1 (FIG. 13) and 5 PINA (FIG. 14) clones. The sequence of PINPPOFL was found to be nearly identical to that of PINPPO20, PINPPO1 and 5PINA in the overlapping regions.

REFERENCES

1. Frohman, M A (1990) in "PCR Protocols: A guide to Methods and Applications" (M A Innis, D H Gelfrand, J J Sninsky and T J White, eds) Academic Press, New York, pp 28-38.
2. Dry, I B and Robinson, S P (1994) "Molecular cloning and characterisation of grape berry polyphenol oxidase". *Plant Mol. Biol.* 26, 495-502.

I claim:

1. An isolated nucleic acid molecule that encodes a PPO polypeptide of lettuce comprising:
   (i) the nucleotide sequence set forth in SEQ ID NO: 29;
   (ii) a nucleotide sequence that encodes the amino acid sequence set forth in SEQ ID NO: 30;
   (iii) a nucleotide sequence that encodes a copper-binding site of the amino acid sequence of (ii); or
   (iv) the nucleotide sequence that is complementary to (i) or (ii) or (iii).

2. The isolated nucleic acid molecule of claim 1, comprising:
   (i) the nucleotide sequence set forth in SEQ ID NO: 29;
   (ii) a nucleotide sequence that encodes the amino acid sequence set forth in SEQ ID NO: 30; or
   (iii) the nucleotide sequence that is complementary to (i) or (ii).

3. A recombinant vector comprising a nucleic acid molecule comprising:
   (i) the nucleotide sequence set forth in SEQ ID NO: 29;
   (ii) a nucleotide sequence that encodes the amino acid sequence set forth in SEQ ID NO: 30;
   (iii) a nucleotide sequence that encodes a copper-binding site of the amino acid sequence of (ii); or
   (iv) the nucleotide sequence that is complementary to (i) or (ii) or (iii), within the vector molecule.

4. The recombinant vector of claim 3 wherein the vector is a plasmid expression vector.

5. The recombinant vector of claim 4 wherein the plasmid expression vector is Bluescript SK+.

6. The recombinant vector of claim 3, wherein the vector is a binary vector suitable for introducing into a plant cell, tissue or organ.

7. The recombinant vector of claim 3, wherein the vector is capable of being replicated and the PPO-encoding nucleic acid is capable of being transcribed and translated in a unicellular organism or in a plant.

8. A method of increasing the level of PPO activity in a plant, cell, tissue or organ thereof, the method comprising:
   (a) introducing into the plant, cell, tissue or organ thereof a nucleic acid molecule encoding PPO polypeptide of lettuce comprising:
      (i) the nucleotide sequence set forth in SEQ ID NO: 29;
      (ii) a nucleotide sequence that encodes the amino acid sequence set forth in SEQ ID NO: 30;
      (iii) a nucleotide sequence that encodes a copper-binding site of the amino acid sequence of (ii), and
   (b) expressing the nucleic acid molecule to produce an enzymatically-active PPO polypeptide.

9. A method of decreasing the level of PPO activity in a lettuce plant, cell, tissue or organ thereof, the method comprising introducing a nucleic acid which hybridizes to a nucleic acid molecule in the lettuce plant, cell, tissue or organ thereof, comprising:
   (i) the nucleotide sequence set forth in SEQ ID NO: 29;
   (ii) a nucleotide sequence that encodes the amino acid sequence set forth in SEQ ID NO: 30;
   (iii) a nucleotide sequence that encodes a copper-binding site of the amino acid sequence of (ii); or
   (iv) the nucleotide sequence that is complementary to (i) or (ii) or (iii).

* * * * *

SEQUENCE LISTING

<160> NUMBER OF SEQ ID NOS: 49

<210> SEQ ID NO 1
<211> LENGTH: 582
<212> TYPE: DNA
<213> ORGANISM: banana
<220> FEATURE:
<221> NAME/KEY: CDS
<222> LOCATION: (1)..(582)

<400> SEQUENCE: 1

```
cac tgt gcg tat tgt gat ggc gcc tac gac cag atc ggc ttc ccc aac        48
His Cys Ala Tyr Cys Asp Gly Ala Tyr Asp Gln Ile Gly Phe Pro Asn
  1               5                  10                  15 ctc gag ctc caa gtc cac aac tcc tgg ctc ttc cct tgg cac cgc            96
Leu Glu Leu Gln Val His Asn Ser Trp Leu Phe Phe Pro Trp His Arg
             20                  25                  30 ttc tac ctc tac ttc cac gag agg atc ctc gga aag ctc ata ggc gac       144
Phe Tyr Leu Tyr Phe His Glu Arg Ile Leu Gly Lys Leu Ile Gly Asp
         35                  40                  45 gac act ttc gcc ctc cct ttc tgg aac tgg gac gcg ccc ggc ggc atg       192
Asp Thr Phe Ala Leu Pro Phe Trp Asn Trp Asp Ala Pro Gly Gly Met
     50                  55                  60 aag ctg ccg tcg atc tac gcc gac cct tcg tcc tcg ctc tat gac aag       240
Lys Leu Pro Ser Ile Tyr Ala Asp Pro Ser Ser Ser Leu Tyr Asp Lys
 65                  70                  75                  80 ttt cgc gac gcc aag cac cag ccg cca gtc ctc gtc gac ctc gac tac       288
Phe Arg Asp Ala Lys His Gln Pro Pro Val Leu Val Asp Leu Asp Tyr
                 85                  90                  95 aac gga acc gac cct agt ttc acc gac gca gag cag atc gat cag aac       336
Asn Gly Thr Asp Pro Ser Phe Thr Asp Ala Glu Gln Ile Asp Gln Asn
            100                 105                 110 ctc aag atc atg tac cgg cag gtg atc tcc aac ggc aag acg ccg ttg       384
Leu Lys Ile Met Tyr Arg Gln Val Ile Ser Asn Gly Lys Thr Pro Leu
        115                 120                 125 ctc ttc tta ggc tcg gct tac cgt gcc ggc gac aac cca aac ccc ggc       432
Leu Phe Leu Gly Ser Ala Tyr Arg Ala Gly Asp Asn Pro Asn Pro Gly
    130                 135                 140 gcg ggc tcg ctc gag aac ata cca cac ggc ccc gtc cac ggg tgg act       480
Ala Gly Ser Leu Glu Asn Ile Pro His Gly Pro Val His Gly Trp Thr
145                 150                 155                 160 ggc gac aga agc caa ccc aat ctc gag gac atg ggc aac ttc tac tcc       528
Gly Asp Arg Ser Gln Pro Asn Leu Glu Asp Met Gly Asn Phe Tyr Ser
                165                 170                 175 gcg ggg cgc gac cct atc ttc ttc gcc cac cat tca aat gtc gat cgc       576
Ala Gly Arg Asp Pro Ile Phe Phe Ala His His Ser Asn Val Asp Arg
            180                 185                 190 atg tgg                                                                582
Met Trp
```

<210> SEQ ID NO 2
<211> LENGTH: 194
<212> TYPE: PRT
<213> ORGANISM: banana

<400> SEQUENCE: 2

```
His Cys Ala Tyr Cys Asp Gly Ala Tyr Asp Gln Ile Gly Phe Pro Asn
 1               5                  10                  15

Leu Glu Leu Gln Val His Asn Ser Trp Leu Phe Pro Trp His Arg
                20                  25                  30

Phe Tyr Leu Tyr Phe His Glu Arg Ile Leu Gly Lys Leu Ile Gly Asp
                35                  40                  45

Asp Thr Phe Ala Leu Pro Phe Trp Asn Trp Asp Ala Pro Gly Gly Met
            50                  55                  60

Lys Leu Pro Ser Ile Tyr Ala Asp Pro Ser Ser Leu Tyr Asp Lys
 65                  70                  75                  80

Phe Arg Asp Ala Lys His Gln Pro Pro Val Leu Val Asp Leu Asp Tyr
                    85                  90                  95

Asn Gly Thr Asp Pro Ser Phe Thr Asp Ala Glu Gln Ile Asp Gln Asn
                100                 105                 110

Leu Lys Ile Met Tyr Arg Gln Val Ile Ser Asn Gly Lys Thr Pro Leu
            115                 120                 125

Leu Phe Leu Gly Ser Ala Tyr Arg Ala Gly Asp Asn Pro Asn Pro Gly
        130                 135                 140

Ala Gly Ser Leu Glu Asn Ile Pro His Gly Pro Val His Gly Trp Thr
145                 150                 155                 160

Gly Asp Arg Ser Gln Pro Asn Leu Glu Asp Met Gly Asn Phe Tyr Ser
                165                 170                 175

Ala Gly Arg Asp Pro Ile Phe Phe Ala His His Ser Asn Val Asp Arg
                180                 185                 190

Met Trp
```

<210> SEQ ID NO 3
<211> LENGTH: 426
<212> TYPE: DNA
<213> ORGANISM: banana
<220> FEATURE:
<221> NAME/KEY: CDS
<222> LOCATION: (1)..(426)

<400> SEQUENCE: 3

```
ttg ccg ttt tgg aat tgg gac gcg ccc ggc ggc atg aag ctg ccg tcg    48
Leu Pro Phe Trp Asn Trp Asp Ala Pro Gly Gly Met Lys Leu Pro Ser
 1               5                  10                  15 atc tac gcc gac cct tcg tcc tcg ctc tat gac aag ttt cgc gac gcc    96
Ile Tyr Ala Asp Pro Ser Ser Ser Leu Tyr Asp Lys Phe Arg Asp Ala
                20                  25                  30 aag cac cag ccg ccg gtc ctc gtc gac ctc gac tac aac gga acc gac   144
Lys His Gln Pro Pro Val Leu Val Asp Leu Asp Tyr Asn Gly Thr Asp
            35                  40                  45 cct agt ttc acc gac gca gag cag atc gat cag aac ctc aag atc atg   192
Pro Ser Phe Thr Asp Ala Glu Gln Ile Asp Gln Asn Leu Lys Ile Met
        50                  55                  60 tac cgg cag gtg atc tcc aac ggc aag acg ccg ttg ctc ttc tta ggc   240
Tyr Arg Gln Val Ile Ser Asn Gly Lys Thr Pro Leu Leu Phe Leu Gly
 65                  70                  75                  80 tcg gct tac cgt gcc ggc gac aac cca aac ccc ggc gcg ggc tcg ctc   288
```

```
Ser Ala Tyr Arg Ala Gly Asp Asn Pro Asn Pro Gly Ala Gly Ser Leu
             85                  90                  95 gag aac ata cca cac ggc ccc gtc cac ggg tgg act ggc gac aga agc    336
Glu Asn Ile Pro His Gly Pro Val His Gly Trp Thr Gly Asp Arg Ser
            100                 105                 110 caa ccc aat ctc gag gac atg ggc aac ttc tac tcc gcg ggg cgc gac    384
Gln Pro Asn Leu Glu Asp Met Gly Asn Phe Tyr Ser Ala Gly Arg Asp
        115                 120                 125 cct atc ttc ttc gcc cac cat tca aat gtc gat agc atg tgg            426
Pro Ile Phe Phe Ala His His Ser Asn Val Asp Ser Met Trp
    130                 135                 140
```

<210> SEQ ID NO 4
<211> LENGTH: 142
<212> TYPE: PRT
<213> ORGANISM: banana

<400> SEQUENCE: 4

```
Leu Pro Phe Trp Asn Trp Asp Ala Pro Gly Gly Met Lys Leu Pro Ser
 1               5                  10                  15

Ile Tyr Ala Asp Pro Ser Ser Ser Leu Tyr Asp Lys Phe Arg Asp Ala
            20                  25                  30

Lys His Gln Pro Pro Val Leu Val Asp Leu Asp Tyr Asn Gly Thr Asp
        35                  40                  45

Pro Ser Phe Thr Asp Ala Glu Gln Ile Asp Gln Asn Leu Lys Ile Met
    50                  55                  60

Tyr Arg Gln Val Ile Ser Asn Gly Lys Thr Pro Leu Leu Phe Leu Gly
 65                  70                  75                  80

Ser Ala Tyr Arg Ala Gly Asp Asn Pro Asn Pro Gly Ala Gly Ser Leu
             85                  90                  95

Glu Asn Ile Pro His Gly Pro Val His Gly Trp Thr Gly Asp Arg Ser
            100                 105                 110

Gln Pro Asn Leu Glu Asp Met Gly Asn Phe Tyr Ser Ala Gly Arg Asp
        115                 120                 125

Pro Ile Phe Phe Ala His His Ser Asn Val Asp Ser Met Trp
    130                 135                 140
```

<210> SEQ ID NO 5
<211> LENGTH: 925
<212> TYPE: DNA
<213> ORGANISM: banana
<220> FEATURE:
<221> NAME/KEY: CDS
<222> LOCATION: (2)..(853)

<400> SEQUENCE: 5

```
g ttg ctc ttc tta ggc tcg gct tac cgt gcc ggc gac aac cca aac ccc    49
  Leu Leu Phe Leu Gly Ser Ala Tyr Arg Ala Gly Asp Asn Pro Asn Pro
   1               5                  10                  15 ggc gcg ggc tcg ctc gag aac ata cca cac ggc ccc gtc cac ggg tgg     97
Gly Ala Gly Ser Leu Glu Asn Ile Pro His Gly Pro Val His Gly Trp
             20                  25                  30 act ggc gac aga aac caa ccc aat ctc gag gac atg ggc aac ttc tac    145
Thr Gly Asp Arg Asn Gln Pro Asn Leu Glu Asp Met Gly Asn Phe Tyr
         35                  40                  45 tcc gcg ggg cgc gac cct atc ttc ttc gcc cac cat tca aac gtc gac    193
Ser Ala Gly Arg Asp Pro Ile Phe Phe Ala His His Ser Asn Val Asp
     50                  55                  60 cgc atg tgg tac ttg tgg aag aag ctc ggc ggg aag cat cag gac ttt    241
Arg Met Trp Tyr Leu Trp Lys Lys Leu Gly Gly Lys His Gln Asp Phe
 65                  70                  75                  80
```

|  | | | | | | | | | | | | | | | |
|---|---|---|---|---|---|---|---|---|---|---|---|---|---|---|---|
| | | 65 | | | 70 | | | | 75 | | | | 80 | | |
| aac | gat | aag | gac | tgg | ctc | aac | acc | acc | ttc | ctc | ttc | tac | gac | gag | aat | 289 |
| Asn | Asp | Lys | Asp | Trp | Leu | Asn | Thr | Thr | Phe | Leu | Phe | Tyr | Asp | Glu | Asn |
| | | | | 85 | | | | | 90 | | | | | 95 | |
| gct | gac | tta | gtt | cga | gtc | acc | ctc | aag | gac | tgc | ttg | cag | ccg | gag | tgg | 337 |
| Ala | Asp | Leu | Val | Arg | Val | Thr | Leu | Lys | Asp | Cys | Leu | Gln | Pro | Glu | Trp |
| | | | 100 | | | | | 105 | | | | | 110 | | |
| ctt | cgt | tac | gat | tac | caa | gac | gtc | gag | atc | ccg | tgg | ctg | aag | acc | cgg | 385 |
| Leu | Arg | Tyr | Asp | Tyr | Gln | Asp | Val | Glu | Ile | Pro | Trp | Leu | Lys | Thr | Arg |
| | | | | 115 | | | | | 120 | | | | | 125 | |
| ccg | act | ccc | aaa | gcc | ttg | aag | gcg | cag | aaa | acc | gca | gcg | aaa | aca | ctg | 433 |
| Pro | Thr | Pro | Lys | Ala | Leu | Lys | Ala | Gln | Lys | Thr | Ala | Ala | Lys | Thr | Leu |
| | | | 130 | | | | | 135 | | | | | 140 | | |
| aaa | gct | aca | gca | gag | acg | ccg | ttc | ccg | gtg | acg | ctg | caa | tcc | gcg | gtg | 481 |
| Lys | Ala | Thr | Ala | Glu | Thr | Pro | Phe | Pro | Val | Thr | Leu | Gln | Ser | Ala | Val |
| 145 | | | | | 150 | | | | | 155 | | | | | 160 |
| agc | acg | acg | gtg | agg | agg | ccc | aag | gta | tcg | agg | agc | ggc | aag | gag | aag | 529 |
| Ser | Thr | Thr | Val | Arg | Arg | Pro | Lys | Val | Ser | Arg | Ser | Gly | Lys | Glu | Lys |
| | | | | 165 | | | | | 170 | | | | | 175 | |
| gaa | gag | gaa | gag | gag | gtc | ctc | atc | gtg | gag | ggg | atc | gag | ttc | gac | cgc | 577 |
| Glu | Glu | Glu | Glu | Glu | Val | Leu | Ile | Val | Glu | Gly | Ile | Glu | Phe | Asp | Arg |
| | | | 180 | | | | | 185 | | | | | 190 | | |
| gac | tac | ttc | ata | aag | ttc | gac | gtc | ttc | gtg | aac | gcc | acc | gag | ggt | gag | 625 |
| Asp | Tyr | Phe | Ile | Lys | Phe | Asp | Val | Phe | Val | Asn | Ala | Thr | Glu | Gly | Glu |
| | | | | 195 | | | | | 200 | | | | | 205 | |
| ggc | atc | acg | ccg | ggc | gcc | agc | gag | ttc | gcg | ggc | agc | ttc | gtc | aac | gtc | 673 |
| Gly | Ile | Thr | Pro | Gly | Ala | Ser | Glu | Phe | Ala | Gly | Ser | Phe | Val | Asn | Val |
| | | | 210 | | | | | 215 | | | | | 220 | | |
| ccg | cac | aag | cac | aag | cac | agc | aag | aag | gag | aag | aag | ctg | aag | acg | agg | 721 |
| Pro | His | Lys | His | Lys | His | Ser | Lys | Lys | Glu | Lys | Lys | Leu | Lys | Thr | Arg |
| 225 | | | | | 230 | | | | | 235 | | | | | 240 |
| ctc | tgc | ctg | ggg | atc | act | gac | ctg | ctc | gag | gac | atc | ggg | gcg | gag | gac | 769 |
| Leu | Cys | Leu | Gly | Ile | Thr | Asp | Leu | Leu | Glu | Asp | Ile | Gly | Ala | Glu | Asp |
| | | | | 245 | | | | | 250 | | | | | 255 | |
| gac | gac | agc | gtg | ctc | gtc | acc | atc | gtc | ccg | aaa | gcc | gga | aag | ggc | aag | 817 |
| Asp | Asp | Ser | Val | Leu | Val | Thr | Ile | Val | Pro | Lys | Ala | Gly | Lys | Gly | Lys |
| | | | 260 | | | | | 265 | | | | | 270 | | |
| gtg | tcg | gtc | gcc | ggc | ctc | cgc | atc | gat | ttc | cca | aat | tgaagtaata | | | | 863 |
| Val | Ser | Val | Ala | Gly | Leu | Arg | Ile | Asp | Phe | Pro | Asn |
| | | | | 275 | | | | | 280 | | | ctatatattt ctactaccta tcaaggaaaa taaaagccgc accatcgtaa caaaaaaaaa 923 aa 925

<210> SEQ ID NO 6
<211> LENGTH: 284
<212> TYPE: PRT
<213> ORGANISM: banana

<400> SEQUENCE: 6

| Leu | Leu | Phe | Leu | Gly | Ser | Ala | Tyr | Arg | Ala | Gly | Asp | Asn | Pro | Asn | Pro |
|---|---|---|---|---|---|---|---|---|---|---|---|---|---|---|---|
| 1 | | | | 5 | | | | | 10 | | | | | 15 | |

| Gly | Ala | Gly | Ser | Leu | Glu | Asn | Ile | Pro | His | Gly | Pro | Val | His | Gly | Trp |
|---|---|---|---|---|---|---|---|---|---|---|---|---|---|---|---|
| | | | 20 | | | | | 25 | | | | | 30 | | |

| Thr | Gly | Asp | Arg | Asn | Gln | Pro | Asn | Leu | Glu | Asp | Met | Gly | Asn | Phe | Tyr |
|---|---|---|---|---|---|---|---|---|---|---|---|---|---|---|---|
| | | | | 35 | | | | | 40 | | | | | 45 | |

| Ser | Ala | Gly | Arg | Asp | Pro | Ile | Phe | Phe | Ala | His | His | Ser | Asn | Val | Asp |
|---|---|---|---|---|---|---|---|---|---|---|---|---|---|---|---|
| | | | 50 | | | | | 55 | | | | | 60 | | |

| Arg | Met | Trp | Tyr | Leu | Trp | Lys | Lys | Leu | Gly | Gly | Lys | His | Gln | Asp | Phe |
|---|---|---|---|---|---|---|---|---|---|---|---|---|---|---|---|

```
                65                  70                  75                  80
Asn Asp Lys Asp Trp Leu Asn Thr Thr Phe Leu Phe Tyr Asp Glu Asn
                    85                  90                  95
Ala Asp Leu Val Arg Val Thr Leu Lys Asp Cys Leu Gln Pro Glu Trp
                   100                 105                 110
Leu Arg Tyr Asp Tyr Gln Asp Val Glu Ile Pro Trp Leu Lys Thr Arg
                   115                 120                 125
Pro Thr Pro Lys Ala Leu Lys Ala Gln Lys Thr Ala Ala Lys Thr Leu
                   130                 135                 140
Lys Ala Thr Ala Glu Thr Pro Phe Pro Val Thr Leu Gln Ser Ala Val
145                 150                 155                 160
Ser Thr Thr Val Arg Arg Pro Lys Val Ser Arg Ser Gly Lys Glu Lys
                   165                 170                 175
Glu Glu Glu Glu Glu Val Leu Ile Val Glu Gly Ile Glu Phe Asp Arg
                   180                 185                 190
Asp Tyr Phe Ile Lys Phe Asp Val Phe Val Asn Ala Thr Glu Gly Glu
                   195                 200                 205
Gly Ile Thr Pro Gly Ala Ser Glu Phe Ala Gly Ser Phe Val Asn Val
                   210                 215                 220
Pro His Lys His Lys His Ser Lys Lys Glu Lys Lys Leu Lys Thr Arg
225                 230                 235                 240
Leu Cys Leu Gly Ile Thr Asp Leu Leu Glu Asp Ile Gly Ala Glu Asp
                   245                 250                 255
Asp Asp Ser Val Leu Val Thr Ile Val Pro Lys Ala Gly Lys Gly Lys
                   260                 265                 270
Val Ser Val Ala Gly Leu Arg Ile Asp Phe Pro Asn
                   275                 280

<210> SEQ ID NO 7
<211> LENGTH: 960
<212> TYPE: DNA
<213> ORGANISM: banana
<220> FEATURE:
<221> NAME/KEY: CDS
<222> LOCATION: (2)..(853)

<400> SEQUENCE: 7 g ttg ctc ttc tta ggc tcg gct tac cgt gcc ggt gac cag cct aac ccc    49
  Leu Leu Phe Leu Gly Ser Ala Tyr Arg Ala Gly Asp Gln Pro Asn Pro
   1               5                  10                  15 ggc gcg gga tcc atc gag aac atg ccg cac aac aac gtg cac ttg tgg    97
Gly Ala Gly Ser Ile Glu Asn Met Pro His Asn Asn Val His Leu Trp
             20                  25                  30 acc ggc gac cgc acc cag ccc aac ttc gag aac atg ggc acc ttc tac   145
Thr Gly Asp Arg Thr Gln Pro Asn Phe Glu Asn Met Gly Thr Phe Tyr
         35                  40                  45 gcg gcg gcg cgc gac ccc atc ttc ttc gcc cac cac gcc aac atc gac   193
Ala Ala Ala Arg Asp Pro Ile Phe Phe Ala His His Ala Asn Ile Asp
     50                  55                  60 cga atg tgg tac ctg tgg aag aag ctc agc agg aag cac cag gac ttc   241
Arg Met Trp Tyr Leu Trp Lys Lys Leu Ser Arg Lys His Gln Asp Phe
 65                  70                  75                  80 aat gac tcg gac tgg ctc aaa gct tcc ttc ctc ttc tac gac gag aac   289
Asn Asp Ser Asp Trp Leu Lys Ala Ser Phe Leu Phe Tyr Asp Glu Asn
                 85                  90                  95 gcc gac tta gtt cgg gtc acg gtc aag gac tgc ttg gag acc gag tgg   337
Ala Asp Leu Val Arg Val Thr Val Lys Asp Cys Leu Glu Thr Glu Trp
            100                 105                 110
```

-continued

```
ctg cgc tac acg tac caa gac gtg aag atc cca tgg gcg aac acc cga      385
Leu Arg Tyr Thr Tyr Gln Asp Val Lys Ile Pro Trp Ala Asn Thr Arg
            115                 120                 125 ccg act ccc aag ctc gcc aag gcg agg aaa gcc ggc agc aga tcg ctg      433
Pro Thr Pro Lys Leu Ala Lys Ala Arg Lys Ala Gly Ser Arg Ser Leu
130                 135                 140 aaa gcc acc gcg gag gtg cag ttc cct gtg acg ctg gaa tcc ccg gtc      481
Lys Ala Thr Ala Glu Val Gln Phe Pro Val Thr Leu Glu Ser Pro Val
145                 150                 155                 160 aaa gtg acg gtg aag agg ccc aag gtg ggg agg agc ggc aag gag aag      529
Lys Val Thr Val Lys Arg Pro Lys Val Gly Arg Ser Gly Lys Glu Lys
                165                 170                 175 gaa gat gag gag gag ata ctc ata gtg gag ggg atc gag ttc gac cgc      577
Glu Asp Glu Glu Glu Ile Leu Ile Val Glu Gly Ile Glu Phe Asp Arg
            180                 185                 190 gac tac ttc atc aag ttc gac gtc ttc gtg aac gcg acg gag ggc gac      625
Asp Tyr Phe Ile Lys Phe Asp Val Phe Val Asn Ala Thr Glu Gly Asp
        195                 200                 205 ggc atc acg gcc ggg gcc agt gag ttc gcc ggc agc ttc gtg aac gtc      673
Gly Ile Thr Ala Gly Ala Ser Glu Phe Ala Gly Ser Phe Val Asn Val
210                 215                 220 ccg cac aag cac aag cac cgc aag gat gag aat aag ctg aag acg agg      721
Pro His Lys His Lys His Arg Lys Asp Glu Asn Lys Leu Lys Thr Arg
225                 230                 235                 240 ctg tgt ctg gga atc acc gac ctg ctc gag gac atc ggc gcg gag gac      769
Leu Cys Leu Gly Ile Thr Asp Leu Leu Glu Asp Ile Gly Ala Glu Asp
                245                 250                 255 gac gac agc gtg ctc gtc acc atc gtg ccg aag gca ggc aaa gga aag      817
Asp Asp Ser Val Leu Val Thr Ile Val Pro Lys Ala Gly Lys Gly Lys
            260                 265                 270 gtg tcc gtc ggc ggt ctt cgg att gac ttt tcc aag tgaggaaata           863
Val Ser Val Gly Gly Leu Arg Ile Asp Phe Ser Lys
        275                 280 aaagaattca cgtgccgtgc tgctttcaa tgtacgaata aaataagagt gcatcatcac     923
cgaccatggt tctactttaa aaaaaaaaaa aaaaaaa                             960

<210> SEQ ID NO 8
<211> LENGTH: 284
<212> TYPE: PRT
<213> ORGANISM: banana

<400> SEQUENCE: 8

Leu Leu Phe Leu Gly Ser Ala Tyr Arg Ala Gly Asp Gln Pro Asn Pro
1               5                   10                  15

Gly Ala Gly Ser Ile Glu Asn Met Pro His Asn Val His Leu Trp
            20                  25                  30

Thr Gly Asp Arg Thr Gln Pro Asn Phe Glu Asn Met Gly Thr Phe Tyr
        35                  40                  45

Ala Ala Ala Arg Asp Pro Ile Phe Phe Ala His His Ala Asn Ile Asp
    50                  55                  60

Arg Met Trp Tyr Leu Trp Lys Lys Leu Ser Arg Lys His Gln Asp Phe
65                  70                  75                  80

Asn Asp Ser Asp Trp Leu Lys Ala Ser Phe Leu Phe Tyr Asp Glu Asn
                85                  90                  95

Ala Asp Leu Val Arg Val Thr Val Lys Asp Cys Leu Glu Thr Glu Trp
            100                 105                 110

Leu Arg Tyr Thr Tyr Gln Asp Val Lys Ile Pro Trp Ala Asn Thr Arg
```

```
                115                 120                 125
Pro Thr Pro Lys Leu Ala Lys Ala Arg Lys Ala Gly Ser Arg Ser Leu
        130                 135                 140

Lys Ala Thr Ala Glu Val Gln Phe Pro Val Thr Leu Glu Ser Pro Val
145                 150                 155                 160

Lys Val Thr Val Lys Arg Pro Lys Val Gly Arg Ser Gly Lys Glu Lys
                165                 170                 175

Glu Asp Glu Glu Ile Leu Ile Val Glu Gly Ile Glu Phe Asp Arg
            180                 185                 190

Asp Tyr Phe Ile Lys Phe Asp Val Phe Val Asn Ala Thr Glu Gly Asp
            195                 200                 205

Gly Ile Thr Ala Gly Ala Ser Glu Phe Ala Gly Ser Phe Val Asn Val
        210                 215                 220

Pro His Lys His Lys His Arg Lys Asp Glu Asn Lys Leu Lys Thr Arg
225                 230                 235                 240

Leu Cys Leu Gly Ile Thr Asp Leu Leu Glu Asp Ile Gly Ala Glu Asp
                245                 250                 255

Asp Asp Ser Val Leu Val Thr Ile Val Pro Lys Ala Gly Lys Gly Lys
            260                 265                 270

Val Ser Val Gly Gly Leu Arg Ile Asp Phe Ser Lys
        275                 280

<210> SEQ ID NO 9
<211> LENGTH: 545
<212> TYPE: DNA
<213> ORGANISM: tobacco
<220> FEATURE:
<221> NAME/KEY: CDS
<222> LOCATION: (1)..(543)

<400> SEQUENCE: 9 gat ccg acg ttt gcg ttg cca tat tgg aac tgg gat cat cca aag ggc      48
Asp Pro Thr Phe Ala Leu Pro Tyr Trp Asn Trp Asp His Pro Lys Gly
1               5                   10                  15 atg cgt ttg cca cac atg ttt gat caa cca aac gtg tac cct gat ctt      96
Met Arg Leu Pro His Met Phe Asp Gln Pro Asn Val Tyr Pro Asp Leu
            20                  25                  30 tac gat cca aga cgt aac caa gaa cac cgc ggt tct gta atc atg gac     144
Tyr Asp Pro Arg Arg Asn Gln Glu His Arg Gly Ser Val Ile Met Asp
        35                  40                  45 ctt ggt cat ttt ggt caa gac gtg aaa gga act gac ttg caa atg atg     192
Leu Gly His Phe Gly Gln Asp Val Lys Gly Thr Asp Leu Gln Met Met
    50                  55                  60 agc aat aac ctt act cta atg tat cgt caa atg att acc aat tca cca     240
Ser Asn Asn Leu Thr Leu Met Tyr Arg Gln Met Ile Thr Asn Ser Pro
65                  70                  75                  80 tgt cca caa ctc ttt ttc ggt aag cca tat tgt acg gaa gtt gga ccc     288
Cys Pro Gln Leu Phe Phe Gly Lys Pro Tyr Cys Thr Glu Val Gly Pro
                85                  90                  95 aaa cca ggg cag gga gct att gaa aac atc cct cat act cct gtc cac     336
Lys Pro Gly Gln Gly Ala Ile Glu Asn Ile Pro His Thr Pro Val His
            100                 105                 110 att tgg gtt ggt agt aag cct aat gag aat aac tgt aaa aac ggt gaa     384
Ile Trp Val Gly Ser Lys Pro Asn Glu Asn Asn Cys Lys Asn Gly Glu
        115                 120                 125 gat atg gga aat ttc tat tca gct ggt aag gat cct gct ttc tat agt     432
Asp Met Gly Asn Phe Tyr Ser Ala Gly Lys Asp Pro Ala Phe Tyr Ser
    130                 135                 140
```

```
cac cat gca aat gta gat cgc atg tgg aca ata tgg aaa aca tta gga         480
His His Ala Asn Val Asp Arg Met Trp Thr Ile Trp Lys Thr Leu Gly
145                 150                 155                 160 gga aaa cgc aag gac atc aac aag cca gat tat ttg aac act gag ttc         528
Gly Lys Arg Lys Asp Ile Asn Lys Pro Asp Tyr Leu Asn Thr Glu Phe
                165                 170                 175 ttt ttc tac gac gaa aa                                                  545
Phe Phe Tyr Asp Glu
            180

<210> SEQ ID NO 10
<211> LENGTH: 181
<212> TYPE: PRT
<213> ORGANISM: tobacco

<400> SEQUENCE: 10

Asp Pro Thr Phe Ala Leu Pro Tyr Trp Asn Trp Asp His Pro Lys Gly
 1               5                  10                  15

Met Arg Leu Pro His Met Phe Asp Gln Pro Asn Val Tyr Pro Asp Leu
            20                  25                  30

Tyr Asp Pro Arg Arg Asn Gln Glu His Arg Gly Ser Val Ile Met Asp
        35                  40                  45

Leu Gly His Phe Gly Gln Asp Val Lys Gly Thr Asp Leu Gln Met Met
    50                  55                  60

Ser Asn Asn Leu Thr Leu Met Tyr Arg Gln Met Ile Thr Asn Ser Pro
65                  70                  75                  80

Cys Pro Gln Leu Phe Phe Gly Lys Pro Tyr Cys Thr Glu Val Gly Pro
                85                  90                  95

Lys Pro Gly Gln Gly Ala Ile Glu Asn Ile Pro His Thr Pro Val His
            100                 105                 110

Ile Trp Val Gly Ser Lys Pro Asn Glu Asn Asn Cys Lys Asn Gly Glu
        115                 120                 125

Asp Met Gly Asn Phe Tyr Ser Ala Gly Lys Asp Pro Ala Phe Tyr Ser
    130                 135                 140

His His Ala Asn Val Asp Arg Met Trp Thr Ile Trp Lys Thr Leu Gly
145                 150                 155                 160

Gly Lys Arg Lys Asp Ile Asn Lys Pro Asp Tyr Leu Asn Thr Glu Phe
                165                 170                 175

Phe Phe Tyr Asp Glu
            180

<210> SEQ ID NO 11
<211> LENGTH: 673
<212> TYPE: DNA
<213> ORGANISM: tobacco
<220> FEATURE:
<221> NAME/KEY: CDS
<222> LOCATION: (3)..(671)

<400> SEQUENCE: 11 tg cac tgt gcg tat tgc aac ggt gct tac aaa att ggt ggc aaa gag          47
   His Cys Ala Tyr Cys Asn Gly Ala Tyr Lys Ile Gly Gly Lys Glu
    1               5                  10                  15 tta caa gtc cat ttc tcg tgg ctt ttt ttc cct ttt cat aga tgg tac         95
Leu Gln Val His Phe Ser Trp Leu Phe Phe Pro Phe His Arg Trp Tyr
            20                  25                  30 ttg tac ttc tat gaa aga atc ttg ggc tct tta att aat gat cct act        143
Leu Tyr Phe Tyr Glu Arg Ile Leu Gly Ser Leu Ile Asn Asp Pro Thr
        35                  40                  45
```

```
ttt ggt ttg cca tat tgg aac tgg gac cat cca aag ggc atg cgt ata      191
Phe Gly Leu Pro Tyr Trp Asn Trp Asp His Pro Lys Gly Met Arg Ile
         50                  55                  60 cct ccc atg ttc gat cgt gaa ggg tct tcc ctt tac gac gaa aaa cgt      239
Pro Pro Met Phe Asp Arg Glu Gly Ser Ser Leu Tyr Asp Glu Lys Arg
 65                  70                  75 aac caa agt cac cgt aat gga acc ata att gat ctt ggt cat ttc ggt      287
Asn Gln Ser His Arg Asn Gly Thr Ile Ile Asp Leu Gly His Phe Gly
 80                  85                  90                  95 caa gaa gtc caa aca act caa ctg cag cag atg act aat aac tta act      335
Gln Glu Val Gln Thr Thr Gln Leu Gln Gln Met Thr Asn Asn Leu Thr
                100                 105                 110 ata atg tat cgt caa atg ata act aat gct cct tgc ccc ttg ctc ttc      383
Ile Met Tyr Arg Gln Met Ile Thr Asn Ala Pro Cys Pro Leu Leu Phe
                115                 120                 125 ttt ggt cag cct tac cct cta gga act gat ccc agt cca ggg atg ggc      431
Phe Gly Gln Pro Tyr Pro Leu Gly Thr Asp Pro Ser Pro Gly Met Gly
            130                 135                 140 act att gaa aac atc cct cat act cct gtc cac att tgg gtt ggt agt      479
Thr Ile Glu Asn Ile Pro His Thr Pro Val His Ile Trp Val Gly Ser
145                 150                 155 agg ctt gat gag aat aat acg aaa cac ggt gag gat atg ggt aat ttt      527
Arg Leu Asp Glu Asn Asn Thr Lys His Gly Glu Asp Met Gly Asn Phe
160                 165                 170                 175 tac tcg gcc ggt tta gac ccg ctt ttc tat tcc cat cac gcc aat gtg      575
Tyr Ser Ala Gly Leu Asp Pro Leu Phe Tyr Ser His His Ala Asn Val
                180                 185                 190 gac cgg atg tgg tcc gag tgg aaa gcc tta gga ggg aaa aga agg gat      623
Asp Arg Met Trp Ser Glu Trp Lys Ala Leu Gly Gly Lys Arg Arg Asp
            195                 200                 205 ctc acg cac aaa gat tgg ttg aac tcc gag ttc ttt ttc tac gat gaa      671
Leu Thr His Lys Asp Trp Leu Asn Ser Glu Phe Phe Phe Tyr Asp Glu
        210                 215                 220 aa                                                                    673

<210> SEQ ID NO 12
<211> LENGTH: 223
<212> TYPE: PRT
<213> ORGANISM: tobacco

<400> SEQUENCE: 12

His Cys Ala Tyr Cys Asn Gly Ala Tyr Lys Ile Gly Gly Lys Glu Leu
 1               5                  10                  15

Gln Val His Phe Ser Trp Leu Phe Phe Pro Phe His Arg Trp Tyr Leu
                20                  25                  30

Tyr Phe Tyr Glu Arg Ile Leu Gly Ser Leu Ile Asn Asp Pro Thr Phe
            35                  40                  45

Gly Leu Pro Tyr Trp Asn Trp Asp His Pro Lys Gly Met Arg Ile Pro
 50                  55                  60

Pro Met Phe Asp Arg Glu Gly Ser Ser Leu Tyr Asp Glu Lys Arg Asn
 65                  70                  75                  80

Gln Ser His Arg Asn Gly Thr Ile Ile Asp Leu Gly His Phe Gly Gln
                 85                  90                  95

Glu Val Gln Thr Thr Gln Leu Gln Gln Met Thr Asn Asn Leu Thr Ile
            100                 105                 110

Met Tyr Arg Gln Met Ile Thr Asn Ala Pro Cys Pro Leu Leu Phe Phe
        115                 120                 125

Gly Gln Pro Tyr Pro Leu Gly Thr Asp Pro Ser Pro Gly Met Gly Thr
```

```
                130                 135                 140
Ile Glu Asn Ile Pro His Thr Pro Val His Ile Trp Val Gly Ser Arg
145                 150                 155                 160

Leu Asp Glu Asn Asn Thr Lys His Gly Glu Asp Met Gly Asn Phe Tyr
                165                 170                 175

Ser Ala Gly Leu Asp Pro Leu Phe Tyr Ser His His Ala Asn Val Asp
            180                 185                 190

Arg Met Trp Ser Glu Trp Lys Ala Leu Gly Gly Lys Arg Arg Asp Leu
        195                 200                 205

Thr His Lys Asp Trp Leu Asn Ser Glu Phe Phe Tyr Asp Glu
    210                 215                 220

<210> SEQ ID NO 13
<211> LENGTH: 685
<212> TYPE: DNA
<213> ORGANISM: tobacco
<220> FEATURE:
<221> NAME/KEY: CDS
<222> LOCATION: (3)..(683)

<400> SEQUENCE: 13 tg cat tgt gcg tat tgc aac gat gct tac aca atg ggt gac caa aag        47
   His Cys Ala Tyr Cys Asn Asp Ala Tyr Thr Met Gly Asp Gln Lys
    1               5                  10                  15 tta caa gtt cac caa tcg tgg ctt ttc ttc ccg ttt cat aga tgg tac       95
Leu Gln Val His Gln Ser Trp Leu Phe Phe Pro Phe His Arg Trp Tyr
                20                  25                  30 ttg tac ttc tac gag aga atc ttg ggc tcc ctc atc gat gat cca act      143
Leu Tyr Phe Tyr Glu Arg Ile Leu Gly Ser Leu Ile Asp Asp Pro Thr
            35                  40                  45 ttt gct ctg cca tat tgg aac tgg gac cat cca agc ggc atg cgt ttg      191
Phe Ala Leu Pro Tyr Trp Asn Trp Asp His Pro Ser Gly Met Arg Leu
        50                  55                  60 cct gct atg ttc gat gtc gaa ggt tct tcc ctc tac gat gca aga cgt      239
Pro Ala Met Phe Asp Val Glu Gly Ser Ser Leu Tyr Asp Ala Arg Arg
    65                  70                  75 aat cca cat gtc cgt aat gga acc ata atc gat ctt ggt ttt ttc ggt      287
Asn Pro His Val Arg Asn Gly Thr Ile Ile Asp Leu Gly Phe Phe Gly
80                  85                  90                  95 gat gaa gtc aaa act aat gaa ata cag atg ata act aac aac tta att      335
Asp Glu Val Lys Thr Asn Glu Ile Gln Met Ile Thr Asn Asn Leu Ile
                100                 105                 110 cta atg tat cgt caa atg ata act aat gct cca tgc ccg ctg ttg ttc      383
Leu Met Tyr Arg Gln Met Ile Thr Asn Ala Pro Cys Pro Leu Leu Phe
            115                 120                 125 ttc gga gag cct tac aga ttc gga tct aaa ccc aat ccg ggg cag gga      431
Phe Gly Glu Pro Tyr Arg Phe Gly Ser Lys Pro Asn Pro Gly Gln Gly
        130                 135                 140 acc att gaa aac att cct cat act ccg gtt cac att tgg act ggt act      479
Thr Ile Glu Asn Ile Pro His Thr Pro Val His Ile Trp Thr Gly Thr
    145                 150                 155 gtg cgg tgt acg gat ttg ggt aat tgt gtg cca tca tac ggt gag gat      527
Val Arg Cys Thr Asp Leu Gly Asn Cys Val Pro Ser Tyr Gly Glu Asp
160                 165                 170                 175 atg ggt aat ttc tac tca gct ggt tta gac cca gtt ttt tac agc cac      575
Met Gly Asn Phe Tyr Ser Ala Gly Leu Asp Pro Val Phe Tyr Ser His
                180                 185                 190 cac gcc aat gtg gac cgc atg tgg aat gaa tgg aaa gca cta gga ggg      623
His Ala Asn Val Asp Arg Met Trp Asn Glu Trp Lys Ala Leu Gly Gly
            195                 200                 205
```

```
aaa aga agg gat ctc aca gac aat gat tgg tta aac tcg gag ttc ttt      671
Lys Arg Arg Asp Leu Thr Asp Asn Asp Trp Leu Asn Ser Glu Phe Phe
        210                 215                 220 ttc tac gac gaa aa                                                    685
Phe Tyr Asp Glu
    225

<210> SEQ ID NO 14
<211> LENGTH: 227
<212> TYPE: PRT
<213> ORGANISM: tobacco

<400> SEQUENCE: 14

His Cys Ala Tyr Cys Asn Asp Ala Tyr Thr Met Gly Asp Gln Lys Leu
  1               5                  10                  15

Gln Val His Gln Ser Trp Leu Phe Phe Pro Phe His Arg Trp Tyr Leu
             20                  25                  30

Tyr Phe Tyr Glu Arg Ile Leu Gly Ser Leu Ile Asp Asp Pro Thr Phe
         35                  40                  45

Ala Leu Pro Tyr Trp Asn Trp Asp His Pro Ser Gly Met Arg Leu Pro
     50                  55                  60

Ala Met Phe Asp Val Glu Gly Ser Ser Leu Tyr Asp Ala Arg Arg Asn
 65                  70                  75                  80

Pro His Val Arg Asn Gly Thr Ile Ile Asp Leu Gly Phe Phe Gly Asp
                 85                  90                  95

Glu Val Lys Thr Asn Glu Ile Gln Met Ile Thr Asn Asn Leu Ile Leu
            100                 105                 110

Met Tyr Arg Gln Met Ile Thr Asn Ala Pro Cys Pro Leu Leu Phe Phe
        115                 120                 125

Gly Glu Pro Tyr Arg Phe Gly Ser Lys Pro Asn Pro Gly Gln Gly Thr
    130                 135                 140

Ile Glu Asn Ile Pro His Thr Pro Val His Ile Trp Thr Gly Thr Val
145                 150                 155                 160

Arg Cys Thr Asp Leu Gly Asn Cys Val Pro Ser Tyr Gly Glu Asp Met
                165                 170                 175

Gly Asn Phe Tyr Ser Ala Gly Leu Asp Pro Val Phe Tyr Ser His His
            180                 185                 190

Ala Asn Val Asp Arg Met Trp Asn Glu Trp Lys Ala Leu Gly Gly Lys
        195                 200                 205

Arg Arg Asp Leu Thr Asp Asn Asp Trp Leu Asn Ser Glu Phe Phe Phe
    210                 215                 220

Tyr Asp Glu
225

<210> SEQ ID NO 15
<211> LENGTH: 670
<212> TYPE: DNA
<213> ORGANISM: pineapple
<220> FEATURE:
<221> NAME/KEY: CDS
<222> LOCATION: (3)..(668)

<400> SEQUENCE: 15 tg cat tgt gcg tac tgc gac ggc gcg tat gac caa atc ggc ttc ccc       47
   His Cys Ala Tyr Cys Asp Gly Ala Tyr Asp Gln Ile Gly Phe Pro
     1               5                  10                  15 gat ctc gag atc cag atc cac aac tcg tgg ctc ttc ttt cct tgg cac      95
Asp Leu Glu Ile Gln Ile His Asn Ser Trp Leu Phe Phe Pro Trp His
```

```
                    20                  25                  30
cgg ttc tac ctc tac ttc aac gag cgc ata ctc ggg aaa ctt atc ggc    143
Arg Phe Tyr Leu Tyr Phe Asn Glu Arg Ile Leu Gly Lys Leu Ile Gly
             35                  40                  45 gac gac acg ttc gcg ctg cct ttc tgg aac tgg gac gcg ccg ggg ggc    191
Asp Asp Thr Phe Ala Leu Pro Phe Trp Asn Trp Asp Ala Pro Gly Gly
     50                  55                  60 atg cag ttc ccg tct atc tac acg gac cct tca tcc tcg cta tat gac    239
Met Gln Phe Pro Ser Ile Tyr Thr Asp Pro Ser Ser Ser Leu Tyr Asp
 65                  70                  75 aag ctg cgt gat gcg aag cac cag ccg ccg act ttg att gac ctc gac    287
Lys Leu Arg Asp Ala Lys His Gln Pro Pro Thr Leu Ile Asp Leu Asp
 80                  85                  90                  95 tac aat ggc acc gat cct acc ttc tcc cct gaa gaa cag att aac cac    335
Tyr Asn Gly Thr Asp Pro Thr Phe Ser Pro Glu Glu Gln Ile Asn His
            100                 105                 110 aac ctc gcc gtc atg tac cga cag gtg ata tcc agt gga aag aca cca    383
Asn Leu Ala Val Met Tyr Arg Gln Val Ile Ser Ser Gly Lys Thr Pro
        115                 120                 125 gag ctg ttt atg ggc tca gcg tac cgc gcc ggt gac cag cct gac ccc    431
Glu Leu Phe Met Gly Ser Ala Tyr Arg Ala Gly Asp Gln Pro Asp Pro
    130                 135                 140 ggc gca ggt tct gta gag cag aag ccg cac ggc ccg gtg cat gtg tgg    479
Gly Ala Gly Ser Val Glu Gln Lys Pro His Gly Pro Val His Val Trp
145                 150                 155 aca ggt gat cgc aac cag ccc aat cgc gaa gac atg ggc acg ctc tac    527
Thr Gly Asp Arg Asn Gln Pro Asn Arg Glu Asp Met Gly Thr Leu Tyr
160                 165                 170                 175 tcg gcg gcg tgg gac ccc gtt ttt ttc gca cac cac ggc aac atc gac    575
Ser Ala Ala Trp Asp Pro Val Phe Phe Ala His His Gly Asn Ile Asp
            180                 185                 190 cgc atg tgg tac gtg tgg agg aac ctt ggc ggc aag cac cgc aac ttc    623
Arg Met Trp Tyr Val Trp Arg Asn Leu Gly Gly Lys His Arg Asn Phe
        195                 200                 205 acc gac ccc gac tgg ctc aac gcg tcc ttc ctg ttc tac gac gaa aa    670
Thr Asp Pro Asp Trp Leu Asn Ala Ser Phe Leu Phe Tyr Asp Glu
    210                 215                 220

<210> SEQ ID NO 16
<211> LENGTH: 222
<212> TYPE: PRT
<213> ORGANISM: pineapple

<400> SEQUENCE: 16

His Cys Ala Tyr Cys Asp Gly Ala Tyr Asp Gln Ile Gly Phe Pro Asp
 1               5                  10                  15

Leu Glu Ile Gln Ile His Asn Ser Trp Leu Phe Pro Trp His Arg
             20                  25                  30

Phe Tyr Leu Tyr Phe Asn Glu Arg Ile Leu Gly Lys Leu Ile Gly Asp
         35                  40                  45

Asp Thr Phe Ala Leu Pro Phe Trp Asn Trp Asp Ala Pro Gly Gly Met
     50                  55                  60

Gln Phe Pro Ser Ile Tyr Thr Asp Pro Ser Ser Ser Leu Tyr Asp Lys
 65                  70                  75                  80

Leu Arg Asp Ala Lys His Gln Pro Pro Thr Leu Ile Asp Leu Asp Tyr
                 85                  90                  95

Asn Gly Thr Asp Pro Thr Phe Ser Pro Glu Glu Gln Ile Asn His Asn
            100                 105                 110
```

```
Leu Ala Val Met Tyr Arg Gln Val Ile Ser Ser Gly Lys Thr Pro Glu
        115                 120                 125

Leu Phe Met Gly Ser Ala Tyr Arg Ala Gly Asp Gln Pro Asp Pro Gly
    130                 135                 140

Ala Gly Ser Val Glu Gln Lys Pro His Gly Pro Val His Val Trp Thr
145                 150                 155                 160

Gly Asp Arg Asn Gln Pro Asn Arg Glu Asp Met Gly Thr Leu Tyr Ser
                165                 170                 175

Ala Ala Trp Asp Pro Val Phe Phe Ala His His Gly Asn Ile Asp Arg
            180                 185                 190

Met Trp Tyr Val Trp Arg Asn Leu Gly Gly Lys His Arg Asn Phe Thr
        195                 200                 205

Asp Pro Asp Trp Leu Asn Ala Ser Phe Leu Phe Tyr Asp Glu
    210                 215                 220

<210> SEQ ID NO 17
<211> LENGTH: 1319
<212> TYPE: DNA
<213> ORGANISM: pineapple
<220> FEATURE:
<221> NAME/KEY: CDS
<222> LOCATION: (1)..(1053)

<400> SEQUENCE: 17 ttg ccg ttt tgg aat tgg gac gcg ccg ggg ggc atg cag atc ccg gcc    48
Leu Pro Phe Trp Asn Trp Asp Ala Pro Gly Gly Met Gln Ile Pro Ala
 1               5                  10                  15 atc tac gcc gac gct tcg tcc ccg ctc tac gac aag ctg cgc aat gcg    96
Ile Tyr Ala Asp Ala Ser Ser Pro Leu Tyr Asp Lys Leu Arg Asn Ala
             20                  25                  30 aag cac cag ccg ccg act ttg gtc gac ctc gac tac aac ggc acc gac   144
Lys His Gln Pro Pro Thr Leu Val Asp Leu Asp Tyr Asn Gly Thr Asp
         35                  40                  45 ccg acc ttc acc cct gag cag cag atc gcc cac aac ctc acc atc atg   192
Pro Thr Phe Thr Pro Glu Gln Gln Ile Ala His Asn Leu Thr Ile Met
     50                  55                  60 tac cga cag gtg ata tcc ggc ggg aag acg ccg gag ttg ttt atg ggc   240
Tyr Arg Gln Val Ile Ser Gly Gly Lys Thr Pro Glu Leu Phe Met Gly
 65                  70                  75                  80 gcg gcg tac cgc gcg ggc gac gcg cca gac ccg ggc gca ggc act cta   288
Ala Ala Tyr Arg Ala Gly Asp Ala Pro Asp Pro Gly Ala Gly Thr Leu
                 85                  90                  95 gag ctc gtg ccg cac aac acg atg cat ttg tgg acc ggc gac ccc aac   336
Glu Leu Val Pro His Asn Thr Met His Leu Trp Thr Gly Asp Pro Asn
            100                 105                 110 caa ccc aac gac gaa gac atg ggc acg ttc tac gcg gcg gcg cgg gac   384
Gln Pro Asn Asp Glu Asp Met Gly Thr Phe Tyr Ala Ala Ala Arg Asp
        115                 120                 125 ccc atc ttc ttc gcc cac cac ggc aac gtc gac cgc atg tgg tac gtg   432
Pro Ile Phe Phe Ala His His Gly Asn Val Asp Arg Met Trp Tyr Val
    130                 135                 140 tgg cgg aaa ctc ggg ggc acg cac cgc gat ttc acc gac ccc gac tgg   480
Trp Arg Lys Leu Gly Gly Thr His Arg Asp Phe Thr Asp Pro Asp Trp
145                 150                 155                 160 ctc aac gcg tcc ttc ctc ttc tac gac gag aac gcg cag ctc gtc cgc   528
Leu Asn Ala Ser Phe Leu Phe Tyr Asp Glu Asn Ala Gln Leu Val Arg
                165                 170                 175 gtc aaa gta aag gac tgc ttg agc gcc gac gcg ctg cgg tac acg tac   576
Val Lys Val Lys Asp Cys Leu Ser Ala Asp Ala Leu Arg Tyr Thr Tyr
            180                 185                 190
```

```
cag gac gtc gac atc ccg tgg atc agt gcg aag ccg acg ccg aag aaa    624
Gln Asp Val Asp Ile Pro Trp Ile Ser Ala Lys Pro Thr Pro Lys Lys
            195                 200                 205 aca ccg ggg ggc gct gcg cct tcc acg aca gag gct ata ttt ccg gtg    672
Thr Pro Gly Gly Ala Ala Pro Ser Thr Thr Glu Ala Ile Phe Pro Val
        210                 215                 220 gtg ctg gat aag ccg gtg agc tct acg gtg gcg agg ccg aag acg ggg    720
Val Leu Asp Lys Pro Val Ser Ser Thr Val Ala Arg Pro Lys Thr Gly
225                 230                 235                 240 agg agt act ggg gag gag gag gtg ttg gtg gtg gag gga atc gag ctg    768
Arg Ser Thr Gly Glu Glu Glu Val Leu Val Val Glu Gly Ile Glu Leu
                245                 250                 255 gac aag gac gtg gcc gtg aag ttc gac gtg tat ata aac gcg ccg gac    816
Asp Lys Asp Val Ala Val Lys Phe Asp Val Tyr Ile Asn Ala Pro Asp
            260                 265                 270 aac gaa ggg gtg ggg ccg gag gcg agc gag ttc gca ggg agc ttc gtc    864
Asn Glu Gly Val Gly Pro Glu Ala Ser Glu Phe Ala Gly Ser Phe Val
        275                 280                 285 cag gtg ccg cac aag cac aag aag ggg aag aag gag aag gcg agg att    912
Gln Val Pro His Lys His Lys Lys Gly Lys Lys Glu Lys Ala Arg Ile
    290                 295                 300 aaa acg acg ctc agg ctc ggg ata acg gac ctg ctc gag gac atc ggc    960
Lys Thr Thr Leu Arg Leu Gly Ile Thr Asp Leu Leu Glu Asp Ile Gly
305                 310                 315                 320 gcc gag gac gac gag agc gtg ctc gtc acg ctc gtg ccg agg ata ggc   1008
Ala Glu Asp Asp Glu Ser Val Leu Val Thr Leu Val Pro Arg Ile Gly
                325                 330                 335 gag ggg ttg gtc aag gtt ggt ggg cta agg atc gat ttc tcc aag        1053
Glu Gly Leu Val Lys Val Gly Gly Leu Arg Ile Asp Phe Ser Lys
            340                 345                 350 tgatcagcag caaattaact atacatgaaa gtaaaaaaaa ttgcatttac ctacctatag  1113
aagagaataa atgcgtatgt aatctgcccc atttgtcact tttaatttct cgagcgtgtt  1173
ctgaatgaga gttgcatgca tgcgcgcagc cataatgcct ggtatagtgt agtagtttag  1233
gcgtggatac gtataacgta cgtatgcatg tataaggaat aatgatgagt ttactatgca  1293
aaaaaaaaaa aaaaaaaaaa aaaaaa                                       1319

<210> SEQ ID NO 18
<211> LENGTH: 351
<212> TYPE: PRT
<213> ORGANISM: pineapple

<400> SEQUENCE: 18

Leu Pro Phe Trp Asn Trp Asp Ala Pro Gly Gly Met Gln Ile Pro Ala
 1               5                  10                  15

Ile Tyr Ala Asp Ala Ser Ser Pro Leu Tyr Asp Lys Leu Arg Asn Ala
            20                  25                  30

Lys His Gln Pro Pro Thr Leu Val Asp Leu Asp Tyr Asn Gly Thr Asp
        35                  40                  45

Pro Thr Phe Thr Pro Glu Gln Gln Ile Ala His Asn Leu Thr Ile Met
    50                  55                  60

Tyr Arg Gln Val Ile Ser Gly Lys Thr Pro Glu Leu Phe Met Gly
 65                  70                  75                  80

Ala Ala Tyr Arg Ala Gly Asp Ala Pro Asp Pro Gly Ala Gly Thr Leu
                85                  90                  95

Glu Leu Val Pro His Asn Thr Met His Leu Trp Thr Gly Asp Pro Asn
            100                 105                 110
```

```
Gln Pro Asn Asp Glu Asp Met Gly Thr Phe Tyr Ala Ala Ala Arg Asp
            115                 120                 125

Pro Ile Phe Phe Ala His His Gly Asn Val Asp Arg Met Trp Tyr Val
130                 135                 140

Trp Arg Lys Leu Gly Gly Thr His Arg Asp Phe Thr Asp Pro Asp Trp
145                 150                 155                 160

Leu Asn Ala Ser Phe Leu Phe Tyr Asp Glu Asn Ala Gln Leu Val Arg
                165                 170                 175

Val Lys Val Lys Asp Cys Leu Ser Ala Asp Ala Leu Arg Tyr Thr Tyr
            180                 185                 190

Gln Asp Val Asp Ile Pro Trp Ile Ser Ala Lys Pro Thr Pro Lys Lys
        195                 200                 205

Thr Pro Gly Gly Ala Ala Pro Ser Thr Thr Glu Ala Ile Phe Pro Val
    210                 215                 220

Val Leu Asp Lys Pro Val Ser Ser Thr Val Ala Arg Pro Lys Thr Gly
225                 230                 235                 240

Arg Ser Thr Gly Glu Glu Val Leu Val Glu Gly Ile Glu Leu
                245                 250                 255

Asp Lys Asp Val Ala Val Lys Phe Asp Val Tyr Ile Asn Ala Pro Asp
            260                 265                 270

Asn Glu Gly Val Gly Pro Glu Ala Ser Glu Phe Ala Gly Ser Phe Val
        275                 280                 285

Gln Val Pro His Lys His Lys Lys Gly Lys Lys Glu Lys Ala Arg Ile
    290                 295                 300

Lys Thr Thr Leu Arg Leu Gly Ile Thr Asp Leu Leu Glu Asp Ile Gly
305                 310                 315                 320

Ala Glu Asp Asp Glu Ser Val Leu Val Thr Leu Val Pro Arg Ile Gly
                325                 330                 335

Glu Gly Leu Val Lys Val Gly Gly Leu Arg Ile Asp Phe Ser Lys
            340                 345                 350

<210> SEQ ID NO 19
<211> LENGTH: 2181
<212> TYPE: DNA
<213> ORGANISM: pineapple
<220> FEATURE:
<221> NAME/KEY: CDS
<222> LOCATION: (2)..(1858)

<400> SEQUENCE: 19 c ggt atc gat aag ctt gat cca gtg cct ggt tta ggt gta ttc act atg         49
  Gly Ile Asp Lys Leu Asp Pro Val Pro Gly Leu Gly Val Phe Thr Met
    1               5                   10                  15 gcc acc ctc tct aaa cta gct tcc caa cca ata aca cct cca ctc tcc         97
Ala Thr Leu Ser Lys Leu Ala Ser Gln Pro Ile Thr Pro Pro Leu Ser
                20                  25                  30 ccg ctc cct cct ttg cat gct cct tct ctc acc aaa agc ttc acc acc        145
Pro Leu Pro Pro Leu His Ala Pro Ser Leu Thr Lys Ser Phe Thr Thr
            35                  40                  45 acc ttc ctc tcc cct gta ggg gtc cca aac cac ccc gtc ata aga tct        193
Thr Phe Leu Ser Pro Val Gly Val Pro Asn His Pro Val Ile Arg Ser
    50                  55                  60 cat gca aat cta agg agc aac aag aga atg ccg aca agc ctg cgg gcc        241
His Ala Asn Leu Arg Ser Asn Lys Arg Met Pro Thr Ser Leu Arg Ala
65                  70                  75                  80 gca tcg ccc gcc gcg acc tac tcc tgg gcc ctc ggc ggg ctt tac ggt        289
Ala Ser Pro Ala Ala Thr Tyr Ser Trp Ala Leu Gly Gly Leu Tyr Gly
```

```
                    85                  90                  95
gcc acc act ggg ctc ggc ctc aac cgt cga gcg gcc gcc cct atc     337
Ala Thr Thr Gly Leu Gly Leu Asn Arg Arg Ala Ala Ala Pro Ile
            100                 105                 110 ctg gct ccc gac ctc tca act tgt ggg ccg cct gcc gac ctc cct gcc 385
Leu Ala Pro Asp Leu Ser Thr Cys Gly Pro Pro Ala Asp Leu Pro Ala
        115                 120                 125 tcc gcc cga ccg aca gtt tgc tgc cca tac caa tcc acc atc atc     433
Ser Ala Arg Pro Thr Val Cys Cys Pro Pro Tyr Gln Ser Thr Ile Ile
130                 135                 140 gac ttc aag ctc ccc ccg cga tct gct ccg ctt cgc gtc cgg cct gcg 481
Asp Phe Lys Leu Pro Pro Arg Ser Ala Pro Leu Arg Val Arg Pro Ala
145                 150                 155                 160 gcc cac ttg gtt gac gcc gac tac ctg gcc aag tat aag aag gcg gtc 529
Ala His Leu Val Asp Ala Asp Tyr Leu Ala Lys Tyr Lys Lys Ala Val
                165                 170                 175 gag ctc atg agg gcc ctg ccg gcc gac gac ccg cgc aac ttc gta cag 577
Glu Leu Met Arg Ala Leu Pro Ala Asp Asp Pro Arg Asn Phe Val Gln
            180                 185                 190 caa gcg aaa gtg cac tgt gcg tat tgc gac ggc gcg tat gac caa atc 625
Gln Ala Lys Val His Cys Ala Tyr Cys Asp Gly Ala Tyr Asp Gln Ile
        195                 200                 205 ggc ttc ccc gat ctc gag atc cag atc cac aac tcg tgg ctc ttc ttt 673
Gly Phe Pro Asp Leu Glu Ile Gln Ile His Asn Ser Trp Leu Phe Phe
    210                 215                 220 cct tgg cac cgg ttc tac ctc tac tcc aac gag cgc ata ctc ggg aaa 721
Pro Trp His Arg Phe Tyr Leu Tyr Ser Asn Glu Arg Ile Leu Gly Lys
225                 230                 235                 240 ctt atc ggc gac gac acg ttc gcg ctg cct ttc tgg aac tgg gac gcg 769
Leu Ile Gly Asp Asp Thr Phe Ala Leu Pro Phe Trp Asn Trp Asp Ala
                245                 250                 255 ccg ggg ggc atg cag ttc ccg tct atc tac aca gac cct tca tcc tcg 817
Pro Gly Gly Met Gln Phe Pro Ser Ile Tyr Thr Asp Pro Ser Ser Ser
            260                 265                 270 cta tat gac aag ctg cgt gat gcg aag cac cag ccg ccg act ttg att 865
Leu Tyr Asp Lys Leu Arg Asp Ala Lys His Gln Pro Pro Thr Leu Ile
        275                 280                 285 gac ctc gac tac aat ggc acc gat cct acc ttc tcc cct gaa gaa cag 913
Asp Leu Asp Tyr Asn Gly Thr Asp Pro Thr Phe Ser Pro Glu Glu Gln
    290                 295                 300 att aac cac aac ctc gcc gtc atg tac cga cag gtg ata tcc agt gga 961
Ile Asn His Asn Leu Ala Val Met Tyr Arg Gln Val Ile Ser Ser Gly
305                 310                 315                 320 aag acg cca gag ctg ttt atg ggc tca gcg tac cgc gcc ggt gac cag 1009
Lys Thr Pro Glu Leu Phe Met Gly Ser Ala Tyr Arg Ala Gly Asp Gln
                325                 330                 335 cct gac ccc ggc gca ggc tct gta gag cag aag ccg cac ggc ccg gtg 1057
Pro Asp Pro Gly Ala Gly Ser Val Glu Gln Lys Pro His Gly Pro Val
            340                 345                 350 cat gtg tgg aca ggt gat cgc aac cag ccc aat cgc gaa gac atg ggc 1105
His Val Trp Thr Gly Asp Arg Asn Gln Pro Asn Arg Glu Asp Met Gly
        355                 360                 365 acg ctc tac tcg gcg gcg tgg gac ccc gtc ttc ttc gca cac cac ggc 1153
Thr Leu Tyr Ser Ala Ala Trp Asp Pro Val Phe Phe Ala His His Gly
    370                 375                 380 aac atc gac cgc atg tgg tac gtg tgg agg aac ctt ggc ggc aag cac 1201
Asn Ile Asp Arg Met Trp Tyr Val Trp Arg Asn Leu Gly Gly Lys His
385                 390                 395                 400 cgc aac ttc acc gac ccc gac tgg ctc aac gcg tcc ttc ctg ttc tat 1249
```

```
                                    Arg Asn Phe Thr Asp Pro Asp Trp Leu Asn Ala Ser Phe Leu Phe Tyr
                                                    405                 410                 415 gat gag aat gcg cag ctc gtc cgt gtt aaa gta aaa gac tgc tta gag         1297
Asp Glu Asn Ala Gln Leu Val Arg Val Lys Val Lys Asp Cys Leu Glu
            420                 425                 430 gcc gac gca atg cgg tac aca tac cag gat gta gag atc ccg tgg ctc         1345
Ala Asp Ala Met Arg Tyr Thr Tyr Gln Asp Val Glu Ile Pro Trp Leu
            435                 440                 445 aaa gca aag ccg acg cca aag agc gcc cta cag aag ata aag agc aag         1393
Lys Ala Lys Pro Thr Pro Lys Ser Ala Leu Gln Lys Ile Lys Ser Lys
    450                 455                 460 gta tcg acg ctg aag gca aca cca agg ggg acg acg act acc aca gca         1441
Val Ser Thr Leu Lys Ala Thr Pro Arg Gly Thr Thr Thr Thr Thr Ala
465                 470                 475                 480 gag act aca ttt ccg gtg gtg ctg gat aag ccg gtg agt gca aca gtg         1489
Glu Thr Thr Phe Pro Val Val Leu Asp Lys Pro Val Ser Ala Thr Val
                485                 490                 495 gct aga ccg aag gcc agg agg agt ggg aag gag aag gaa gaa gag gag         1537
Ala Arg Pro Lys Ala Arg Arg Ser Gly Lys Glu Lys Glu Glu Glu Glu
            500                 505                 510 gag gtg ttg gtg gtg gag gga atc gag ttg gag aag gac gtg ttc gtg         1585
Glu Val Leu Val Val Glu Gly Ile Glu Leu Glu Lys Asp Val Phe Val
        515                 520                 525 aag ttt gat gtg tat ata aac tcg ccg gag cac gaa ggg gtg ggg ccg         1633
Lys Phe Asp Val Tyr Ile Asn Ser Pro Glu His Glu Gly Val Gly Pro
    530                 535                 540 gag gcg agt gag ttc gca ggg agc ttc gtc cac gtg cca cac aag cac         1681
Glu Ala Ser Glu Phe Ala Gly Ser Phe Val His Val Pro His Lys His
545                 550                 555                 560 aag aag gcg aag aag ggg aag gag atg gcc agg atg aac aca agg ctt         1729
Lys Lys Ala Lys Lys Gly Lys Glu Met Ala Arg Met Asn Thr Arg Leu
                565                 570                 575 aag ctc ggg ata acg gac ctg ctc gag gac atc ggc gct gag gac gac         1777
Lys Leu Gly Ile Thr Asp Leu Leu Glu Asp Ile Gly Ala Glu Asp Asp
            580                 585                 590 gag agc gtg ctc atc acg ctc gtg ccc agg agc ggc aag gga atg gtg         1825
Glu Ser Val Leu Ile Thr Leu Val Pro Arg Ser Gly Lys Gly Met Val
        595                 600                 605 aag gtt gga ggg cta agg att gat ttc tcc aag tgatgagcat attgtgaaga      1878
Lys Val Gly Gly Leu Arg Ile Asp Phe Ser Lys
    610                 615 gaaaatttgc atttaccgcc ctatagaatc gaaaaattgc gtatatgtcc cattattgtt      1938 tttttttattc ttcaagcgta ttcagaataa gagttgcgtg catgcacgca tgcagccatg     1998
ttgttgtagt cgatatgtgg ggtatgtttg gatcagggat aatgatgtga actttgaatt     2058
aattattaca ctctgagaat aaattagaga gtttattatg caagttgctt ggtgtaatag     2118
atattcaaca ttgtttccta tacatctttt tttggaagaa aaaaaaaaaa aaaaaaaatc     2178
gat                                                                    2181

<210> SEQ ID NO 20
<211> LENGTH: 619
<212> TYPE: PRT
<213> ORGANISM: pineapple

<400> SEQUENCE: 20

Gly Ile Asp Lys Leu Asp Pro Val Pro Gly Leu Gly Val Phe Thr Met
 1               5                  10                  15

Ala Thr Leu Ser Lys Leu Ala Ser Gln Pro Ile Thr Pro Pro Leu Ser
```

-continued

```
                20                  25                  30
Pro Leu Pro Leu His Ala Pro Ser Leu Thr Lys Ser Phe Thr Thr
            35                  40                  45
Thr Phe Leu Ser Pro Val Gly Val Pro Asn His Pro Val Ile Arg Ser
        50                  55                  60
His Ala Asn Leu Arg Ser Asn Lys Arg Met Pro Thr Ser Leu Arg Ala
 65                  70                  75                  80
Ala Ser Pro Ala Ala Thr Tyr Ser Trp Ala Leu Gly Gly Leu Tyr Gly
                85                  90                  95
Ala Thr Thr Gly Leu Gly Leu Asn Arg Arg Ala Ala Ala Pro Ile
            100                 105                 110
Leu Ala Pro Asp Leu Ser Thr Cys Gly Pro Pro Ala Asp Leu Pro Ala
        115                 120                 125
Ser Ala Arg Pro Thr Val Cys Cys Pro Pro Tyr Gln Ser Thr Ile Ile
130                 135                 140
Asp Phe Lys Leu Pro Pro Arg Ser Ala Pro Leu Arg Val Arg Pro Ala
145                 150                 155                 160
Ala His Leu Val Asp Ala Asp Tyr Leu Ala Lys Tyr Lys Lys Ala Val
                165                 170                 175
Glu Leu Met Arg Ala Leu Pro Ala Asp Asp Pro Arg Asn Phe Val Gln
            180                 185                 190
Gln Ala Lys Val His Cys Ala Tyr Cys Asp Gly Ala Tyr Asp Gln Ile
        195                 200                 205
Gly Phe Pro Asp Leu Glu Ile Gln Ile His Asn Ser Trp Leu Phe Phe
210                 215                 220
Pro Trp His Arg Phe Tyr Leu Tyr Ser Asn Glu Arg Ile Leu Gly Lys
225                 230                 235                 240
Leu Ile Gly Asp Asp Thr Phe Ala Leu Pro Phe Trp Asn Trp Asp Ala
                245                 250                 255
Pro Gly Gly Met Gln Phe Pro Ser Ile Tyr Thr Asp Pro Ser Ser Ser
            260                 265                 270
Leu Tyr Asp Lys Leu Arg Asp Ala Lys His Gln Pro Pro Thr Leu Ile
        275                 280                 285
Asp Leu Asp Tyr Asn Gly Thr Asp Pro Thr Phe Ser Pro Glu Glu Gln
    290                 295                 300
Ile Asn His Asn Leu Ala Val Met Tyr Arg Gln Val Ile Ser Ser Gly
305                 310                 315                 320
Lys Thr Pro Glu Leu Phe Met Gly Ser Ala Tyr Arg Ala Gly Asp Gln
                325                 330                 335
Pro Asp Pro Gly Ala Gly Ser Val Glu Gln Lys Pro His Gly Pro Val
            340                 345                 350
His Val Trp Thr Gly Asp Arg Asn Gln Pro Asn Arg Glu Asp Met Gly
        355                 360                 365
Thr Leu Tyr Ser Ala Ala Trp Asp Pro Val Phe Phe Ala His His Gly
    370                 375                 380
Asn Ile Asp Arg Met Trp Tyr Val Trp Arg Asn Leu Gly Gly Lys His
385                 390                 395                 400
Arg Asn Phe Thr Asp Pro Asp Trp Leu Asn Ala Ser Phe Leu Phe Tyr
                405                 410                 415
Asp Glu Asn Ala Gln Leu Val Arg Val Lys Val Lys Asp Cys Leu Glu
            420                 425                 430
Ala Asp Ala Met Arg Tyr Thr Tyr Gln Asp Val Glu Ile Pro Trp Leu
        435                 440                 445
```

-continued

```
Lys Ala Lys Pro Thr Pro Lys Ser Ala Leu Gln Lys Ile Lys Ser Lys
    450                 455                 460

Val Ser Thr Leu Lys Ala Thr Pro Arg Gly Thr Thr Thr Thr Thr Ala
465                 470                 475                 480

Glu Thr Thr Phe Pro Val Val Leu Asp Lys Pro Val Ser Ala Thr Val
                485                 490                 495

Ala Arg Pro Lys Ala Arg Arg Ser Gly Lys Glu Lys Glu Glu Glu
            500                 505                 510

Glu Val Leu Val Val Glu Gly Ile Glu Leu Glu Lys Asp Val Phe Val
    515                 520                 525

Lys Phe Asp Val Tyr Ile Asn Ser Pro Glu His Glu Gly Val Gly Pro
    530                 535                 540

Glu Ala Ser Glu Phe Ala Gly Ser Phe Val His Val Pro His Lys His
545                 550                 555                 560

Lys Lys Ala Lys Lys Gly Lys Glu Met Ala Arg Met Asn Thr Arg Leu
                565                 570                 575

Lys Leu Gly Ile Thr Asp Leu Leu Glu Asp Ile Gly Ala Glu Asp Asp
            580                 585                 590

Glu Ser Val Leu Ile Thr Leu Val Pro Arg Ser Gly Lys Gly Met Val
    595                 600                 605

Lys Val Gly Gly Leu Arg Ile Asp Phe Ser Lys
    610                 615

<210> SEQ ID NO 21
<211> LENGTH: 2078
<212> TYPE: DNA
<213> ORGANISM: banana
<220> FEATURE:
<221> NAME/KEY: CDS
<222> LOCATION: (53)..(1822)

<400> SEQUENCE: 21
cacgccaccc ttctctctct ctctctctct ggtctactga acagtaatag ac atg tcc    58
                                                          Met Ser
                                                            1 ctg ctg ttg aac tct agc ttc acc ggt gct tcc tct gca tgc ctc ctc    106
Leu Leu Leu Asn Ser Ser Phe Thr Gly Ala Ser Ser Ala Cys Leu Leu
          5                  10                  15 caa cgg gaa agg tcc cgc cgc cgc cgc ctc cac gtc cct ggc gtg aca    154
Gln Arg Glu Arg Ser Arg Arg Arg Arg Leu His Val Pro Gly Val Thr
     20                  25                  30 tgc cgc cag ggc agt aat ggt gac cgc aga gat gcc gcc ccc cag cag    202
Cys Arg Gln Gly Ser Asn Gly Asp Arg Arg Asp Ala Ala Pro Gln Gln
 35                  40                  45                  50 cag tcg ccg ccg ctg ctg gat cgg cgc gac atg ctg ttg ggt tta gga    250
Gln Ser Pro Pro Leu Leu Asp Arg Arg Asp Met Leu Leu Gly Leu Gly
             55                  60                  65 ggg ctt tac ggc gtg acc gca gga ccc aag gtt ctg gcg gcg ccg ata    298
Gly Leu Tyr Gly Val Thr Ala Gly Pro Lys Val Leu Ala Ala Pro Ile
         70                  75                  80 atg ccg ccg gat ctg tcc aag tgc tac cct gcc acc gca cct gcc ctc    346
Met Pro Pro Asp Leu Ser Lys Cys Tyr Pro Ala Thr Ala Pro Ala Leu
     85                  90                  95 gac aac aaa tgc tgc ccg cct tac gac ccc ggc gag acg atc tcg gag    394
Asp Asn Lys Cys Cys Pro Pro Tyr Asp Pro Gly Glu Thr Ile Ser Glu
100                 105                 110 tac agc ttc cct gct acg ccc ctc cgg gtg cgg cgg ccg gcc cat atc    442
Tyr Ser Phe Pro Ala Thr Pro Leu Arg Val Arg Arg Pro Ala His Ile
            115                 120                 125
```

```
                   115                 120                 125                 130
gtg aag gac gat cag gag tat atg gac aag tac aag gag gca gtg agg         490
Val Lys Asp Asp Gln Glu Tyr Met Asp Lys Tyr Lys Glu Ala Val Arg
            135                 140                 145 agg atg aag aat ctg ccg gca gac cac cct tgg aac tac tac cag cag         538
Arg Met Lys Asn Leu Pro Ala Asp His Pro Trp Asn Tyr Tyr Gln Gln
            150                 155                 160 gcg aac atc cac tgc cag tat tgc aac tac gcc tac cac cag caa aat         586
Ala Asn Ile His Cys Gln Tyr Cys Asn Tyr Ala Tyr His Gln Gln Asn
            165                 170                 175 acc gac gac gtg ccc atc cag gtc cac ttc agc tgg atc ttc ctc cca         634
Thr Asp Asp Val Pro Ile Gln Val His Phe Ser Trp Ile Phe Leu Pro
            180                 185                 190 tgg cac cgc tac tac ctc cac ttc tac gaa agg atc ctc ggc aag ctc         682
Trp His Arg Tyr Tyr Leu His Phe Tyr Glu Arg Ile Leu Gly Lys Leu
195                 200                 205                 210 atc gac gac gac acc ttc acc atc cca ttc tgg aac tgg gac acc aag         730
Ile Asp Asp Asp Thr Phe Thr Ile Pro Phe Trp Asn Trp Asp Thr Lys
            215                 220                 225 gac ggg atg acg ttc ccc gcc atc ttc cag gat gcg gca tcc ccg ctg         778
Asp Gly Met Thr Phe Pro Ala Ile Phe Gln Asp Ala Ala Ser Pro Leu
            230                 235                 240 tac gac ccg aga cgc gac caa cgc cac gtc aag gac ggc aag atc ctc         826
Tyr Asp Pro Arg Arg Asp Gln Arg His Val Lys Asp Gly Lys Ile Leu
            245                 250                 255 gac ctc aag tac gcc tac acc gaa aac act gca tcc gac agc gag atc         874
Asp Leu Lys Tyr Ala Tyr Thr Glu Asn Thr Ala Ser Asp Ser Glu Ile
260                 265                 270 ata cgg gag aac ctc tgc ttc ata cag aag acg ttc aag cac agc ctg         922
Ile Arg Glu Asn Leu Cys Phe Ile Gln Lys Thr Phe Lys His Ser Leu
275                 280                 285                 290 tcg ctg gcg gaa ctg ttc atg ggg gat ccc gtg cgc gcg ggg gag aag         970
Ser Leu Ala Glu Leu Phe Met Gly Asp Pro Val Arg Ala Gly Glu Lys
            295                 300                 305 gag atc cag gag gct aat ggg cag atg gaa gtc atc cac aat gcg gcg        1018
Glu Ile Gln Glu Ala Asn Gly Gln Met Glu Val Ile His Asn Ala Ala
            310                 315                 320 cac atg tgg gtc gga gag ccg gac gga tac aag gaa aac atg ggg gac        1066
His Met Trp Val Gly Glu Pro Asp Gly Tyr Lys Glu Asn Met Gly Asp
            325                 330                 335 ttc tcc acc gcc gcc cgc gat tct gtt ttc ttc tgc cac cat tcc aat        1114
Phe Ser Thr Ala Ala Arg Asp Ser Val Phe Phe Cys His His Ser Asn
            340                 345                 350 gtc gac cgc atg tgg gac atc tac cgc aac ctc cgc ggc aac cgc gtc        1162
Val Asp Arg Met Trp Asp Ile Tyr Arg Asn Leu Arg Gly Asn Arg Val
355                 360                 365                 370 gag ttc gaa gac aac gac tgg ttg gac agc acc ttc ctc ttc cac gac        1210
Glu Phe Glu Asp Asn Asp Trp Leu Asp Ser Thr Phe Leu Phe His Asp
            375                 380                 385 gag aac gaa cag ctc gtc aaa gtc aag atg agc gac tgc ctc aac ccg        1258
Glu Asn Glu Gln Leu Val Lys Val Lys Met Ser Asp Cys Leu Asn Pro
            390                 395                 400 acc aag ctt cgg tac acg ttc gag caa gtt ccc ctc cca tgg ctg ggc        1306
Thr Lys Leu Arg Tyr Thr Phe Glu Gln Val Pro Leu Pro Trp Leu Gly
            405                 410                 415 aaa atc aat tgc cag aag acg gca gag acg aag tcc aag gcc acg acg        1354
Lys Ile Asn Cys Gln Lys Thr Ala Glu Thr Lys Ser Lys Ala Thr Thr
            420                 425                 430 gag ctg tcg ctg acg cgc gtg aac gaa ttc ggg acg acg gcc cag gca        1402
Glu Leu Ser Leu Thr Arg Val Asn Glu Phe Gly Thr Thr Ala Gln Ala
```

```
Glu Leu Ser Leu Thr Arg Val Asn Glu Phe Gly Thr Thr Ala Gln Ala
435                 440                 445                 450 ctc gac gcg agc aac ccg ctg cgg gtg atc gtg gca agg ccg aag aag    1450
Leu Asp Ala Ser Asn Pro Leu Arg Val Ile Val Ala Arg Pro Lys Lys
                455                 460                 465 aac cgc aag aag aag gag aag caa gag aag gtg ggg gtg att cag atc    1498
Asn Arg Lys Lys Lys Glu Lys Gln Glu Lys Val Gly Val Ile Gln Ile
            470                 475                 480 aag gat att aag gtg acc acc aac gag aca gct cgc ttc gac gtc tat    1546
Lys Asp Ile Lys Val Thr Thr Asn Glu Thr Ala Arg Phe Asp Val Tyr
        485                 490                 495 gtc gcg gtt cct tac ggt gac ctc gcc gga ccc gac tac ggc gag ttc    1594
Val Ala Val Pro Tyr Gly Asp Leu Ala Gly Pro Asp Tyr Gly Glu Phe
    500                 505                 510 gcg ggc agc tac gtg agg ctg gcg cat agg atg aag gga agc gac ggg    1642
Ala Gly Ser Tyr Val Arg Leu Ala His Arg Met Lys Gly Ser Asp Gly
515                 520                 525                 530 acc gaa aag cag ggc ccc aag aag aag gga aaa ctc aag ctg ggt att    1690
Thr Glu Lys Gln Gly Pro Lys Lys Lys Gly Lys Leu Lys Leu Gly Ile
                535                 540                 545 acg ccg ctc ctc gag gac atc gat gct gag gac gcc gac aag ttg gtg    1738
Thr Pro Leu Leu Glu Asp Ile Asp Ala Glu Asp Ala Asp Lys Leu Val
            550                 555                 560 gtc acc ctg gtt ctc cgc act ggg agc gtc acc gtg ggg gga gtt tcc    1786
Val Thr Leu Val Leu Arg Thr Gly Ser Val Thr Val Gly Gly Val Ser
        565                 570                 575 atc aat ctc ctg cag aca gat tct acc gcc gcc atc taaatgatgg         1832
Ile Asn Leu Leu Gln Thr Asp Ser Thr Ala Ala Ile
    580                 585                 590 cctcggatca cagcttctcc ccgcttaagt tggagtgatc gattactggt gctgctttct  1892
tcctccctgt cgttcttgct atcttcttga tctggaacga tccttcaata attagggcat  1952
gacagtagtc gtcgcccgat cccatatgta cgtgttggtc tcaacagctg tacatgtgac  2012
gttatggtgt gactatatat tttattgcgg tcatccttgt ttctttctta aaaaaaaaaa  2072
aaaaaa                                                             2078

<210> SEQ ID NO 22
<211> LENGTH: 590
<212> TYPE: PRT
<213> ORGANISM: banana

<400> SEQUENCE: 22

Met Ser Leu Leu Leu Asn Ser Ser Phe Thr Gly Ala Ser Ser Ala Cys
1               5                   10                  15

Leu Leu Gln Arg Glu Arg Ser Arg Arg Arg Leu His Val Pro Gly
            20                  25                  30

Val Thr Cys Arg Gln Gly Ser Asn Gly Asp Arg Arg Asp Ala Ala Pro
            35                  40                  45

Gln Gln Gln Ser Pro Pro Leu Leu Asp Arg Arg Asp Met Leu Leu Gly
        50                  55                  60

Leu Gly Gly Leu Tyr Gly Val Thr Ala Gly Pro Lys Val Leu Ala Ala
65                  70                  75                  80

Pro Ile Met Pro Pro Asp Leu Ser Lys Cys Tyr Pro Ala Thr Ala Pro
                85                  90                  95

Ala Leu Asp Asn Lys Cys Cys Pro Pro Tyr Asp Pro Gly Glu Thr Ile
            100                 105                 110

Ser Glu Tyr Ser Phe Pro Ala Thr Pro Leu Arg Val Arg Arg Pro Ala
```

-continued

```
                115                 120                 125
His Ile Val Lys Asp Asp Gln Glu Tyr Met Asp Lys Tyr Lys Glu Ala
            130                 135                 140

Val Arg Arg Met Lys Asn Leu Pro Ala Asp His Pro Trp Asn Tyr Tyr
145                 150                 155                 160

Gln Gln Ala Asn Ile His Cys Gln Tyr Cys Asn Tyr Ala Tyr His Gln
                165                 170                 175

Gln Asn Thr Asp Asp Val Pro Ile Gln Val His Phe Ser Trp Ile Phe
            180                 185                 190

Leu Pro Trp His Arg Tyr Tyr Leu His Phe Tyr Glu Arg Ile Leu Gly
                195                 200                 205

Lys Leu Ile Asp Asp Thr Phe Thr Ile Pro Phe Trp Asn Trp Asp
210                 215                 220

Thr Lys Asp Gly Met Thr Phe Pro Ala Ile Phe Gln Asp Ala Ala Ser
225                 230                 235                 240

Pro Leu Tyr Asp Pro Arg Arg Asp Gln Arg His Val Lys Asp Gly Lys
                245                 250                 255

Ile Leu Asp Leu Lys Tyr Ala Tyr Thr Glu Asn Thr Ala Ser Asp Ser
            260                 265                 270

Glu Ile Ile Arg Glu Asn Leu Cys Phe Ile Gln Lys Thr Phe Lys His
275                 280                 285

Ser Leu Ser Leu Ala Glu Leu Phe Met Gly Asp Pro Val Arg Ala Gly
            290                 295                 300

Glu Lys Glu Ile Gln Glu Ala Asn Gly Gln Met Glu Val Ile His Asn
305                 310                 315                 320

Ala Ala His Met Trp Val Gly Glu Pro Asp Gly Tyr Lys Glu Asn Met
                325                 330                 335

Gly Asp Phe Ser Thr Ala Ala Arg Asp Ser Val Phe Phe Cys His His
            340                 345                 350

Ser Asn Val Asp Arg Met Trp Asp Ile Tyr Arg Asn Leu Arg Gly Asn
            355                 360                 365

Arg Val Glu Phe Glu Asp Asn Asp Trp Leu Asp Ser Thr Phe Leu Phe
370                 375                 380

His Asp Glu Asn Glu Gln Leu Val Lys Val Lys Met Ser Asp Cys Leu
385                 390                 395                 400

Asn Pro Thr Lys Leu Arg Tyr Thr Phe Glu Gln Val Pro Leu Pro Trp
                405                 410                 415

Leu Gly Lys Ile Asn Cys Gln Lys Thr Ala Glu Thr Lys Ser Lys Ala
            420                 425                 430

Thr Thr Glu Leu Ser Leu Thr Arg Val Asn Glu Phe Gly Thr Thr Ala
            435                 440                 445

Gln Ala Leu Asp Ala Ser Asn Pro Leu Arg Val Ile Ala Arg Pro
450                 455                 460

Lys Lys Asn Arg Lys Lys Glu Lys Gln Glu Lys Val Gly Val Ile
465                 470                 475                 480

Gln Ile Lys Asp Ile Lys Val Thr Thr Asn Glu Thr Ala Arg Phe Asp
                485                 490                 495

Val Tyr Val Ala Val Pro Tyr Gly Asp Leu Ala Gly Pro Asp Tyr Gly
            500                 505                 510

Glu Phe Ala Gly Ser Tyr Val Arg Leu Ala His Arg Met Lys Gly Ser
            515                 520                 525

Asp Gly Thr Glu Lys Gln Gly Pro Lys Lys Gly Lys Leu Lys Leu
530                 535                 540
```

```
Gly Ile Thr Pro Leu Leu Glu Asp Ile Asp Ala Glu Asp Ala Asp Lys
545                 550                 555                 560

Leu Val Val Thr Leu Val Leu Arg Thr Gly Ser Val Thr Val Gly Gly
                565                 570                 575

Val Ser Ile Asn Leu Leu Gln Thr Asp Ser Thr Ala Ala Ile
            580                 585                 590

<210> SEQ ID NO 23
<211> LENGTH: 900
<212> TYPE: DNA
<213> ORGANISM: banana
<220> FEATURE:
<221> NAME/KEY: CDS
<222> LOCATION: (13)..(729)

<400> SEQUENCE: 23
aatgtggatc gg atg tgg acg gtg tgg aag aag ctg cac ggc gac aag ccg      51
              Met Trp Thr Val Trp Lys Lys Leu His Gly Asp Lys Pro
                1               5                  10 gag ttc gtc gac cag gag tgg ctc gag tct gaa ttc acc ttc tac gac       99
Glu Phe Val Asp Gln Glu Trp Leu Glu Ser Glu Phe Thr Phe Tyr Asp
 15                  20                  25 gag aat gtg cgc ctg cgc agg atc aag gtg cgc gac gtg ttg aac ata      147
Glu Asn Val Arg Leu Arg Arg Ile Lys Val Arg Asp Val Leu Asn Ile
 30                  35                  40                  45 gac aaa ctc agg tac cgg tac gaa gac atc gac atg cca tgg ctc gct      195
Asp Lys Leu Arg Tyr Arg Tyr Glu Asp Ile Asp Met Pro Trp Leu Ala
             50                  55                  60 gca cgt ccc aag cct tcc gtt cac cct aag atc gcg cgc gac ata ttg      243
Ala Arg Pro Lys Pro Ser Val His Pro Lys Ile Ala Arg Asp Ile Leu
         65                  70                  75 aag aag cgt aat ggc gaa ggc gta ctg aga atg ccc ggc gaa acg gat      291
Lys Lys Arg Asn Gly Glu Gly Val Leu Arg Met Pro Gly Glu Thr Asp
     80                  85                  90 cgt tca caa ctc tcc gaa gat ggt agc tgg aca ctg gac aag agc atc      339
Arg Ser Gln Leu Ser Glu Asp Gly Ser Trp Thr Leu Asp Lys Ser Ile
 95                 100                 105 acc gtg agg gtt gac agg cca agg atc aac agg aca ggg caa gaa aaa      387
Thr Val Arg Val Asp Arg Pro Arg Ile Asn Arg Thr Gly Gln Glu Lys
110                 115                 120                 125 gag gaa gaa gag gag atc tta ttg gtc tac gga atc gat act aag aga      435
Glu Glu Glu Glu Glu Ile Leu Leu Val Tyr Gly Ile Asp Thr Lys Arg
                130                 135                 140 agc aga ttc gtc aaa ttc gat gtg ttc atc aac gtc gtc gac gaa acc      483
Ser Arg Phe Val Lys Phe Asp Val Phe Ile Asn Val Val Asp Glu Thr
            145                 150                 155 gtg ctg aac cca aag tcg agg gag ttc gca ggg acc ttc gtc aat ctc      531
Val Leu Asn Pro Lys Ser Arg Glu Phe Ala Gly Thr Phe Val Asn Leu
        160                 165                 170 cac cac gtc tcg agg acg aaa agc cat gag gat ggc ggc gtg ggt tcg      579
His His Val Ser Arg Thr Lys Ser His Glu Asp Gly Gly Val Gly Ser
    175                 180                 185 aag atg aaa agc cac ctt aag ctc ggt ata tcg gaa ctt ttg gaa gac      627
Lys Met Lys Ser His Leu Lys Leu Gly Ile Ser Glu Leu Leu Glu Asp
190                 195                 200                 205 ctc gag gca gac gaa gat gat tgc atc tgg gtg aca ctg gtg cca aga      675
Leu Glu Ala Asp Glu Asp Asp Cys Ile Trp Val Thr Leu Val Pro Arg
                210                 215                 220 ggc ggc acg ggg gtc aac acc acc gta gac ggc gtc cgg atc gac tac      723
Gly Gly Thr Gly Val Asn Thr Thr Val Asp Gly Val Arg Ile Asp Tyr
```

-continued

```
                  225                 230                 235
atg aag tagtgaaccg gcacgccgct cctcccctcc ccatcagaag tggtataata      779
Met Lys tttatattgg atcgaggctc gtggtatctt tgataagag taagttccat aaatttagaa    839
gaagaatcat gttctttatt tatattaaat caatgtgatt tgtccaaaaa aaaaaaaaaa   899
a                                                                  900
```

<210> SEQ ID NO 24
<211> LENGTH: 239
<212> TYPE: PRT
<213> ORGANISM: banana

<400> SEQUENCE: 24

```
Met Trp Thr Val Trp Lys Lys Leu His Gly Asp Lys Pro Glu Phe Val
  1               5                  10                  15

Asp Gln Glu Trp Leu Glu Ser Glu Phe Thr Phe Tyr Asp Glu Asn Val
             20                  25                  30

Arg Leu Arg Arg Ile Lys Val Arg Asp Val Leu Asn Ile Asp Lys Leu
         35                  40                  45

Arg Tyr Arg Tyr Glu Asp Ile Asp Met Pro Trp Leu Ala Ala Arg Pro
     50                  55                  60

Lys Pro Ser Val His Pro Lys Ile Ala Arg Asp Ile Leu Lys Lys Arg
 65                  70                  75                  80

Asn Gly Glu Gly Val Leu Arg Met Pro Gly Glu Thr Asp Arg Ser Gln
                 85                  90                  95

Leu Ser Glu Asp Gly Ser Trp Thr Leu Asp Lys Ser Ile Thr Val Arg
            100                 105                 110

Val Asp Arg Pro Arg Ile Asn Arg Thr Gly Gln Glu Lys Glu Glu Glu
        115                 120                 125

Glu Glu Ile Leu Leu Val Tyr Gly Ile Asp Thr Lys Arg Ser Arg Phe
    130                 135                 140

Val Lys Phe Asp Val Phe Ile Asn Val Val Asp Glu Thr Val Leu Asn
145                 150                 155                 160

Pro Lys Ser Arg Glu Phe Ala Gly Thr Phe Val Asn Leu His His Val
                165                 170                 175

Ser Arg Thr Lys Ser His Glu Asp Gly Val Gly Ser Lys Met Lys
            180                 185                 190

Ser His Leu Lys Leu Gly Ile Ser Glu Leu Leu Glu Asp Leu Glu Ala
        195                 200                 205

Asp Glu Asp Asp Cys Ile Trp Val Thr Leu Val Pro Arg Gly Gly Thr
    210                 215                 220

Gly Val Asn Thr Thr Val Asp Gly Val Arg Ile Asp Tyr Met Lys
225                 230                 235
```

<210> SEQ ID NO 25
<211> LENGTH: 1522
<212> TYPE: DNA
<213> ORGANISM: pineapple
<220> FEATURE:
<221> NAME/KEY: CDS
<222> LOCATION: (3)..(1271)

<400> SEQUENCE: 25

```
tg cac tgt gcg tat tgc gac ggc gcg tat gac caa atc ggc ttc ccc     47
   His Cys Ala Tyr Cys Asp Gly Ala Tyr Asp Gln Ile Gly Phe Pro
    1               5                  10                  15
```

```
gat ctc gag atc cag atc cac aac tcg tgg ctc ttt cct tgg cac        95
Asp Leu Glu Ile Gln Ile His Asn Ser Trp Leu Phe Pro Trp His
         20                  25                  30 cgg ttc tac ctc tac tcc aac gag cgc ata ctc ggg aaa ctt atc ggc   143
Arg Phe Tyr Leu Tyr Ser Asn Glu Arg Ile Leu Gly Lys Leu Ile Gly
             35                  40                  45 gac gac acg ttc gcg ctg cct ttc tgg aac tgg gac gcg ccg ggg ggc   191
Asp Asp Thr Phe Ala Leu Pro Phe Trp Asn Trp Asp Ala Pro Gly Gly
                 50                  55                  60 atg cag ttc ccg tct atc tac acg gac cct tca tcc tcg cta tat gac   239
Met Gln Phe Pro Ser Ile Tyr Thr Asp Pro Ser Ser Ser Leu Tyr Asp
 65                  70                  75 aag ctg cgt gat gcg aag cac cag ccg ccg act ttg att gac ctc gac   287
Lys Leu Arg Asp Ala Lys His Gln Pro Pro Thr Leu Ile Asp Leu Asp
 80                  85                  90                  95 tac aat ggc acc gat cct acc ttc tcc cct gaa gaa cag att aac cac   335
Tyr Asn Gly Thr Asp Pro Thr Phe Ser Pro Glu Glu Gln Ile Asn His
                100                 105                 110 aac ctc gcc gtc atg tac cga cag gtg ata tcc agt gga aag aca cca   383
Asn Leu Ala Val Met Tyr Arg Gln Val Ile Ser Ser Gly Lys Thr Pro
                    115                 120                 125 gag ctg ttt atg ggc tca gcg tac cgc gcc ggt gac cag cct gac ccc   431
Glu Leu Phe Met Gly Ser Ala Tyr Arg Ala Gly Asp Gln Pro Asp Pro
        130                 135                 140 ggc gca ggc tct gta gag cag aag ccg cac ggc ccg gtg cat gtg tgg   479
Gly Ala Gly Ser Val Glu Gln Lys Pro His Gly Pro Val His Val Trp
145                 150                 155 aca ggt gat cgc aac cag ccc aat cgc gaa gac atg ggc acg ctc tac   527
Thr Gly Asp Arg Asn Gln Pro Asn Arg Glu Asp Met Gly Thr Leu Tyr
160                 165                 170                 175 tcg gcg gcg tgg gac ccc gtc ttc ttc gca cac cac ggc aac atc gac   575
Ser Ala Ala Trp Asp Pro Val Phe Phe Ala His His Gly Asn Ile Asp
                180                 185                 190 cgc atg tgg tac gtg tgg agg aac ctt ggc ggc aag cac cgc aac ttc   623
Arg Met Trp Tyr Val Trp Arg Asn Leu Gly Gly Lys His Arg Asn Phe
                    195                 200                 205 acc gac ccc gac tgg ctc aac gcg tcc ttc ctg ttc tat gat gag aat   671
Thr Asp Pro Asp Trp Leu Asn Ala Ser Phe Leu Phe Tyr Asp Glu Asn
        210                 215                 220 gcg cag ctc gtc cgt gtt aaa gta aaa gac tgc tta gag gcc gac gca   719
Ala Gln Leu Val Arg Val Lys Val Lys Asp Cys Leu Glu Ala Asp Ala
225                 230                 235 atg cgg tac aca tac cag gat gta gag atc ccg tgg ctc aaa gca aag   767
Met Arg Tyr Thr Tyr Gln Asp Val Glu Ile Pro Trp Leu Lys Ala Lys
240                 245                 250                 255 ccg acg cca aag agc gcc cta cag aag ata aag agc aag gta tcg acg   815
Pro Thr Pro Lys Ser Ala Leu Gln Lys Ile Lys Ser Lys Val Ser Thr
                260                 265                 270 ctg aag gca aca cca agg ggg acg acg act acc aca gca gag act aca   863
Leu Lys Ala Thr Pro Arg Gly Thr Thr Thr Thr Thr Ala Glu Thr Thr
                    275                 280                 285 ttt ccg gtg gtg ctg gat aag ccg gtg agt gca aca gtg gct aga ccg   911
Phe Pro Val Val Leu Asp Lys Pro Val Ser Ala Thr Val Ala Arg Pro
        290                 295                 300 aag gcc agg agg agt ggg aag gag aag gaa gaa gag gag gag gtg ttg   959
Lys Ala Arg Arg Ser Gly Lys Glu Lys Glu Glu Glu Glu Glu Val Leu
305                 310                 315 gtg gtg gag gga atc gag ttg gag aag gac gtg ttc gtg aag ttt gat  1007
Val Val Glu Gly Ile Glu Leu Glu Lys Asp Val Phe Val Lys Phe Asp
320                 325                 330                 335
```

-continued

```
gtg tat ata aac tcg ccg gag cac gaa ggg gtg ggg ccg gag gcg agt      1055
Val Tyr Ile Asn Ser Pro Glu His Glu Gly Val Gly Pro Glu Ala Ser
                340                 345                 350 gag ttc gca ggg agc ttc gtc cac gtg cca cac aag cac aag aag gcg      1103
Glu Phe Ala Gly Ser Phe Val His Val Pro His Lys His Lys Lys Ala
                355                 360                 365 aag aag ggg aag gag atg gcc agg atg aac aca agg ctt aag ctc ggg      1151
Lys Lys Gly Lys Glu Met Ala Arg Met Asn Thr Arg Leu Lys Leu Gly
            370                 375                 380 ata acg gac ctg ctc gag gac atc ggc gct gag gac gac gag agc gtg      1199
Ile Thr Asp Leu Leu Glu Asp Ile Gly Ala Glu Asp Asp Glu Ser Val
        385                 390                 395 ctc atc acg ctc gtg ccc agg agc ggc aag gga atg gtg aag gtt gga      1247
Leu Ile Thr Leu Val Pro Arg Ser Gly Lys Gly Met Val Lys Val Gly
400                 405                 410                 415 ggg cta agg att gat ttc tcc aag tgatgagcat attgtgaaga gaaaatttgc     1301
Gly Leu Arg Ile Asp Phe Ser Lys
                420 atttaccgcc ctatagaatc gaaaaattgc gtatatgtcc cattattgtt tttttttattc   1361 ttcaagcgta ttcagaataa gagttgcgtg catgcacgca tgcagccatg ttgttgtagt    1421 cgatatgtgg ggtatgtttg gatcagggat aatgatgtga actttgaatt aattattaca   1481 ctctgagaat aaattagaga gtttattatg caaaaaaaaa a                        1522

<210> SEQ ID NO 26
<211> LENGTH: 423
<212> TYPE: PRT
<213> ORGANISM: pineapple

<400> SEQUENCE: 26

His Cys Ala Tyr Cys Asp Gly Ala Tyr Asp Gln Ile Gly Phe Pro Asp
 1               5                  10                  15

Leu Glu Ile Gln Ile His Asn Ser Trp Leu Phe Phe Pro Trp His Arg
                20                  25                  30

Phe Tyr Leu Tyr Ser Asn Glu Arg Ile Leu Gly Lys Leu Ile Gly Asp
            35                  40                  45

Asp Thr Phe Ala Leu Pro Phe Trp Asn Trp Asp Ala Pro Gly Gly Met
        50                  55                  60

Gln Phe Pro Ser Ile Tyr Thr Asp Pro Ser Ser Ser Leu Tyr Asp Lys
65                  70                  75                  80

Leu Arg Asp Ala Lys His Gln Pro Pro Thr Leu Ile Asp Leu Asp Tyr
                85                  90                  95

Asn Gly Thr Asp Pro Thr Phe Ser Pro Glu Glu Gln Ile Asn His Asn
            100                 105                 110

Leu Ala Val Met Tyr Arg Gln Val Ile Ser Ser Gly Lys Thr Pro Glu
        115                 120                 125

Leu Phe Met Gly Ser Ala Tyr Arg Ala Gly Asp Gln Pro Asp Pro Gly
    130                 135                 140

Ala Gly Ser Val Glu Gln Lys Pro His Gly Pro Val His Val Trp Thr
145                 150                 155                 160

Gly Asp Arg Asn Gln Pro Asn Arg Glu Asp Met Gly Thr Leu Tyr Ser
                165                 170                 175

Ala Ala Trp Asp Pro Val Phe Phe Ala His His Gly Asn Ile Asp Arg
            180                 185                 190

Met Trp Tyr Val Trp Arg Asn Leu Gly Gly Lys His Arg Asn Phe Thr
        195                 200                 205
```

-continued

```
Asp Pro Asp Trp Leu Asn Ala Ser Phe Leu Phe Tyr Asp Glu Asn Ala
    210                 215                 220

Gln Leu Val Arg Val Lys Val Lys Asp Cys Leu Glu Ala Asp Ala Met
225                 230                 235                 240

Arg Tyr Thr Tyr Gln Asp Val Glu Ile Pro Trp Leu Lys Ala Lys Pro
                245                 250                 255

Thr Pro Lys Ser Ala Leu Gln Lys Ile Lys Ser Lys Val Ser Thr Leu
            260                 265                 270

Lys Ala Thr Pro Arg Gly Thr Thr Thr Thr Ala Glu Thr Thr Phe
            275                 280                 285

Pro Val Val Leu Asp Lys Pro Val Ser Ala Thr Val Ala Arg Pro Lys
    290                 295                 300

Ala Arg Arg Ser Gly Lys Glu Lys Glu Glu Glu Glu Val Leu Val
305                 310                 315                 320

Val Glu Gly Ile Glu Leu Glu Lys Asp Val Phe Val Lys Phe Asp Val
                325                 330                 335

Tyr Ile Asn Ser Pro Glu His Glu Gly Val Gly Pro Glu Ala Ser Glu
            340                 345                 350

Phe Ala Gly Ser Phe Val His Val Pro His Lys His Lys Ala Lys
        355                 360                 365

Lys Gly Lys Glu Met Ala Arg Met Asn Thr Arg Leu Lys Leu Gly Ile
370                 375                 380

Thr Asp Leu Leu Glu Asp Ile Gly Ala Glu Asp Asp Glu Ser Val Leu
385                 390                 395                 400

Ile Thr Leu Val Pro Arg Ser Gly Lys Gly Met Val Lys Val Gly Gly
                405                 410                 415

Leu Arg Ile Asp Phe Ser Lys
            420

<210> SEQ ID NO 27
<211> LENGTH: 875
<212> TYPE: DNA
<213> ORGANISM: pineapple
<220> FEATURE:
<221> NAME/KEY: CDS
<222> LOCATION: (3)..(875)

<400> SEQUENCE: 27 ac aac aaa cca gtg cct ggt tta ggt gta ttc act atg gcc acc ctc      47
   Asn Lys Pro Val Pro Gly Leu Gly Val Phe Thr Met Ala Thr Leu
    1               5                  10                  15 tct aaa cta gct tcc cca acc aat aac acc tcc act ctc ccc gct ccc      95
Ser Lys Leu Ala Ser Pro Thr Asn Asn Thr Ser Thr Leu Pro Ala Pro
            20                  25                  30 tcc ttt gca tgc tcc ttc tct cac caa aag ctt cac cac cac ctt cct     143
Ser Phe Ala Cys Ser Phe Ser His Gln Lys Leu His His His Leu Pro
        35                  40                  45 ctc ccc tgt agg ggt ccc aaa cca ccc cgt cat aag atc tca tgc aaa     191
Leu Pro Cys Arg Gly Pro Lys Pro Pro Arg His Lys Ile Ser Cys Lys
    50                  55                  60 tct aag gag caa caa gag aat gcc gac aag cct gcg ggc cgc atc gac     239
Ser Lys Glu Gln Gln Glu Asn Ala Asp Lys Pro Ala Gly Arg Ile Asp
65                  70                  75 cgc cgc gac cta ctc ctg ggc ctc ggc ggg ctt tac ggt gcc acc act     287
Arg Arg Asp Leu Leu Leu Gly Leu Gly Gly Leu Tyr Gly Ala Thr Thr
80                  85                  90                  95 ggg ctc ggc ctc aac cgt cga gcg gcc gcc gcc cct atc ctg gct ccc     335
```

```
                                                    -continued

Gly Leu Gly Leu Asn Arg Arg Ala Ala Ala Pro Ile Leu Ala Pro
            100                 105                 110 gac ctc tca act tgt ggg ccg cct gcc gac ctc cct gcc tcc gcc cga    383
Asp Leu Ser Thr Cys Gly Pro Pro Ala Asp Leu Pro Ala Ser Ala Arg
            115                 120                 125 ccg aca gtt tgc tgc ccg cca tac caa tcc acc atc atc gtc ttc aag    431
Pro Thr Val Cys Cys Pro Pro Tyr Gln Ser Thr Ile Ile Val Phe Lys
            130                 135                 140 ctc ccc ccg cga tct gct ccg ctt cgc gtc cgg cct gcg gcc cac ttg    479
Leu Pro Pro Arg Ser Ala Pro Leu Arg Val Arg Pro Ala Ala His Leu
145                 150                 155 gtt gac gcc gac tac ctg gcc aag tat aag aag gcg gtc gag ctc atg    527
Val Asp Ala Asp Tyr Leu Ala Lys Tyr Lys Lys Ala Val Glu Leu Met
160                 165                 170                 175 agg gcc ctg ccg gcc gac gac ccg cgc aac ttc gta cag caa gcg aaa    575
Arg Ala Leu Pro Ala Asp Asp Pro Arg Asn Phe Val Gln Gln Ala Lys
                180                 185                 190 gtg cac tgt gcg tac tgc gac ggc gcg tac gac caa atc ggc ttc ccc    623
Val His Cys Ala Tyr Cys Asp Gly Ala Tyr Asp Gln Ile Gly Phe Pro
            195                 200                 205 gat ctc gag atc cag atc cac aac tcg tgg ctc ttc ttt cct tgg cac    671
Asp Leu Glu Ile Gln Ile His Asn Ser Trp Leu Phe Phe Pro Trp His
            210                 215                 220 cgg ttc tac ctc tac ttc aac gag cgc ata ctc ggg aaa ctt atc ggt    719
Arg Phe Tyr Leu Tyr Phe Asn Glu Arg Ile Leu Gly Lys Leu Ile Gly
225                 230                 235 gac gac acg ttc gcg ctg cct ttc tgg aac tgg gac gcg ccg ggg ggc    767
Asp Asp Thr Phe Ala Leu Pro Phe Trp Asn Trp Asp Ala Pro Gly Gly
240                 245                 250                 255 atg cag ttc ccg tct atc tac aca gac cct tca tcc tcg cta tat gac    815
Met Gln Phe Pro Ser Ile Tyr Thr Asp Pro Ser Ser Ser Leu Tyr Asp
                260                 265                 270 aag ctg cgt gat gcg aag cac cag ccg ccg act ttg att gac ctc gac    863
Lys Leu Arg Asp Ala Lys His Gln Pro Pro Thr Leu Ile Asp Leu Asp
            275                 280                 285 tac aat ggc aca                                                    875
Tyr Asn Gly Thr
        290

<210> SEQ ID NO 28
<211> LENGTH: 291
<212> TYPE: PRT
<213> ORGANISM: pineapple

<400> SEQUENCE: 28

Asn Lys Pro Val Pro Gly Leu Gly Val Phe Thr Met Ala Thr Leu Ser
1               5                   10                  15

Lys Leu Ala Ser Pro Thr Asn Asn Thr Ser Thr Leu Pro Ala Pro Ser
            20                  25                  30

Phe Ala Cys Ser Phe Ser His Gln Lys Leu His His Leu Pro Leu
        35                  40                  45

Pro Cys Arg Gly Pro Lys Pro Arg His Lys Ile Ser Cys Lys Ser
    50                  55                  60

Lys Glu Gln Gln Glu Asn Ala Asp Lys Pro Ala Gly Arg Ile Asp Arg
65                  70                  75                  80

Arg Asp Leu Leu Leu Gly Leu Gly Leu Tyr Gly Ala Thr Thr Gly
                85                  90                  95

Leu Gly Leu Asn Arg Arg Ala Ala Ala Ala Pro Ile Leu Ala Pro Asp
            100                 105                 110
```

-continued

```
Leu Ser Thr Cys Gly Pro Pro Ala Asp Leu Pro Ala Ser Ala Arg Pro
        115                 120                 125

Thr Val Cys Cys Pro Pro Tyr Gln Ser Thr Ile Ile Val Phe Lys Leu
    130                 135                 140

Pro Pro Arg Ser Ala Pro Leu Arg Val Arg Pro Ala Ala His Leu Val
145                 150                 155                 160

Asp Ala Asp Tyr Leu Ala Lys Tyr Lys Ala Val Glu Leu Met Arg
                165                 170                 175

Ala Leu Pro Ala Asp Asp Pro Arg Asn Phe Val Gln Gln Ala Lys Val
            180                 185                 190

His Cys Ala Tyr Cys Asp Gly Ala Tyr Asp Gln Ile Gly Phe Pro Asp
        195                 200                 205

Leu Glu Ile Gln Ile His Asn Ser Trp Leu Phe Phe Pro Trp His Arg
    210                 215                 220

Phe Tyr Leu Tyr Phe Asn Glu Arg Ile Leu Gly Lys Leu Ile Gly Asp
225                 230                 235                 240

Asp Thr Phe Ala Leu Pro Phe Trp Asn Trp Asp Ala Pro Gly Gly Met
                245                 250                 255

Gln Phe Pro Ser Ile Tyr Thr Asp Pro Ser Ser Leu Tyr Asp Lys
            260                 265                 270

Leu Arg Asp Ala Lys His Gln Pro Pro Thr Leu Ile Asp Leu Asp Tyr
        275                 280                 285

Asn Gly Thr
    290

<210> SEQ ID NO 29
<211> LENGTH: 2057
<212> TYPE: DNA
<213> ORGANISM: lettuce
<220> FEATURE:
<221> NAME/KEY: CDS
<222> LOCATION: (16)..(1842)

<400> SEQUENCE: 29
gaccacccat agatg atg gct tct ctc gcc ttg tct agt ctt ccc acc tcc      51
              Met Ala Ser Leu Ala Leu Ser Ser Leu Pro Thr Ser
                1               5                  10 acc aca acc aaa aaa ccc tta ttt tcc aaa aca tcc tcg cat gtt aag      99
Thr Thr Thr Lys Lys Pro Leu Phe Ser Lys Thr Ser Ser His Val Lys
            15                  20                  25 cca ttc cat cgc ttc aaa gtt tca tgc aat gca ccc gct gat aac aat     147
Pro Phe His Arg Phe Lys Val Ser Cys Asn Ala Pro Ala Asp Asn Asn
 30                  35                  40 gac aaa acc gtc aat aat tct gat acc cca aag ctc ata cta ccc aaa     195
Asp Lys Thr Val Asn Asn Ser Asp Thr Pro Lys Leu Ile Leu Pro Lys
 45                  50                  55                  60 aca cca ctt gaa acg cag aac gta gac agg aga aac ttg ctt ctg gga     243
Thr Pro Leu Glu Thr Gln Asn Val Asp Arg Arg Asn Leu Leu Leu Gly
                 65                  70                  75 ctc gga ggt ctc tac ggc gct gcc aac ttg acg acc att ccg tca gcc     291
Leu Gly Gly Leu Tyr Gly Ala Ala Asn Leu Thr Thr Ile Pro Ser Ala
             80                  85                  90 ttt ggc att ccc atc gct gct cca gac aat att tca gac tgt gtt gct     339
Phe Gly Ile Pro Ile Ala Ala Pro Asp Asn Ile Ser Asp Cys Val Ala
         95                 100                 105 gcg act tca aac cta agg aac agc aaa gac gct ata agg gga cta gcg     387
Ala Thr Ser Asn Leu Arg Asn Ser Lys Asp Ala Ile Arg Gly Leu Ala
    110                 115                 120
```

-continued

```
tgt tgt cct ccg gtg ctt tca aca aac aaa cca atg gat tac gtc ctt      435
Cys Cys Pro Pro Val Leu Ser Thr Asn Lys Pro Met Asp Tyr Val Leu
125                 130                 135                 140 cct tca aac cct gtg att cgt gtt cga cca gct gca cag aaa gcc act      483
Pro Ser Asn Pro Val Ile Arg Val Arg Pro Ala Ala Gln Lys Ala Thr
                145                 150                 155 gcc gat tac act gct aag tat caa caa gca att caa gcc atg aag gat      531
Ala Asp Tyr Thr Ala Lys Tyr Gln Gln Ala Ile Gln Ala Met Lys Asp
            160                 165                 170 ctc ccc gag gac cac cca cat agc tgg aag caa caa ggc aag att cac      579
Leu Pro Glu Asp His Pro His Ser Trp Lys Gln Gln Gly Lys Ile His
        175                 180                 185 tgt gct tat tgc aac ggt ggt tac aat caa gaa caa agt ggt tac ccg      627
Cys Ala Tyr Cys Asn Gly Gly Tyr Asn Gln Glu Gln Ser Gly Tyr Pro
    190                 195                 200 aat tta caa ctt cag att cac aac tca tgg ctc ttc ttt cct ttc cac      675
Asn Leu Gln Leu Gln Ile His Asn Ser Trp Leu Phe Phe Pro Phe His
205                 210                 215                 220 cgg tgg tac ctc tat ttc tac gag aag ata ttg ggg aag ttg att aat      723
Arg Trp Tyr Leu Tyr Phe Tyr Glu Lys Ile Leu Gly Lys Leu Ile Asn
                225                 230                 235 gat cca act ttc gct cta cct tac tgg aac tgg gat aac cct act gga      771
Asp Pro Thr Phe Ala Leu Pro Tyr Trp Asn Trp Asp Asn Pro Thr Gly
            240                 245                 250 atg gtt att cct gcc atg ttc gaa cag aac agc aaa act aac tct ctg      819
Met Val Ile Pro Ala Met Phe Glu Gln Asn Ser Lys Thr Asn Ser Leu
        255                 260                 265 ttt gac cct tta agg gat gcg aaa cac ctc cca cct tct atc ttt gat      867
Phe Asp Pro Leu Arg Asp Ala Lys His Leu Pro Pro Ser Ile Phe Asp
    270                 275                 280 gtt gaa tat gct ggt gca gac act ggt gcc act tgt ata gac cag ata      915
Val Glu Tyr Ala Gly Ala Asp Thr Gly Ala Thr Cys Ile Asp Gln Ile
285                 290                 295                 300 gcc att aat ctg tct tca atg tac aga cag atg gtc acc aac tcc act      963
Ala Ile Asn Leu Ser Ser Met Tyr Arg Gln Met Val Thr Asn Ser Thr
                305                 310                 315 gat aca aaa cga ttc ttc ggt ggc gaa ttt gta gct gga aat gac cct     1011
Asp Thr Lys Arg Phe Phe Gly Gly Glu Phe Val Ala Gly Asn Asp Pro
            320                 325                 330 ctt gcg agc gag ttc aac gta gct ggg acc gta gaa gct ggg gtt cac     1059
Leu Ala Ser Glu Phe Asn Val Ala Gly Thr Val Glu Ala Gly Val His
        335                 340                 345 act gcg gct cac cgc tgg gtg ggt aat tct agg atg gcc aac agc gaa     1107
Thr Ala Ala His Arg Trp Val Gly Asn Ser Arg Met Ala Asn Ser Glu
    350                 355                 360 gac atg ggg aac ttc tac tcc gca gga tat gat cct ctc ttt tac gtc     1155
Asp Met Gly Asn Phe Tyr Ser Ala Gly Tyr Asp Pro Leu Phe Tyr Val
365                 370                 375                 380 cac cat gcg aat gtc gac agg atg tgg caa atc tgg aaa gat att gac     1203
His His Ala Asn Val Asp Arg Met Trp Gln Ile Trp Lys Asp Ile Asp
                385                 390                 395 aag aag aca cac aag gat ccg acc tct ggc gac tgg cta aat gca tca     1251
Lys Lys Thr His Lys Asp Pro Thr Ser Gly Asp Trp Leu Asn Ala Ser
            400                 405                 410 tac gtg ttt tac gat gag aat gaa aat ctt gta cgt gtc tac aac cga     1299
Tyr Val Phe Tyr Asp Glu Asn Glu Asn Leu Val Arg Val Tyr Asn Arg
        415                 420                 425 gac tgt gta gac att aat cgg atg gga tat gac tac gaa agg tca gca     1347
Asp Cys Val Asp Ile Asn Arg Met Gly Tyr Asp Tyr Glu Arg Ser Ala
```

-continued

```
                 430                 435                 440
atc cca tgg atc cgt agt cgg ccg act gca cat gcg aag ggg gcg aac    1395
Ile Pro Trp Ile Arg Ser Arg Pro Thr Ala His Ala Lys Gly Ala Asn
445                 450                 455                 460 gtt gct gct aag tct gct gga atc gtg cag aag gtg gag gat atc gta    1443
Val Ala Ala Lys Ser Ala Gly Ile Val Gln Lys Val Glu Asp Ile Val
                465                 470                 475 ttc ccg ctg aag tta aac aag ata gtg aag gtt cta gtg aag agg cca    1491
Phe Pro Leu Lys Leu Asn Lys Ile Val Lys Val Leu Val Lys Arg Pro
            480                 485                 490 gct aca aac agg acc aag gag gga aag gag aaa gca aat gag ctg ttg    1539
Ala Thr Asn Arg Thr Lys Glu Gly Lys Glu Lys Ala Asn Glu Leu Leu
        495                 500                 505 ttc gtg aat gga atc acg ttt gat gct gag cgg ttt cta aag att gac    1587
Phe Val Asn Gly Ile Thr Phe Asp Ala Glu Arg Phe Leu Lys Ile Asp
    510                 515                 520 gtg ttt gtc aac gac gtc gac gat gga att cag acc acc gct gct gat    1635
Val Phe Val Asn Asp Val Asp Asp Gly Ile Gln Thr Thr Ala Ala Asp
525                 530                 535                 540 agt gag ttt gct ggt agt ttc gca cag ttg cca cat aac cat ggc gac    1683
Ser Glu Phe Ala Gly Ser Phe Ala Gln Leu Pro His Asn His Gly Asp
                545                 550                 555 aag atg ttt atg agg agt ggg gca gcg ttc ggg atc acg gag ctc ttg    1731
Lys Met Phe Met Arg Ser Gly Ala Ala Phe Gly Ile Thr Glu Leu Leu
            560                 565                 570 gaa gac att gaa gct gaa ggt gat gac tct gtt gtt gtg aca ttg gtg    1779
Glu Asp Ile Glu Ala Glu Gly Asp Asp Ser Val Val Val Thr Leu Val
        575                 580                 585 ccg aga aca ggg tgt gat gaa gta act att ggc gag atc aag att cag    1827
Pro Arg Thr Gly Cys Asp Glu Val Thr Ile Gly Glu Ile Lys Ile Gln
    590                 595                 600 ctg gtt ccc att gtt taaagtctat tgaagtaatg cattttcaat tgtcattagt    1882
Leu Val Pro Ile Val
605 atgcatgggt acgtaaatct gttcgctgtc tggttatcga ggattttga tgttctcgta    1942 accaaataat aaggattgtc attccatgtt tggaatcgtg taaccgcagg catgcatatg   2002 tttgattgtt attttactt gaagcacttc tgttttagta aaaaaaaaaa aaaaa          2057
```

<210> SEQ ID NO 30
<211> LENGTH: 609
<212> TYPE: PRT
<213> ORGANISM: lettuce

<400> SEQUENCE: 30

```
Met Ala Ser Leu Ala Leu Ser Ser Leu Pro Thr Ser Thr Thr Thr Lys
 1               5                  10                  15

Lys Pro Leu Phe Ser Lys Thr Ser Ser His Val Lys Pro Phe His Arg
            20                  25                  30

Phe Lys Val Ser Cys Asn Ala Pro Ala Asp Asn Asn Asp Lys Thr Val
        35                  40                  45

Asn Asn Ser Asp Thr Pro Lys Leu Ile Leu Pro Lys Thr Pro Leu Glu
    50                  55                  60

Thr Gln Asn Val Asp Arg Arg Asn Leu Leu Leu Gly Leu Gly Gly Leu
65                  70                  75                  80

Tyr Gly Ala Ala Asn Leu Thr Thr Ile Pro Ser Ala Phe Gly Ile Pro
                85                  90                  95

Ile Ala Ala Pro Asp Asn Ile Ser Asp Cys Val Ala Ala Thr Ser Asn
```

-continued

```
             100                 105                 110
Leu Arg Asn Ser Lys Asp Ala Ile Arg Gly Leu Ala Cys Cys Pro Pro
            115                 120                 125

Val Leu Ser Thr Asn Lys Pro Met Asp Tyr Val Leu Pro Ser Asn Pro
    130                 135                 140

Val Ile Arg Val Arg Pro Ala Ala Gln Lys Ala Thr Ala Asp Tyr Thr
145                 150                 155                 160

Ala Lys Tyr Gln Gln Ala Ile Gln Ala Met Lys Asp Leu Pro Glu Asp
                165                 170                 175

His Pro His Ser Trp Lys Gln Gln Gly Lys Ile His Cys Ala Tyr Cys
            180                 185                 190

Asn Gly Gly Tyr Asn Gln Glu Gln Ser Gly Tyr Pro Asn Leu Gln Leu
        195                 200                 205

Gln Ile His Asn Ser Trp Leu Phe Phe Pro Phe His Arg Trp Tyr Leu
    210                 215                 220

Tyr Phe Tyr Glu Lys Ile Leu Gly Lys Leu Ile Asn Asp Pro Thr Phe
225                 230                 235                 240

Ala Leu Pro Tyr Trp Asn Trp Asp Asn Pro Thr Gly Met Val Ile Pro
                245                 250                 255

Ala Met Phe Glu Gln Asn Ser Lys Thr Asn Ser Leu Phe Asp Pro Leu
            260                 265                 270

Arg Asp Ala Lys His Leu Pro Pro Ser Ile Phe Asp Val Glu Tyr Ala
        275                 280                 285

Gly Ala Asp Thr Gly Ala Thr Cys Ile Asp Gln Ile Ala Ile Asn Leu
    290                 295                 300

Ser Ser Met Tyr Arg Gln Met Val Thr Asn Ser Thr Asp Thr Lys Arg
305                 310                 315                 320

Phe Phe Gly Gly Glu Phe Val Ala Gly Asn Asp Pro Leu Ala Ser Glu
                325                 330                 335

Phe Asn Val Ala Gly Thr Val Glu Ala Gly Val His Thr Ala Ala His
            340                 345                 350

Arg Trp Val Gly Asn Ser Arg Met Ala Asn Ser Glu Asp Met Gly Asn
        355                 360                 365

Phe Tyr Ser Ala Gly Tyr Asp Pro Leu Phe Tyr Val His His Ala Asn
    370                 375                 380

Val Asp Arg Met Trp Gln Ile Trp Lys Asp Ile Asp Lys Lys Thr His
385                 390                 395                 400

Lys Asp Pro Thr Ser Gly Asp Trp Leu Asn Ala Ser Tyr Val Phe Tyr
                405                 410                 415

Asp Glu Asn Glu Asn Leu Val Arg Val Tyr Asn Arg Asp Cys Val Asp
            420                 425                 430

Ile Asn Arg Met Gly Tyr Asp Tyr Glu Arg Ser Ala Ile Pro Trp Ile
        435                 440                 445

Arg Ser Arg Pro Thr Ala His Ala Lys Gly Ala Asn Val Ala Ala Lys
    450                 455                 460

Ser Ala Gly Ile Val Gln Lys Val Glu Asp Ile Val Phe Pro Leu Lys
465                 470                 475                 480

Leu Asn Lys Ile Val Lys Val Leu Val Lys Arg Pro Ala Thr Asn Arg
                485                 490                 495

Thr Lys Glu Gly Lys Glu Lys Ala Asn Glu Leu Leu Phe Val Asn Gly
            500                 505                 510

Ile Thr Phe Asp Ala Glu Arg Phe Leu Lys Ile Asp Val Phe Val Asn
        515                 520                 525
```

Asp Val Asp Asp Gly Ile Gln Thr Thr Ala Ala Asp Ser Glu Phe Ala
    530                 535                 540

Gly Ser Phe Ala Gln Leu Pro His Asn His Gly Asp Lys Met Phe Met
545                 550                 555                 560

Arg Ser Gly Ala Ala Phe Gly Ile Thr Glu Leu Leu Glu Asp Ile Glu
                565                 570                 575

Ala Glu Gly Asp Asp Ser Val Val Val Thr Leu Val Pro Arg Thr Gly
                580                 585                 590

Cys Asp Glu Val Thr Ile Gly Glu Ile Lys Ile Gln Leu Val Pro Ile
        595                 600                 605

Val

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 31
gcgaattctt yytnccntty mymg                                          24

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 32
gcgaattcga tccnacntty gckttncc                                      28

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 33
gcgaattcaa ygtngaymgn atgtgg                                        26

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 34
gcgaattctn caytgygcnt aytg                                          24

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 35
gcgaattctt nccntwytgg aaytggg                                       27

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 36
gcctgcagcc acatnckrtc nacrtt                                  26

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 37
gcctgcagtt ytcrtcrtag aa                                      22

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 38
gactcgagtc gacatcgatt tttttttttt ttttt                        35

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 39
atatcacctg tcggtacatg acggc                                   25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 40
gtgccattgt agtcgaggtc aatca                                   25

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 41
ccagtgcctg gtttaggtgt attcac                                  26

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 42
tgctgttctg ttcgaacatg gcag                                    24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 43
tatacaagtg gcaccagtgt ctgc                                    24

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 44
ccgcattgtg gatgacttcc atctg                                   25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 45
ccagaatggg atggtgaagg tgtcg                                   25

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 46
cgctgggtgg gtaattctag gatg                                    24

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 47
agtcatccac aatgcggcgc acatg                                   25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 48
gttgctcttc ttaggctcgg cttac                                   25

<210> SEQ ID NO 49
<211> LENGTH: 17

```
<212> TYPE: DNA
<213> ORGANISM: Artificial Sequence
<220> FEATURE:
<223> OTHER INFORMATION: Description of Artificial Sequence:  primer

<400> SEQUENCE: 49
gactcgagtc gacatcg                                                    17
```